US009422528B2

(12) United States Patent
Suphaphiphat et al.

(10) Patent No.: US 9,422,528 B2
(45) Date of Patent: Aug. 23, 2016

(54) INFLUENZA VIRUS REASSORTMENT

(71) Applicant: Novartis AG, Basel (CH)

(72) Inventors: Pirada Suphaphiphat, Brookline, MA (US); Peter Mason, Somerville, MA (US); Bjoern Keiner, Basel (CH); Philip Dormitzer, Weston, MA (US); Heidi Trusheim, Apex, NC (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/909,013

(22) Filed: Jun. 3, 2013

(65) Prior Publication Data

US 2014/0030291 A1    Jan. 30, 2014

Related U.S. Application Data

(63) Continuation of application No. PCT/EP2013/054227, filed on Mar. 2, 2013.

(60) Provisional application No. 61/605,922, filed on Mar. 2, 2012, provisional application No. 61/685,766, filed on Mar. 23, 2012.

(51) Int. Cl.
*A61K 39/145* (2006.01)
*C12N 7/00* (2006.01)

(52) U.S. Cl.
CPC ........ *C12N 7/00* (2013.01); *C12N 2760/16121* (2013.01); *C12N 2760/16134* (2013.01)

(58) Field of Classification Search
None
See application file for complete search history.

(56) References Cited

U.S. PATENT DOCUMENTS 6,656,720 B2    12/2003    Groner et al.

FOREIGN PATENT DOCUMENTS

| DE | 19612966 A1 | 10/1997 |
| WO | WO-97/37000 A1 | 10/1997 |
| WO | WO-2007/126810 A2 | 11/2007 |
| WO | WO-2010/070098 A1 | 6/2010 |
| WO | WO-2010/077986 A2 | 7/2010 |
| WO | WO-2011/056591 A1 | 5/2011 |
| WO | WO-2013/032942 A1 | 3/2013 |

OTHER PUBLICATIONS

Thangavel et al. "Boom" and "Bust" cycles in virus growth suggest multiple selective forces in influenza a evolution. Virology Journal 2011, 8:180-.*
GenBank: JF690258.1. Influenza A virus (A/reassortant/IgYRP16(California/07/2004×Puerto Rico/8/1934)(H3N2)) segment 2 polymerase PB1 (PB1) and PB1-F2 protein (PB1-F2) genes, complete cds. http://www.ncbi.nlm.nih.gov/nucleotide/326579217?report=genbank&log$=nuclalign&blast_rank=100&RID=5U4J39PE01R. Apr. 24, 2011.*
GenBank: JF690256.1. Influenza A virus (A/reassortant/IgYRP16(California/07/2004×Puerto Rico/8/1934)(H3N2)) segment 1 polymerase PB2 (PB2) gene, complete cds. http://www.ncbi.nlm.nih.gov/nuccore/JF690256. Apr. 24, 2011.*
Webby et al. Responsiveness to a pandemic alert: use of reverse genetics for rapid development of influenza vaccines. Lancet 2004; 363: 1099-103.*
Ozaki et al. Generation of high-yielding influenza A viruses in African green monkey kidney (Vero) cells by reverse genetics. J Virol. Feb. 2004;78(4):1851-7.*
Abt et al. (2011). "Improvement of H5N1 influenza vaccine viruses: influence of internal gene segments of avian and human origin on production and hemagglutinin content," Vaccine, 29(32):5153-62.
Fulvini et al. (2011). "Gene constellation of influenza A virus reassortants with high growth phenotype prepared as seed candidates for vaccine production," PLoS One, 6(6):e20823.
Ha et al. (2011). "Proteotyping to establish gene origin within reassortant influenza viruses," PLoS One, 6(1):e15771.
International Search Report, mailed Sep. 24, 2013, for International Application No. PCT/EP2013/054227, filed Mar. 2, 2013.

* cited by examiner

*Primary Examiner* — Nick Zou
(74) *Attorney, Agent, or Firm* — Finnegan, Henderson, Farabow, Garrett & Dunner, LLP

(57) ABSTRACT

New influenza donor strains for the production of reassortant influenza A viruses are provided.

29 Claims, 18 Drawing Sheets

(A)

(B)

(A)

(B)

(A)

(B)

(A)

(B)

(A)

(B)

(A)

(B)

(A)

(B)

(A)

(B)

(A)

(B)

(A)

(B)

(C)

(D)

(A)

(B)

(C)

(D)

(A)

(B)

(A)

(B)

(C)

(D)

```
105p30    1 mslltevetyvlsivpsgplkaeiaqrlenvfagkntdlealmewlktrp   50
            ||||||||||||||||||||||||||||||||||||||||||||||||||
A/NC/20/66  1 mslltevetyvlsivpsgplkaeiaqrlenvfagkntdlealmewlktrp   50

105p30   51 ilspltkgilgfvftltvpserglqrrrfvqnalngngdpnnmdravkly  100
            ||||||||||||||||||||||||||||||||||||||||:|

INFLUENZA VIRUS REASSORTMENT

This patent application is a continuation of International Application No. PCT/EP2013/054227, filed Mar. 2, 2013, which claims priority from U.S. provisional patent applications 61/605,922, filed Mar. 2, 2012 and 61/685,766 filed Mar. 23, 2012, the complete contents of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: PAT055008_ST25.txt, date recorded: May 22, 2013, size: 161 KB).

TECHNICAL FIELD

This invention is in the field of influenza A virus reassortment. Furthermore, it relates to manufacturing vaccines for protecting against influenza A viruses.

BACKGROUND ART

The most efficient protection against influenza infection is vaccination against circulating strains and it is important to produce influenza viruses for vaccine production as quickly as possible.

Wild-type influenza viruses often grow to low titres in eggs and cell culture. In order to obtain a better-growing virus strain for vaccine production it is currently common practice to reassort the circulating vaccine strain with a faster-growing high-yield donor strain. This can be achieved by co-infecting a culture host with the circulating influenza strain (the vaccine strain) and the high-yield donor strain and selecting for reassortant viruses which contain the hemagglutinin (HA) and neuraminidase (NA) segments from the vaccine strain and the other viral segments (i.e. those encoding PB1, PB2, PA, NP, $M_1$, $M_2$, $NS_1$ and $NS_2$) from the donor strain. Another approach is to reassort the influenza viruses by reverse genetics (see, for example references 1 and 2).

Reference 3 reports that a reassortant influenza virus containing a PB1 gene segment from A/Texas/1/77, the HA and NA segments from A/New Caledonia/20/99, a modified PA segment derived from A/Puerto Rico/8/34 and the remaining viral segments from A/Puerto Rico/8/34 shows increased growth in cells.

There are currently only a limited number of donor strains for reassorting influenza viruses for vaccine manufacture, and the strain most commonly used is the A/Puerto Rico/8/34 (A/PR/8/34) strain. However, reassortant influenza viruses comprising A/PR/8/34 backbone segments do not always grow sufficiently well to ensure efficient vaccine manufacture. Thus, there is a need in the art to provide further and improved donor strains for influenza virus reassortment.

SUMMARY OF PREFERRED EMBODIMENTS

The inventors have now surprisingly discovered that influenza viruses which comprise backbone segments from two or more influenza donor strains can grow faster in a culture host compared with reassortant influenza A viruses which contain all backbone segments from the same donor strain. In particular, the inventors have found that influenza viruses which comprise backbone segments derived from two high-yield donor strains can produce higher yield reassortants with target vaccine-relevant HA/NA genes than reassortants made with either of the two original donor strains.

In principle, all segments of closely related influenza A viruses can be specifically reassorted to produce viable viruses, but only a small fraction of these viruses will be high-growth reassortants, due to inefficient activities of the resulting viral components. The inventors have provided backbone combinations that produce the high yield strains. Reassortant influenza A viruses comprising backbone segments from two or more influenza donor strains may contain the PB1 and the PB2 viral segments from the same donor strain, in particular the A/New Caledonia/20/1999-like strain, referred to herein as the 105p30 strain. The PB1 and PB2 viral segments may have at least 95% identity or 100% identity with the sequence of SEQ ID NO: 2 and/or SEQ ID NO: 3.

Where the reassortant influenza A virus comprises backbone segments from two or three donor strains, each donor strain may provide more than one of the backbone segments of the reassortant influenza A virus, but one or two of the donor strains can also provide only a single backbone segment.

Where the reassortant influenza A virus comprises backbone segments from two, three, four or five donor strains, one or two of the donor strains may provide more than one of the backbone segments of the reassortant influenza A virus. In general the reassortant influenza A virus cannot comprise more than six backbone segments. Accordingly, for example, if one of the donor strains provides five of the viral segments, the reassortant influenza A virus can only comprise backbone segments from a total of two different donor strains.

Where a reassortant influenza A virus comprises the PB1 segment from A/Texas/1/77, it preferably does not comprise the PA, NP or M segment from A/Puerto Rico/8/34. Where a reassortant influenza A virus comprises the PA, NP or M segment from A/Puerto Rico/8/34, it preferably does not comprise the PB1 segment from A/Texas/1/77. In some embodiments, the invention does not encompass reassortant influenza A viruses which have the PB1 segment from A/Texas/1/77 and the PA, NP and M segments from A/Puerto Rico/8/34. The PB1 segment from A/Texas/1/77 may have the sequence of SEQ ID NO: 46 and the PA, NP or M segments from A/Puerto Rico/8/34 may have the sequence of SEQ ID NOs 47, 48 or 49, respectively.

The inventors have also discovered that variants of known donor strains can grow to higher viral titres compared to the original donor strain and can therefore be better donor strains for reassorting influenza viruses. Examples of such strains are PR8-X and 105p30.

Influenza A virus strains of the invention can grow to higher viral titres in MDCK cells in the same time and under the same growth conditions compared with A/Puerto Rico/8/34 and/or have a higher rescue efficiency compared with reassortant influenza strains that comprise all backbone segments from the same influenza donor strain. Further provided is a reassortant influenza A virus comprising at least one backbone viral segment from such an influenza strain.

The invention also provides a reassortant influenza A virus comprising at least one backbone viral segment from a donor strain, wherein the donor strain is selected from the group consisting of 105p30 and PR8-X. When the at least one backbone viral segment is the PA segment it may have a sequence having at least 95% or at least 99% identity with a sequence selected from the group consisting of SEQ ID NOs: 9 and 17. When the at least one backbone viral segment is the PB1 segment, it may have a sequence having at least 95% or at least 99% identity with a sequence selected from the group consisting of SEQ ID NOs 10 and 18. When the at least one backbone viral segment is the PB2 segment, it may have a sequence having at least 95% or at least 99% identity with a sequence selected from the group consisting of or SEQ ID NOs: 11 and 19. When the at least one backbone viral segment is the M segment it may have a sequence having at least 95% or at least 99% identity with a sequence selected from the group consisting of SEQ ID NOs: 13 and 21. When the at least one backbone viral segment is the NP segment it may have a sequence having at least 95% or at least 99% identity with a sequence selected from the group consisting of SEQ ID NOs: 12 and 20. When the at least one backbone viral segment is the NS segment it may have a sequence having at least 95% or at least 99% identity with a sequence selected from the group consisting of SEQ ID NOs: 14 and 22.

In embodiments where the reassortant influenza A virus comprises backbone segments from at least two influenza donor strains, at least one backbone segment may be derived from a donor strain selected from the group consisting of 105p30 and PR8-X, as discussed in the previous paragraph. Preferred reassortant influenza A viruses comprise 1, 2, 3 or 4 viral segments from the 105p30 donor strain wherein the PA segment may have at least 95% identity or 100% identity with SEQ ID NO: 17, the NP segment may have at least 95% identity or 100% identity with SEQ ID NO: 20, the M segment may have at least 95% identity or 100% identity with SEQ ID NO: 21, and/or the NS segment may have at least 95% identity or 100% identity with SEQ ID NO: 22. In some embodiments such influenza A viruses may also comprise at least one backbone viral segment from the PR8-X donor strain. Where the at least one viral segment is the PA segment it may have at least 95% identity or 100% identity with SEQ ID NO: 9. Where the at least one viral segment is the NP segment it may have at least 95% identity or 100% identity with SEQ ID NO: 12. Where the at least one viral segment is the M segment it may have at least 95% identity or 100% identity with SEQ ID NO: 13. Where the at least one viral segment is the NS segment it may have at least 95% identity or 100% identity with SEQ ID NO: 9. The inventors have shown that reassortant influenza A viruses comprising such backbone segments grow well in cell culture. In general a reassortant influenza virus will contain only one of each backbone segment. For example, when the influenza virus comprises the PA segment from 105p30 it will not at the same time comprise the PA segment of PR8-X.

In preferred embodiments, the virus comprises viral segments having at least 95% identity or 100% identity with the sequence of (a) the PB2 segment of SEQ ID NO: 19, the PB 1 segment of SEQ ID: NO 18 and the NS segment of SEQ ID NO: 22; or (b) the PB2 segment of SEQ ID NO: 19, the PB1 segment of SEQ ID NO: 18 and the M segment of SEQ ID NO: 21; or (c) the PB2 segment of SEQ ID NO: 19, the PB1 segment of SEQ ID NO: 18 and the NP segment of SEQ ID NO: 20; or (d) the PB2 segment of SEQ ID NO 19, the PB1 segment of SEQ ID NO 18 and the PA segment of SEQ ID NO 17. These embodiments are preferred because the inventors have found that such reassortant influenza A viruses grow particularly well in cell culture.

The invention provides a method of preparing the reassortant influenza A viruses of the invention. These methods comprise steps of (i) introducing into a culture host one or more expression construct(s) which encode(s) the viral segments required to produce an influenza A virus wherein the backbone viral segments are from two or more influenza strains; and (ii) culturing the culture host in order to produce reassortant virus and optionally (iii) purifying the virus obtained in step (ii).

The method may comprise the steps of (i) introducing into a culture host one or more expression construct(s) which encode(s) the viral segments required to produce an influenza A virus wherein the backbone viral segments are from two or more influenza strains and the PB1 and PB2 segments are from the same donor strain; and (ii) culturing the culture host in order to produce reassortant virus and optionally (iii) purifying the virus obtained in step (ii).

Also provided is a method of preparing a reassortant influenza A virus of the invention comprising the steps of (i) introducing into a culture host one or more expression construct(s) which encode(s) the viral segments required to produce an influenza A virus wherein the backbone viral segments are from two or more influenza strains and the HA and the PB 1 segment are from different influenza strains which have the same influenza HA subtype; and (ii) culturing the culture host in order to produce reassortant virus and optionally (iii) purifying the virus obtained in step (ii).

The invention also provides a method of preparing a reassortant influenza A virus of the invention comprising steps of (i) introducing into a culture host one or more expression construct(s) which encode(s) the viral segments required to produce an influenza A virus wherein one or more backbone viral segment(s) is/are from a 105p30 and/or a PR8-X influenza strain and wherein at least one viral segment is derived from a second influenza strain; and (ii) culturing the culture host in order to produce reassortant virus and optionally (iii) purifying the virus obtained in step (ii).

The methods may further comprise steps of: (iv) infecting a culture host with the virus obtained in step (ii) or step (iii); (v) culturing the culture host from step (iv) to produce further virus; and optionally (vi) purifying the virus obtained in step (v).

The invention also provides a method for producing influenza viruses comprising steps of (a) infecting a culture host with a reassortant virus of the invention; (b) culturing the host from step (a) to produce the virus; and optionally (c) purifying the virus obtained in step (b).

The invention also provides a method of preparing a vaccine, comprising steps of (d) preparing a virus by the methods of any one of the embodiments described above and (e) preparing vaccine from the virus.

In a further embodiment, the invention provides influenza strains PR8-X and 105p30.

The invention also encompasses variant H1N1 influenza virus strains in which the M genome segment has lysine in the position corresponding to amino acid 95 of SEQ ID NO: 33 when aligned to SEQ ID NO: 33 using a pairwise alignment algorithm. The variant H1N1 influenza virus strains according to the invention may further have a HA segment which has glycine in the position corresponding to amino acid 225 of SEQ ID NO: 35 when aligned to SEQ ID NO: 35 and/or has asparagine in the position corresponding to amino acid 231 of SEQ ID NO: 35 when aligned to SEQ ID NO: 35 using a pairwise alignment algorithm. The variant H1N1 influenza virus strain may also have a NA segment which has histidine in the position corresponding to amino acid 70 of SEQ ID NO: 31 when aligned to SEQ ID NO: 31 using a pairwise alignment algorithm.

The preferred pairwise alignment algorithm is the Needleman-Wunsch global alignment algorithm [4], using default parameters (e.g. with Gap opening penalty=10.0, and with Gap extension penalty =0.5, using the EBLOSUM62 scoring matrix). This algorithm is conveniently implemented in the needle tool in the EMBOSS package [5].

The invention provides an expression system comprising one or more expression construct(s) comprising the vRNA encoding segments of an influenza A virus wherein the expression construct(s) encode(s) the backbone viral segments from two or more influenza donor strains. The expression construct(s) may encode the PB1 and PB2 segments from the same donor strain.

The invention also provides an expression system comprising one or more expression construct(s) comprising the vRNA encoding segments of a 105p30 or PR8-X strain wherein the expression construct(s) comprise(s) at least one backbone viral segment from the 105p30 or PR8-X, or strain. The expression construct(s) may further comprise the vRNAs which encode the PB2, NP, NS, M and PA segments from PR8-X.

The invention also provides a host cell comprising the expression systems of the invention. These host cells can express an influenza A virus from the expression construct(s) in the expression system.

Expression constructs which can be used in the expression systems of the invention are also provided. For example, the invention provides an expression construct which encodes the backbone segments of the reassortant influenza strains according to the invention on the same construct.

Donor Strains

Influenza donor strains are strains which typically provide the backbone segments in a reassortant influenza virus, even though they may sometimes also provide the HA or NA segment, but not both, of the virus. Usually, however, both the HA and the NA segment in a reassortant influenza virus will be from the vaccine strain.

The inventors have surprisingly discovered that reassortant influenza A viruses comprising backbone segments from two or more influenza donor strains can grow to higher titres in cell culture compared with reassortant influenza viruses which contain all backbone segments from the same donor strain. The inventors have shown that this effect is due to the presence of backbone segments from two donor strains and does not require the presence of viral segments with specific mutations. Particularly good results are achieved, however, with influenza A strains in which the M genome segment has lysine in the position corresponding to amino acid 95 of SEQ ID NO: 33 when aligned to SEQ ID NO: 33.

Reassortant influenza A viruses comprising the PB1 and PB2 segments from the same influenza strain (for example 105p30) are also advantageous because they showed a better rescue efficiency compared with influenza viruses in which the PB1 and PB2 segments are from different viruses. The PB1 and PB2 segments of 105p30 have the sequence of SEQ ID NOs 18 and 19, respectively.

The inventors have also shown that some influenza virus strains can grow to higher viral titres in MDCK cells in the same time and under the same growth conditions compared with A/Puerto Rico/8/34.

Variants of influenza donor strains which are derived from the donor strains of the invention or other known donor strains such A/PR/8/34 (wt PR8) can also be useful as donor strains. These donor strains can grow to higher viral titres (in the same time and under the same growth conditions) compared to the donor strain from which they are derived. For example, the inventors have surprisingly discovered that passaging the A/PR/8/34 influenza strain several times in cell culture results in a virus strain (PR8-X) which grows to much higher viral titres compared to the original A/PR8/34 strain. Likewise, the inventors have found that passaging the A/New Caledonia/20/1999 strain several times in cells results in a virus (105p30) which grows to even higher viral titres compared to the unpassaged A/New Caledonia/20/1999 strain in the same time and under the same growth conditions. Donor strain variants of the present invention will typically achieve viral titres which are at least 10%, at least 20%, at least 50%, at least 100%, at least 200%, at least 500% or at least 1000% higher under the same growth conditions and for the same time (for example 12 hours, 24 hours, 48 hours or 72 hours) compared to the viral titres obtained with the donor strain from which the variant was derived.

The segments of PR8-X have the sequences of SEQ ID NO: 11 (PB2), SEQ ID NO: 10 (PB1), SEQ ID NO: 9 (PA), SEQ ID NO: 12 (NP), SEQ ID NO: 13 (M), SEQ ID NO: 14 (NS), SEQ ID NO: 15 (HA) or SEQ ID NO: 16 (NA).

The segments of 105p30 have the sequences of SEQ ID NO: 19 (PB2), SEQ ID NO: 18 (PB1), SEQ ID NO: 17 (PA), SEQ ID NO: 20 (NP), SEQ ID NO: 21 (M), SEQ ID NO: 22 (NS), SEQ ID NO: 23 (HA) or SEQ ID NO: 24 (NA).

Influenza strains which contain one, two, three, four five, six or seven of the segments of the 105p30 or PR8-X strains can also be used as donor strains.

The invention can be practised with donor strains having a viral segment that has at least about 70%, at least about 75%, at least about 80%, at least about 85%, at least about 90%, at least about 95% or at least about 99% identity to a sequence of SEQ ID NOs 11-14 or 18-22. For example, due to the degeneracy of the genetic code, it is possible to have the same polypeptide encoded by several nucleic acids with different sequences. Thus, the invention may be practised with viral segments that encode the same polypeptides as the sequences of SEQ ID NOs 11-14 or 18-22. For example, the nucleic acid sequences of SEQ ID NOs: 3 and 28 have only 73% identity even though they encode the same viral protein.

The invention may also be practised with viral segments that encode polypeptides that have at least 80%, at least 85%, at least 90%, at least 95% or at least 99% identity to the polypeptide sequences encoded by SEQ ID NOs 11-14 or 18-22.

Variations in the DNA and the amino acid sequence may also stem from spontaneous mutations which can occur during passaging of the viruses. Such variant influenza strains can also be used in the invention.

Reassortant Viruses

The invention provides reassortant influenza viruses which comprise backbone segments from two or more influenza donor strains. The PB 1 and PB2 segments may be from the same donor strain.

The invention also provides reassortant influenza viruses comprising at least one backbone viral segment from an influenza virus strain that can grow to higher viral titres in MDCK cells in the same time and under the same growth conditions compared with A/Puerto Rico/8/34.

The invention provides reassortant influenza viruses comprising at least one backbone viral segment from the donor strains of the invention, e.g. a PR8-X or 105p30 strain. The reassortant influenza viruses of the invention can be reassortants between two, three or more different influenza strains provided that at least one viral segment is derived from a donor strain of the invention.

Influenza viruses are segmented negative strand RNA viruses. Influenza A and B viruses have eight segments (NP, M, NS, PA, PB1, HA and NA) whereas influenza C virus has seven. The reassortant viruses of the invention contain the backbone segments from two or more donor strains, or at least one (i.e. one, two, three, four, five or six) backbone viral segment from the donor strains of the invention. The backbone viral segments are those which do not encode HA or NA. Thus, backbone segments will typically encode the PB1, PB2, PA, NP, $M_1$, $M_2$, $NS_1$ and $NS_2$ polypeptides of the influenza virus. The reassortant viruses will not typically contain the segments encoding HA and NA from the donor strains even though reassortant viruses which comprise either the HA or the NA but not both from the donor strains of the invention are also envisioned.

When the reassortant viruses of the invention are reassortants comprising the backbone segments from a single donor strain, the reassortant viruses will generally include segments from the donor strain and the vaccine strain in a ratio of 1:7, 2:6, 3:5, 4:4, 5:3, 6:2 or 7:1. Having a majority of segments from the donor strain, in particular a ratio of 6:2, is typical. When the reassortant viruses comprise backbone segments from two donor strains, the reassortant virus will generally include segments from the first donor strain, the seconds donor strain and the vaccine strain in a ratio of 1:1:6, 1:2:5, 1:3:4, 1:4:3, 1:5:2, 1:6:1, 2:1:5, 2:2:4, 2:3:3, 2:4:2, 2:5:1, 3:1:2, 3:2:1, 4:1:3, 4:2:2, 4:3:1, 5:1:2, 5:2:1 or 6:1:1.

Preferably, the reassortant viruses do not contain the HA segment of the donor strain as this encodes the main vaccine antigens of the influenza virus and should therefore come from the vaccine strain. The reassortant viruses of the invention therefore preferably have at least the HA segment and typically the HA and NA segments from the vaccine strain.

The invention also encompasses reassortant viruses which contain viral segments from more than one, for example two or three different, donor strain(s) wherein at least one viral segment, preferably not HA, is derived from the PR8-X or 105p30 influenza strains. Such reassortant influenza viruses will typically contain the HA and/or NA segment from a vaccine strain. Where the reassortants contain viral segments from more than one influenza donor strain, the further donor strain(s) can be any donor strain including the donor strains of the invention. For example, some of the viral segments may be derived from the A/PR/8/34 or AA/6/60 (A/Ann Arbor/6/60) influenza strains. Reassortants containing viral segments from the AA/6/60 strain may be advantageous, for example, where the reassortant virus is to be used in a live attenuated influenza vaccine.

The invention also encompasses reassortants which comprise viral segments from more than one vaccine strain provided that the reassortant comprises a backbone according to the present invention. For example, the reassortant influenza viruses may comprise the HA segment from one donor strain and the NA segment from a different donor strain.

The reassortant viruses of the invention can grow to higher viral titres than the wild-type vaccine strain from which some of the viral segment(s) of the reassortant virus are derived in the same time (for example 12 hours, 24 hours, 48 hours or 72 hours) and under the same growth conditions. The viral titre can be determined by standard methods known to those of skill in the art. The reassortant viruses of the invention can achieve a viral titre which is at least 10% higher, at least 20% higher, at least 50% higher, at least 100% higher, at least 200% higher, at least 500% higher, or at least 1000% higher than the viral titre of the wild type vaccine strain in the same time frame and under the same conditions.

The invention is suitable for reassorting pandemic as well as inter-pandemic (seasonal) influenza vaccine strains. The reassortant influenza strains may contain the influenza A virus HA subtypes H1, H2, H3, H4, H5, H6, H7, H8, H9, H10, H11, H12, H13, H14, H15 or H16. They may contain the influenza A virus NA subtypes N1, N2, N3, N4, N5, N6, N7, N8 or N9. Where the vaccine strain used in the reassortant influenza viruses of the invention is a seasonal influenza strain, the vaccine strain may have a H1 or H3 subtype. In one aspect of the invention the vaccine strain is a H1N1 or $H_3N_2$ strain.

The vaccine strains for use in the invention may also be pandemic strains or potentially pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A vaccine strain with H5 hemagglutinin type is preferred where the reassortant virus is used in vaccines for immunizing against pandemic influenza, such as a H5N1 strain. Other possible strains include H5N3, H9N2, H2N2, H7N1 and H7N7, and any other emerging potentially pandemic strains. The invention is particularly suitable for producing reassortant viruses for use in vaccine for protecting against potential pandemic virus strains that can or have spread from a non-human animal population to humans, for example a swine-origin H1N1 influenza strain.

The reassortant influenza strain of the invention may comprise the HA segment and/or the NA segment from an A/California/4/09 strain. Thus, for instance, the HA gene segment may encode a H1 hemagglutinin which is more closely related to SEQ ID NO: 32 than to SEQ ID NO: 25 (i.e. has a higher degree sequence identity when compared to SEQ ID NO: 32 than to SEQ ID NO: 25 using the same algorithm and parameters). SEQ ID NOs: 32 and 25 are 80% identical. Similarly, the NA gene may encode a N1 neuraminidase which is more closely related to SEQ ID NO: 27 than to SEQ ID NO: 26. SEQ ID NOs: 27 and 26 are 82% identical.

Strains which can be used as vaccine strains include strains which are resistant to antiviral therapy (e.g. resistant to oseltamivir [6] and/or zanamivir), including resistant pandemic strains [7].

The choice of donor strain for use in the methods of the invention can depend on the vaccine strain which is to be reassorted. As reassortants between evolutionary distant strains might not replicate well in cell culture, it is possible that the donor strain and the vaccine strain have the same HA and/or NA subtype. In other embodiments, however, the vaccine strain and the donor strain can have different HA and/or NA subtypes, and this arrangement can facilitate selection for reassortant viruses that contain the HA and/or NA segment from the vaccine strain. Therefore, although the 105p30 and PR8-X strains contain the H1 influenza subtype these donor strains can be used for vaccine strains which do not contain the H1 influenza subtype.

Reassortants of the donor strains of the invention wherein the HA and/or NA segment has been changed to another subtype can also be used. The H1 influenza subtype of the 105p30 or PR8-X strain may be changed, for example, to a H3 or H5 subtype.

Thus, the invention encompasses an influenza A virus which comprises one, two, three, four, five, six or seven viral segments from the 105p30 or PR8-X strains of the invention and a HA segment which is not of the H1 subtype. The reassortant donor strains may further comprise an NA segment which is not of the N1 subtype. Suitable techniques for reassorting the donor strains will be evident to those of skill in the art.

The invention also encompasses reassortant donor strains which comprise at least one, at least two, at least three, at least four, at least five, at least six or at least seven viral segments from the 105p30 or PR8-X strains of the invention and a H1 HA segment which is derived from a different influenza strain.

Reassortant viruses which contain an NS segment that does not encode a functional NS protein are also within the scope of the present invention. NS1 knockout mutants are described in reference 8. These NS1-mutant virus strains are particularly suitable for preparing live attenuated influenza vaccines.

The 'second influenza strain' used in the methods of the invention is different to the donor strain which is used.

Reverse Genetics

The invention is particularly suitable for producing reassortant influenza virus strains through reverse genetics techniques. In these techniques, the viruses are produced in culture hosts using an expression system.

In one aspect, the expression system may encode the PB1 and PB2 segments from the same donor strain. In this aspect of the invention, the system may encode at least one (i.e. one, two three or four) of the segments NP, M, NS and/or PA from another influenza donor strain.

In another aspect, the system may encode 1 or more (e.g. 1, 2, 3, 4, 5 or 6) genome segments from the PR8-X strain, but usually this/these will not include the PR8-X HA segment and usually will not include the PR8-X NA segment. Thus the system may encode at least one of segments NP, M, NS, PA, PB1 and/or PB2 (possibly all six) from PR8-X.

The system may encode 1 or more (e.g. 1, 2, 3, 4, 5 or 6) genome segments from the 105p30 strain, but usually this/these will not include the 105p30 HA segment and usually will not include the 105p30 NA segment. Thus the system may encode at least one of segments NP, M, NS, PA, PB1 and/or PB2 (possibly all six) from 105p30.

Reverse genetics for influenza A and B viruses can be practised with 12 plasmids to express the four proteins required to initiate replication and transcription (PB 1, PB2, PA and nucleoprotein) and all eight viral genome segments. To reduce the number of constructs, however, a plurality of RNA polymerase I transcription cassettes (for viral RNA synthesis) can be included on a single plasmid (e.g. sequences encoding 1, 2, 3, 4, 5, 6, 7 or all 8 influenza vRNA segments), and a plurality of protein-coding regions with RNA polymerase II promoters on another plasmid (e.g. sequences encoding 1, 2, 3, 4, 5, 6, 7 or 8 influenza mRNA transcripts) [9]. It is also possible to include one or more influenza vRNA segments under control of a pol I promoter and one or more influenza protein coding regions under control of another promoter, in particular a pol II promoter, on the same plasmid. This is preferably done by using bi-directional plasmids.

Preferred aspects of the reference 9 method involve: (a) PB 1, PB2 and PA mRNA-encoding regions on a single expression construct; and (b) all 8 vRNA encoding segments on a single expression construct. Including the neuraminidase (NA) and hemagglutinin (HA) segments on one expression construct and the six other viral segments on another expression construct is particularly preferred as newly emerging influenza virus strains usually have mutations in the NA and/or HA segments. Therefore, the advantage of having the HA and/or NA segments on a separate expression construct is that only the vector comprising the HA and NA sequence needs to be replaced. Thus, in one aspect of the invention the NA and/or HA segments of the vaccine strain may be included on one expression construct and the vRNA encoding segments from the donor strain(s) of the invention, excluding the HA and/or NA segment(s), are included on a different expression construct. The invention thus provides an expression construct comprising one, two, three, four, five or six vRNA encoding backbone viral segments of a donor strain of the invention. The expression construct may not comprise HA and/or NA viral segments that produce a functional HA and/or NA protein.

Known reverse genetics systems involve expressing DNA molecules which encode desired viral RNA (vRNA) molecules from pol I promoters, bacterial RNA polymerase promoters, bacteriophage polymerase promoters, etc. As influenza viruses require the presence of viral polymerase to complete the life cycle, systems may also provide these proteins e.g. the system further comprises DNA molecules that encode viral polymerase proteins such that expression of both types of DNA leads to assembly of a complete infectious virus. It is also possible to supply the viral polymerase as a protein.

Where reverse genetics is used for the expression of influenza vRNA, it will be evident to the person skilled in the art that precise spacing of the sequence elements with reference to each other is important for the polymerase to initiate replication. It is therefore important that the DNA molecule encoding the viral RNA is positioned correctly between the pol I promoter and the termination sequence, but this positioning is well within the capabilities of those who work with reverse genetics systems.

In order to produce a recombinant virus, a cell must express all segments of the viral genome which are necessary to assemble a virion. DNA cloned into the expression constructs of the present invention preferably provides all of the viral RNA and proteins, but it is also possible to use a helper virus to provide some of the RNA and proteins, although systems which do not use a helper virus are preferred. As the influenza virus is a segmented virus, the viral genome will usually be expressed using more than one expression construct in the methods of the invention. It is also envisioned, however, to combine one or more segments or even all segments of the viral genome on a single expression construct.

In some embodiments an expression construct will also be included which leads to expression of an accessory protein in the host cell. For instance, it can be advantageous to express a non-viral serine protease (e.g. trypsin) as part of a reverse genetics system.

Expression Constructs

Expression constructs used in the expression systems of the invention may be uni-directional or bi-directional expression constructs. Where more than one transgene is used in the methods (whether on the same or different expression constructs) it is possible to use uni-directional and/or bi-directional expression.

As influenza viruses require a protein for infectivity, it is generally preferred to use bi-directional expression constructs as this reduces the total number of expression constructs required by the host cell. Thus, the method of the invention may utilise at least one bi-directional expression construct wherein a gene or cDNA is located between an upstream pol II promoter and a downstream non-endogenous pol I promoter. Transcription of the gene or cDNA from the pol II promoter produces capped positive-sense viral mRNA which can be translated into a protein, while transcription from the non-endogenous pol I promoter produces negative-sense vRNA. The bi-directional expression construct may be a bi-directional expression vector.

Bi-directional expression constructs contain at least two promoters which drive expression in different directions (i.e. both 5' to 3' and 3' to 5') from the same construct. The two promoters can be operably linked to different strands of the same double stranded DNA. Preferably, one of the promoters is a pol I promoter and at least one of the other promoters is a pol II promoter. This is useful as the pol I promoter can be used to express uncapped vRNAs while the pol II promoter can be used to transcribe mRNAs which can subsequently be translated into proteins, thus allowing simultaneous expression of RNA and protein from the same construct. Where more than one expression construct is used within an expression system, the promoters may be a mixture of endogenous and non-endogenous promoters.

The pol I and pol II promoters used in the expression constructs may be endogenous to an organism from the same taxonomic order from which the host cell is derived. Alternatively, the promoters can be derived from an organism in a different taxonomic order than the host cell. The term "order" refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora). For example, the human pol I promoter can be used to express viral segments in canine cells (e.g. MDCK cells).

The expression construct will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription termination sequence, and ribozymes. Furthermore, the expression constructs may contain one or more polyadenylation signals for mRNAs, particularly at the end of a gene whose expression is controlled by a pol II promoter.

An expression system may contain at least two, at least three, at least four, at least five, at least six, at least seven, at least eight, at least nine, at least ten, at least eleven or at least twelve expression constructs.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

As an alternative, an expression construct may be a linear expression construct. Such linear expression constructs will typically not contain any amplification and/or selection sequences. However, linear constructs comprising such amplification and/or selection sequences are also within the scope of the present invention. Reference 10 describes a linear expression construct which describes individual linear expression constructs for each viral segment. It is also possible to include more than one, for example two, three four, five or six viral segments on the same linear expression construct. Such a system has been described, for example, in reference 11.

Expression constructs can be generated using methods known in the art. Such methods were described, for example, in reference 12. Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

The expression constructs used in the systems of the invention may be non-bacterial expression constructs. This means that the construct can drive expression in a eukaryotic cell of viral RNA segments encoded therein, but it does not include components which would be required for propagation of the construct in bacteria. Thus the construct will not include a bacterial origin of replication (ori), and usually will not include a bacterial selection marker (e.g. an antibiotic resistance marker). Such expression constructs are described in reference 13 which is incorporated by reference.

The expression constructs may be prepared by chemical synthesis. The expression constructs may either be prepared entirely by chemical synthesis or in part. Suitable methods for preparing expression constructs by chemical synthesis are described, for example, in reference 13 which is incorporated by reference.

The expression constructs of the invention can be introduced into host cells using any technique known to those of skill in the art. For example, expression constructs of the invention can be introduced into host cells by employing electroporation, DEAE-dextran, calcium phosphate precipitation, liposomes, microinjection, or microparticle-bombardment.

Cells

The culture host for use in the present invention can be any eukaryotic cell that can produce the virus of interest. The invention will typically use a cell line although, for example, primary cells may be used as an alternative. The cell will typically be mammalian. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [14-15]. Suitable dog cells are e.g. kidney cells, as in the CLDK and MDCK cell lines.

Further suitable cells include, but are not limited to: CHO; 293T; BHK; MRC 5; PER.C6 [16]; FRhL2; WI-38; etc. Suitable cells are widely available e.g. from the American Type Cell Culture (ATCC) collection [17], from the Coriell Cell Repositories [18], or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PERC6 is available from the ECACC under deposit number 96022940.

Preferred cells for use in the invention are MDCK cells [19-20], derived from Madill Darby canine kidney. The original MDCK cells are available from the ATCC as CCL 34. It is preferred that derivatives of MDCK cells are used. Such derivatives were described, for instance, in reference 19 which discloses MDCK cells that were adapted for growth in suspension culture ('MDCK 33016' or '33016-PF', deposited as DSM ACC 2219; see also ref. 19). Furthermore, reference 21 discloses MDCK-derived cells that grow in suspension in serum free culture ('B-702', deposited as FERM BP-7449). In some embodiments, the MDCK cell line used may be tumorigenic. It is also envisioned to use non-tumorigenic MDCK cells. For example, reference 22 discloses non tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 23 discloses MDCK cells with high susceptibility to infection, including 'MDCK.5F1' cells (ATCC CRL 12042).

It is possible to use a mixture of more than one cell type to practise the methods of the present invention. However, it is preferred that the methods of the invention are practised with a single cell type e.g. with monoclonal cells. Preferably, the cells used in the methods of the present invention are from a single cell line. Furthermore, the same cell line may be used for reassorting the virus and for any subsequent propagation of the virus.

Preferably, the cells are cultured in the absence of serum, to avoid a common source of contaminants. Various serum-free media for eukaryotic cell culture are known to the person skilled in the art (e.g. Iscove's medium, ultra CHO medium (BioWhittaker), EX-CELL (JRH Biosciences)). Furthermore, protein-free media may be used (e.g. PF-CHO (JRH Biosciences)). Otherwise, the cells for replication can also be cultured in the customary serum-containing media (e.g. MEM or DMEM medium with 0.5% to 10% of fetal calf serum).

The cells may be in adherent culture or in suspension.

Conventional Reassortment

Traditionally, influenza viruses are reassorted by co-infecting a culture host, usually eggs, with a donor strain and a vaccine strain. Reassortant viruses are selected by adding antibodies with specificity for the HA and/or NA proteins of the donor strain in order to select for reassortant viruses that contain the vaccine strain's HA and/or NA proteins. Over several passages of this treatment one can select for fast growing reassortant viruses containing the vaccine strain's HA and/or NA segments.

The invention is suitable for use in these methods. It can be easier to use vaccine strains with a different HA and/or NA subtype compared to the donor strain(s) as this facilitates selection for reassortant viruses. It is also possible, however, to use vaccine strains with the same HA and/or NA subtype as the donor strain(s) and in some aspects of the invention this is preferred. In this case, antibodies with preferential specificity for the HA and/or NA proteins of the donor strain(s) should be available.

Virus Preparation

In one embodiment, the invention provides a method for producing influenza viruses comprising steps of (a) infecting a culture host with a reassortant virus of the invention; (b) culturing the host from step (a) to produce the virus; and optionally (c) purifying the virus obtained in step (b).

The culture host may be cells or embryonated hen eggs. Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines.

As mentioned above, cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. When culturing the infected cells (step ii), the cells are preferably cultured at a temperature of between 30° C. and 36° C. or between 32° C. and 34° C. or at 33° C. This is particularly preferred, as it has been shown that incubation of infected cells in this temperature range results in production of a virus that results in improved efficacy when formulated into a vaccine [24].

Oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8-25 \times 10^5$ cells/mL in the batch system or preferably about $5-20 \times 10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. In some embodiments, the cells may thus be adapted for growth in suspension.

The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

The culture host may be eggs. The current standard method for influenza virus growth for vaccines uses embryonated SPF hen eggs, with virus being purified from the egg contents (allantoic fluid). It is also possible to passage a virus through eggs and subsequently propagate it in cell culture and vice versa.

Vaccine

The invention utilises virus produced according to the method to produce vaccines.

Vaccines (particularly for influenza virus) are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce sub-virion preparations, including the 'Tween-ether' splitting process. Methods of splitting influenza viruses, for example are well known in the art e.g. see refs. 25-26, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza sub-unit vaccines.

Another form of inactivated antigen is the virosome [27] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The methods of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 28). Live virus vaccines include MedImmune's FLUMIST™ product (trivalent live virus vaccine).

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses [29,30]). Thus vaccines may include between 0.1 and 150 µg of HA per influenza strain, preferably between 0.1 and 50 µg e.g. 0.1-20 µg, 0.1-15 µg, 0.1-10 µg, 0.5-5 µg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

As well as being suitable for immunizing against inter-pandemic strains, the compositions of the invention are particularly useful for immunizing against pandemic or potentially-pandemic strains. The invention is suitable for vaccinating humans as well as non-human animals.

Other strains whose antigens can usefully be included in the compositions are strains which are resistant to antiviral therapy (e.g. resistant to oseltamivir [31] and/or zanamivir), including resistant pandemic strains [32].

Compositions of the invention may include antigen(s) from one or more (e.g. 1, 2, 3, 4 or more) influenza virus strains, including influenza A virus and/or influenza B virus provided that at least one influenza strain is a reassortant influenza strain of the invention. Compositions wherein at least two, at least three or all of the antigens are from reassortant influenza strains of the invention are also envisioned. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [33], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 34.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 µg/ml) mercurial material e.g. thiomersal-free [Error! Bookmark not defined, 35]. Vaccines containing no mercury are more preferred. An α-tocopherol succinate can be included as an alternative to mercurial compounds [Error! Bookmark not defined.]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [36], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any potential oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 37 & 38, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [39].

Adjuvants

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 µm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy(oxy-1,2-ethanediyl) groups, with octoxynol-9 (Triton X-100, or t-octylphenoxy-polyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [40].

Preferred emulsions have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [41-42], as described in more detail in Chapter 10 of ref. 43 and chapter 12 of ref. 44. The MF59 emulsion advantageously includes citrate ions e.g. 10 mM sodium citrate buffer.

An emulsion comprising squalene, a tocopherol, and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g. 0.90) as this can provide a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03') can be made by dissolving Tween 80 in PBS to give a 2% solution, then mixing 90 ml of this solution with a mixture of (5 g of DL α tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [45] e.g. in the ratios discussed above.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [46] (0.05-1% Thr-MDP, 5% squalane, 2.5% Pluronic L121 and 0.2% polysorbate 80). It can also be used without the Thr-MDP, as in the "AF" adjuvant [47] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [48]. The emulsion may also include one or more of: alditol; a cryoprotective agent (e.g. a sugar, such as dodecylmaltoside and/or sucrose); and/or an alkylpolyglycoside. The emulsion may include a TLR4 agonist [49]. Such emulsions may be lyophilized.

An emulsion of squalene, poloxamer 105 and Abil-Care [50]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 51, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 52, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [53].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [54].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [54].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs or birds, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [55]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [56-57], oral [58], intradermal [59,60], transcutaneous, transdermal [61], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. >50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

The various steps of the methods may be carried out at the same or different times, in the same or different geographical locations, e.g. countries, and by the same or different people or entities.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 62. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 63.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 62. A preferred alignment program is GCG Gap (Genetics Computer Group, Wisconsin, Suite Version 10.1), preferably using default parameters, which are as follows: open gap=3; extend gap=1.

BRIEF DESCRIPTION OF THE DRAWINGS

In FIG. 12, the solid lines with the triangle markers represent results with the #19 backbone. The dotted lines with square markers represent results with the PR8-X backbone. The x-axis shows the hours post infection and the y-axis shows the virus titer (IU/ml).

FIG. 18 is an alignment of the M1 viral segment of A/New Caledonia/20/99 (SEQ ID NO: 33) and 105p30 (SEQ ID NO: 45).

MODES FOR CARRYING OUT THE INVENTION

Development of New Donor Strains

In order to provide high-growth donor strains, the donor strain A/Puerto Rico/8/34 is passaged in MDCK 33016 cells five times. Using this method, the inventors were able to obtain the strain PR8-X which shows improved growth characteristics compared with the original strain.

The 105p30 influenza donor strain was provided by isolating an A/New Caledonia/20/1999 influenza virus from a clinical isolate in MDCK 33016 cells and passaging the virus 30 times. The resulting strain has a M segment with lysine in the position corresponding to amino acid 95 of SEQ ID NO: 33 when aligned to SEQ ID NO: 33.

Growth Characteristics of Wt PR8 and PR8-X Viruses

In order to compare the growth characteristics of PR8-X and wt PR8 donor strains, the viral titre of these virus strains is measured in MDCK cells by focus-forming assays and hemagglutination assays.

Focus-Forming Assays (FFA)

For the FFA, uninfected MDCK cells are plated at a density of $1.8 \times 10^4$ cells/well in 96 well plates in 100 µl of DMEM with 10% FCS. The next day, medium is aspirated and cells are infected with viruses in a volume of 50 µl (viruses diluted in DMEM+1% FCS). The cells are incubated at 37° C. until the next day.

At several time points after infection, the medium is aspirated and the cells washed once with PBS. 50 µl of ice-cold 50%/50% acetone-methanol is added to each well followed by incubation at −20° C. for 30 minutes. The acetone mix is aspirated and the cells washed once with PBST (PBS+0.1% Tween). 50 µl of 2% BSA in PBS is added to each well followed by incubation at room temperature (RT) for 30 minutes. 50 µl of a 1:6000 dilution of anti-NP is added in blocking buffer followed by incubation at RT for 1 hours. The antibody solution is aspirated and the cells washed three times with PBST. Secondary antibody (goat anti mouse) is added at a dilution 1:2000 in 50 µl blocking buffer and the plate is incubated at RT for 1 hours. The antibody solution is aspirated and the cells washed three times with PBST. 50 µl of KPL True Blue is added to each well and incubated for 10 minutes. The reaction is stopped by aspirating the True-Blue and washing once with $dH_2O$. The water is aspirated and the cells are left to dry.

Figure 1:
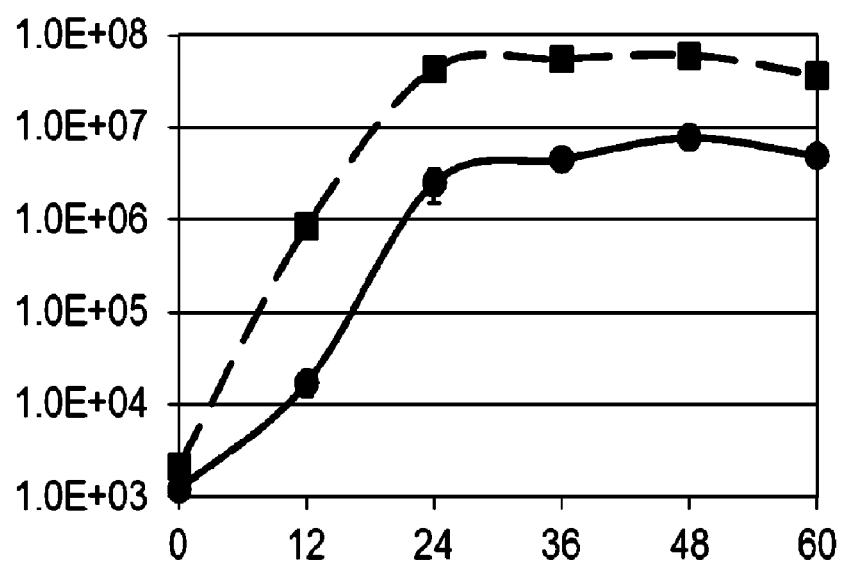
FIG. 1 illustrates virus titers (by Focus-Formation assay (FFA); (A) and HA titers (by Red Blood Cell Hemagglutination assay; (B) at different times post-infection of wt PR8 and PR8-X viruses grown in MDCK cells. The solid line in (A) and hatched columns in (B) represent results with wild-type PR8. The dotted line in (A) and empty columns in (B) represent results with wild-type PR8-X. The x-axis shows the hours post infection and the y-axis in (A) and (B) shows the virus titer (IU/ml) and HA titre, respectively.
Figure 1:
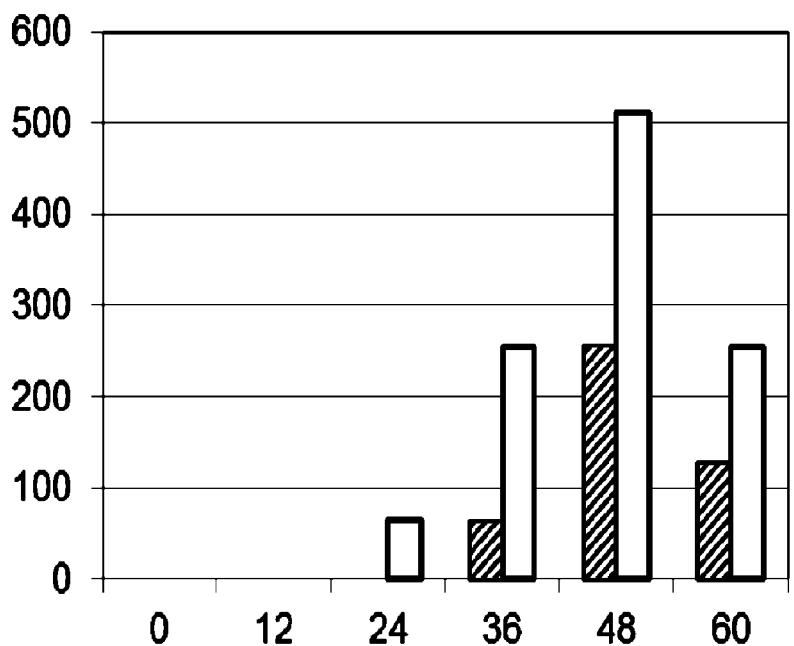
Figure 2:
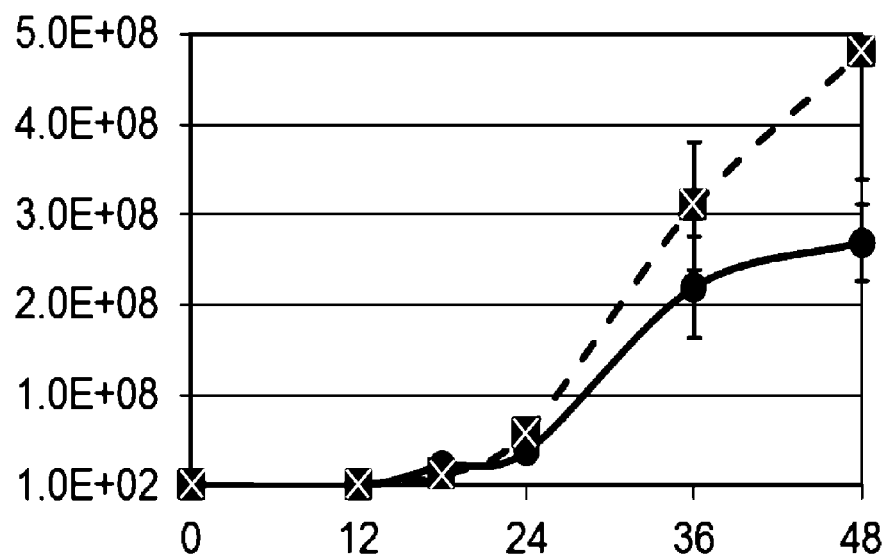
FIG. 2 illustrates virus titers (by FFA; (A) and HA titers (by Red Blood Cell Hemagglutination assay; (B) at different times post-infection of reverse genetics derived PR8 and PR8-X viruses grown in MDCK cells. The solid line in (A) and hatched columns in (B) represent results with PR8. The dotted line in (A) and empty columns in (B) represent results with RG-derived PR8-X. The x-axis shows the hours post infection and the y-axis in (A) and (B) shows the virus titer (IU/ml) and HA titre, respectively.
Figure 2:
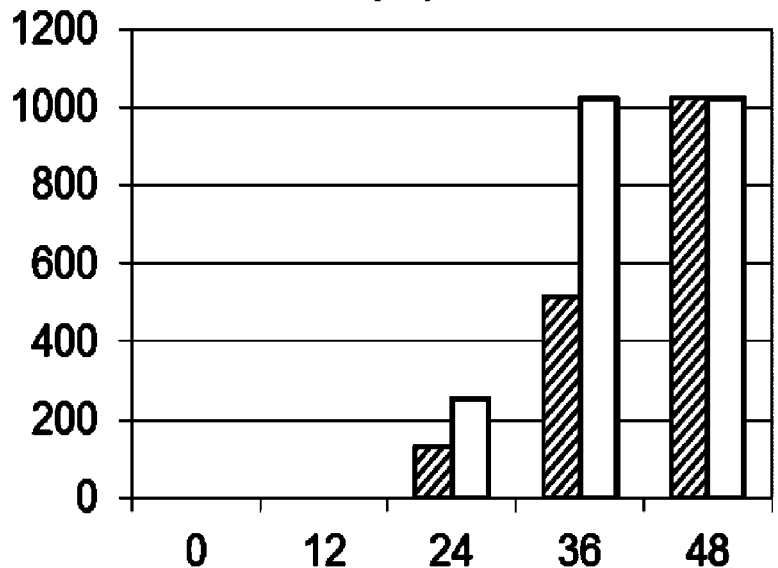
Figure 3:
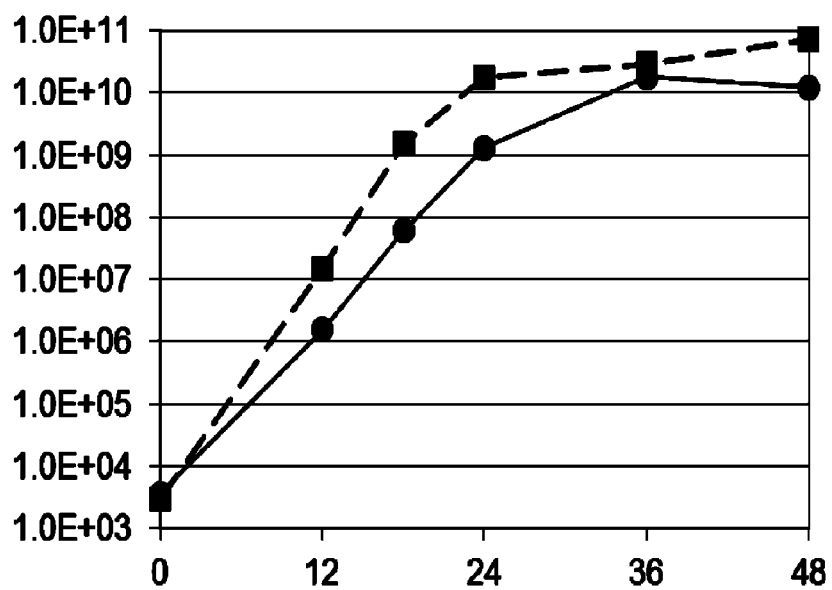
FIG. 3 compares virus titers (by FFA; (A) and HA titers (by Red Blood Cell Hemagglutination assay; (B)—at different times post-infection in MDCK cells of reverse genetics-derived 6:2 reassortant viruses made with either PR8 or PR8-X backbone segments which contain the HA and NA segments from PR8-X. The solid line in (A) and hatched columns in (B) represent results with the PR8 backbone. The dotted line in (A) and empty columns in (B) represent results with the PR8-X backbone. The x-axis shows the hours post infection and the y-axis in (A) and (B) shows the virus titer (IU/ml) and HA titre, respectively.
Figure 3:
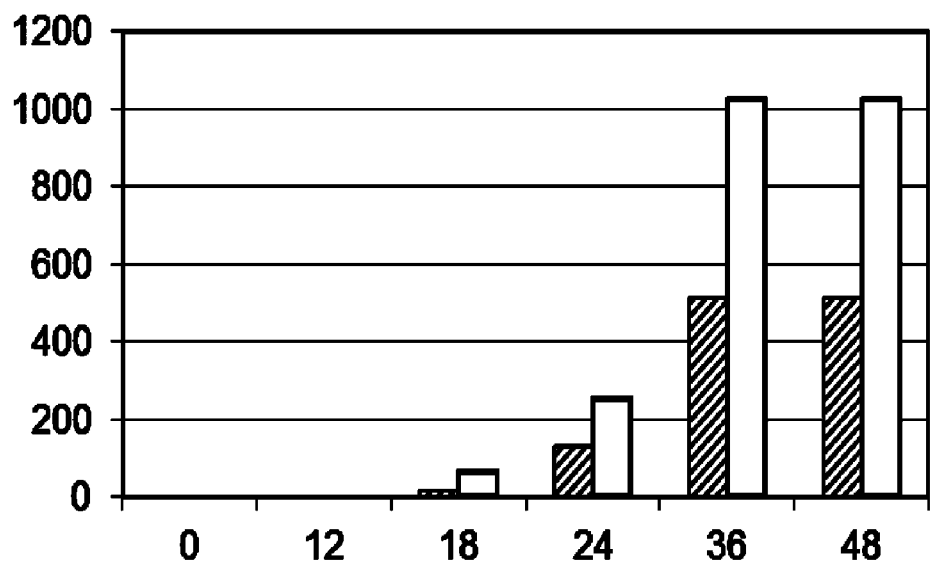

The results (FIG. 1) show that the PR8-X strain can grow to higher titres in the same time frame compared to the wt PR8 strain from which it is derived.

Figure 4:
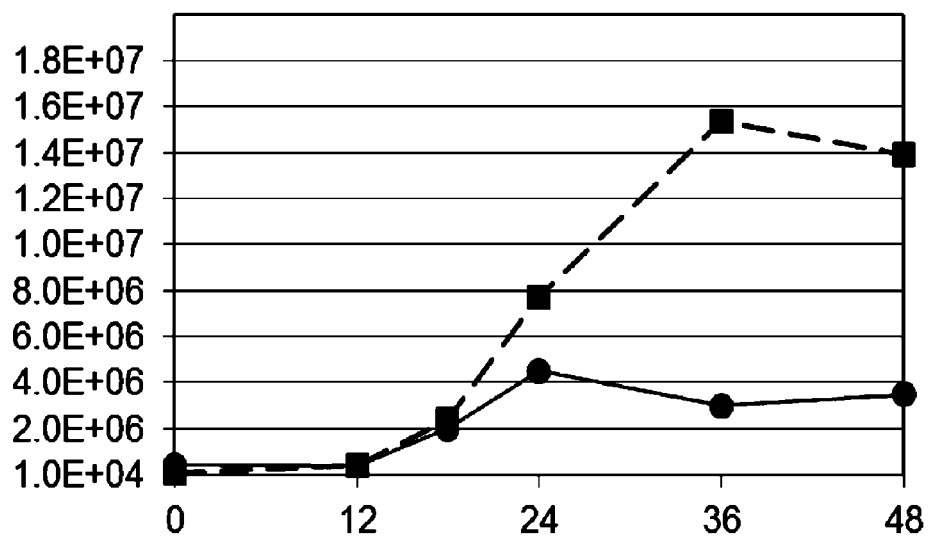
FIG. 4 compares virus titers by FFA (A) and HA titers (by Red Blood Cell Hemagglutination assay; (B) at different times post-infection in MDCK cells of reverse genetics-derived 6:2 reassortant viruses made with either wt PR8 or PR8-X backbone segments which contain the HA and NA segments from a pandemic H1 strain (strain 1). The solid line in (A) and hatched columns in (B) represent results with the wt PR8 backbone. The dotted line in (A) and empty columns in (B) represent results with the PR8-X backbone. The x-axis shows the hours post infection and the y-axis in (A) and (B) shows the virus titer (IU/ml) and HA titre, respectively.
Figure 4:
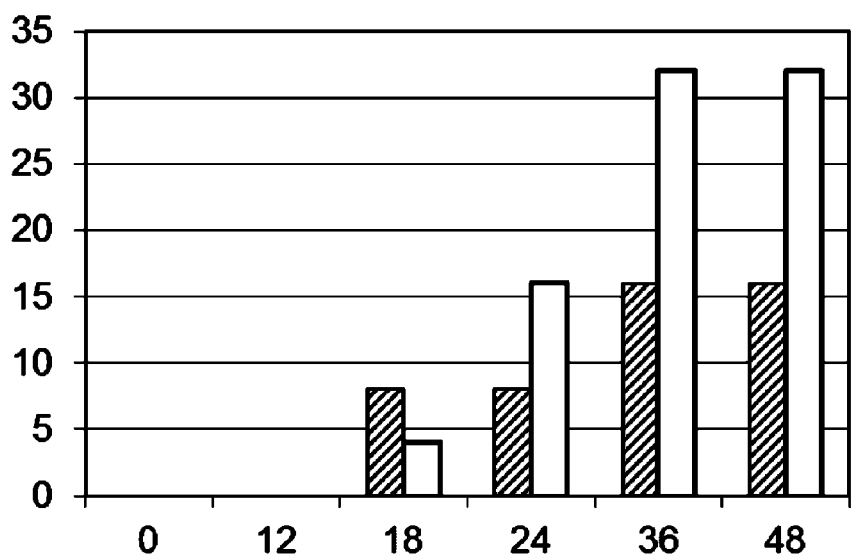
Figure 5:
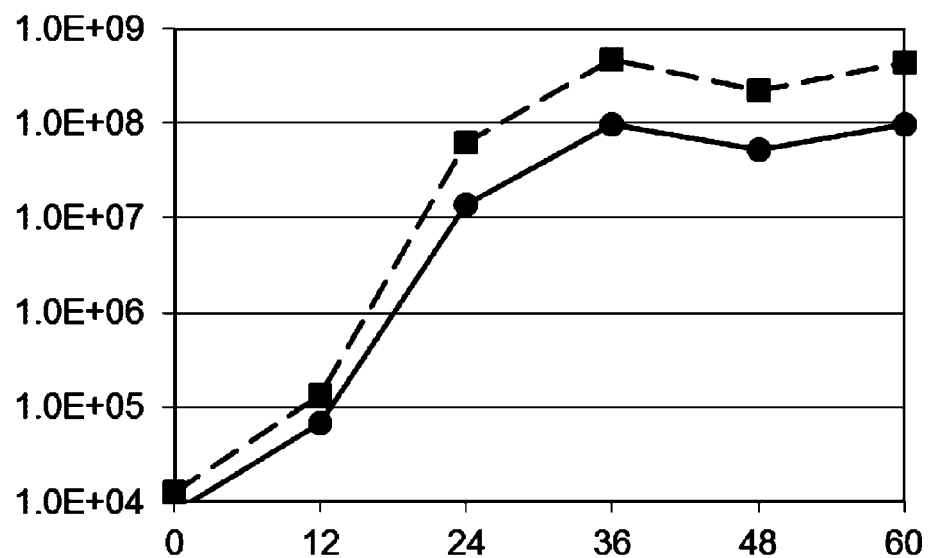
FIG. 5 compares virus titers by a focus-formation assay (FFA) (A) and HA titers (B) at different times post-infection in MDCK cells of reverse genetics-derived 6:2 reassortant viruses made with either PR8 or PR8-X backbone segments which contain the HA and NA segments from 105p30. The solid line in (A) and hatched columns in (B) represent results with the wt PR8 backbone. The dotted line in (A) and empty columns in (B) represent results with the PR8-X backbone. The x-axis shows the hours post infection and the y-axis shows the virus titer (IU/ml).
Figure 5:
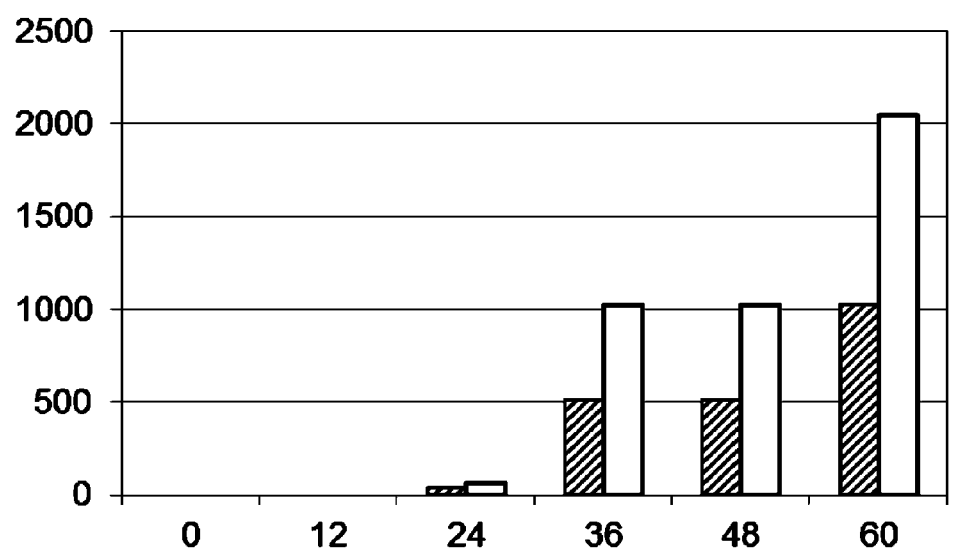

Growth Characteristics of Reassortant Viruses Containing PR8-X or Wt PR8 Backbones In order to test the suitability of the PR8-X strain as a donor strain for virus reassortment, reassortant viruses are produced by reverse genetics which contain the HA and NA proteins from a pandemic H1 strain and the other viral segments from either PR8-X or PR8. The viral titres of these reassortant viruses are determined by FFA and HA assays as described above. The results are shown in FIG. 4.

The results indicate that reassortant viruses which contain viral segments from PR8-X grow faster in MDCK cells compared to reassortant viruses containing viral segments from the PR8/34 strain.

Growth Characteristics of 105p30 Strain Compared with PR8-X

Figure 6:
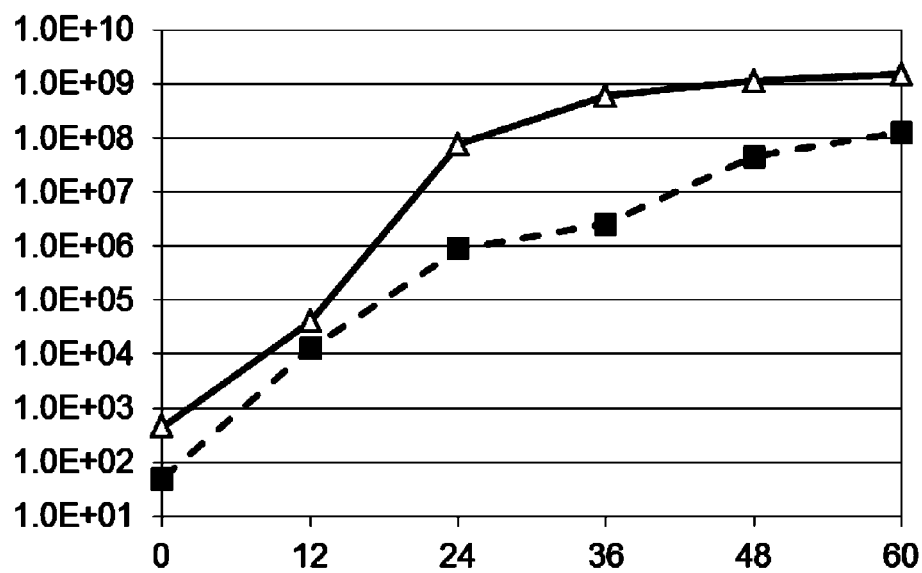
FIG. 6 illustrates virus titers by a focus-formation assay (FFA) at different times post-infection of wild-type PR8-X and 105p30 viruses (A) or reverse genetics-derived PR8-X and 105p30 viruses (B) grown in MDCK cells. In (A) and (B), the solid lines represent results with 105p30. The dotted lines represent results with PR8-X. The x-axis shows the hours post infection and the y-axis in (A) and (B) shows the virus titer (IU/ml) and HA titre, respectively.
Figure 6:
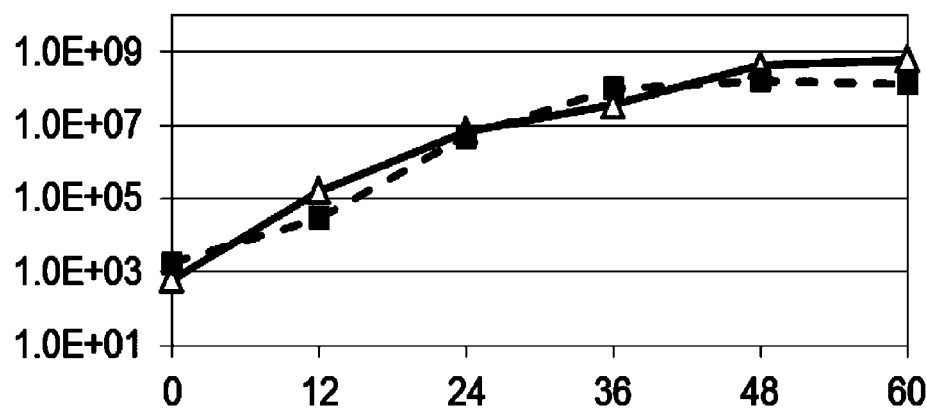

MDCK cells are infected with 105p30 and PR8-X at a moi of $10^{-3}$ and samples are taken at several time points after infection. The titre is determined by a FFA assay. The results show that 105p30 grows even faster in MDCK cells compared to PR8-X (FIG. 6).

Figure 7:
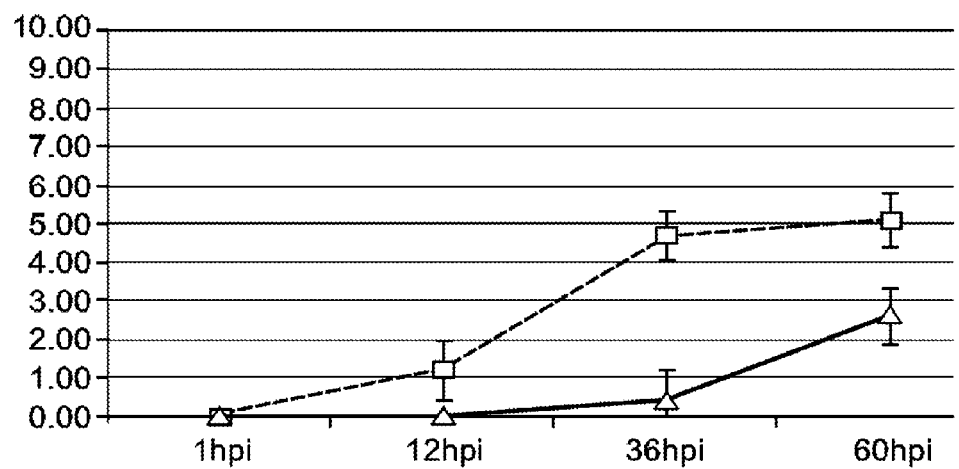
FIG. 7 shows the growth characteristics of reassortant viruses containing the backbone segments of the wt PR8 strain (line with triangles) or 105p30 strain (line with squares) and the HA and NA segments of a pandemic H1 influenza strain (strain 2). The x-axis in (A) and (B) indicates the hours post infection. The y-axis in (A) shows the titre Log 10 in FFU per mL. The y-axis in (B) shows the titre log 10 in virus particles per mL.
Figure 7:
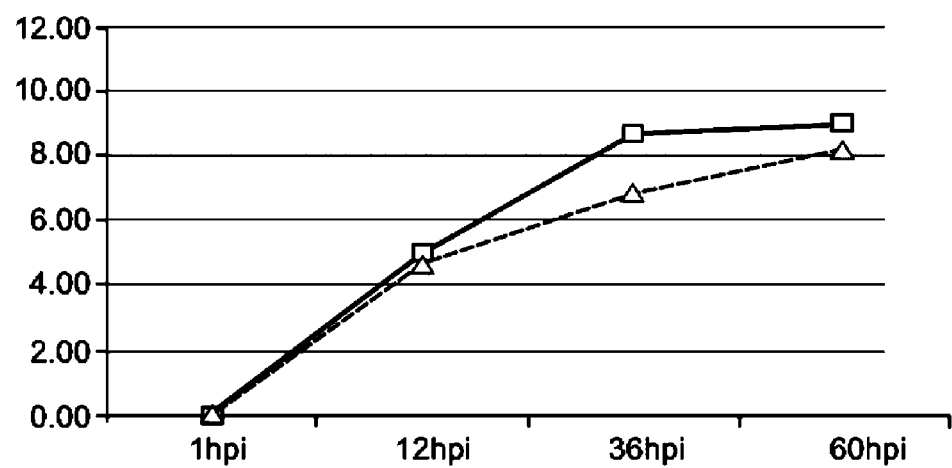
Figure 8:
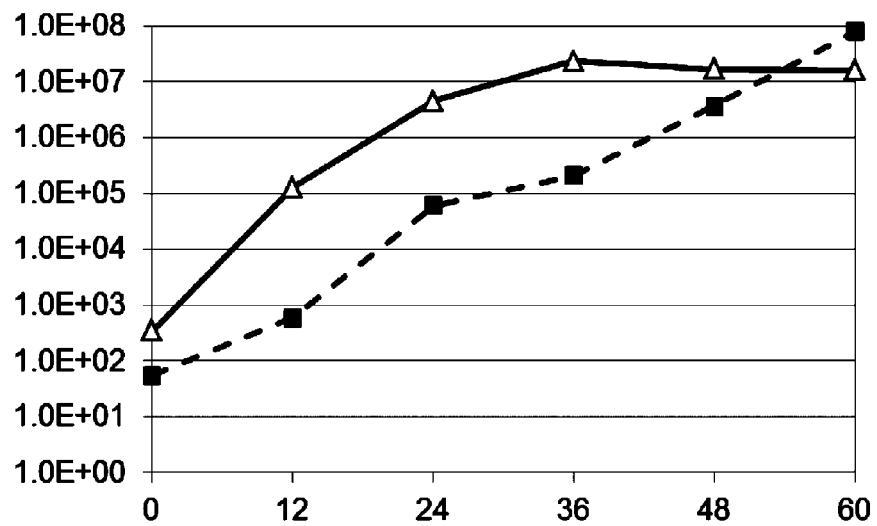
FIG. 8 compares virus titers by a focus-formation assay (FFA) at different times post-infection in MDCK cells of reverse genetics-derived 6:2 reassortant viruses made with either 105p30 or PR8-X backbone segments which contain the HA and NA segments from (A) a H1 strain (strain 1) or (B) a pandemic H1 strain (strain 2). The solid lines represent results with the 105p30 backbone. The dotted lines represent results with the PR8-X backbone. The x-axis shows the hours post infection and the y-axis shows the virus titer (IU/ml).
Figure 8:
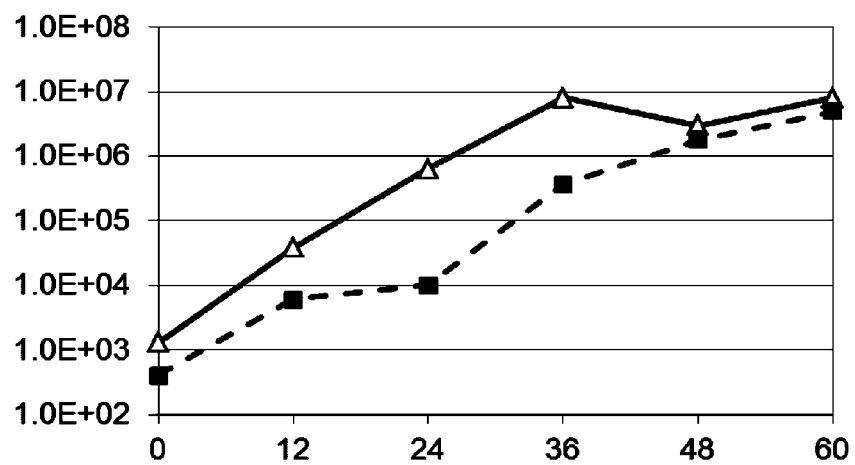

Growth Characteristics of Reassortant Viruses Containing 105p30 or wt PR8 Backbones In order to test the suitability of the 105p30 strain as a donor strain for virus reassortment, reverse genetics is used to produce reassortant viruses that contain the HA and NA segments from a pandemic H1 influenza strain and the backbone segments either from the 105p30 or the wt PR8 strain. MDCK cells are infected with the reassortant viruses at a moi of $10^{-3}$ and samples are taken 1 hour, 12 hours, 36 hours and 60 hours after infection. The titres are determined either by focus-forming assays or by determining the virus particles by real-time detection PCR. The reassortant viruses that contain the backbone segments from the 105p30 strain grow faster than the viruses that are reassorted with the backbone segments of the wt PR8 strain. This shows that the 105p30 strain is a good donor strain for producing fast-growing reassortant viruses (FIG. 7).

Rescue of Influenza Viruses Using Backbone Segments from Two Donor Strains

The rescue efficiency of reassortant influenza viruses containing the HA and NA segments from a H3 influenza virus and backbone segments from the 105p30 and the PR8-X donor strains is tested in MDCK cells. The reassortant influenza viruses contain backbone segments of the 105p30 and the PR8-X donor strains, as indicated in the following table:

TABLE 1

| Backbone # | FB1 | PB2 | PA | NP | M | NS |
|---|---|---|---|---|---|---|
| 1 | PR8-X | PR8-X | PR8-X | 105p30 | 105p30 | 105p30 |
| 2 | PR8-X | PR8-X | 105p30 | PR8-X | 105p30 | 105p30 |
| 3 | PR8-X | PR8-X | 105p30 | 105p30 | PR8-X | 105p30 |
| 4 | PR8-X | PR8-X | 105p30 | 105p30 | 105p30 | PR8-X |
| 5 | PR8-X | 105p30 | PR8-X | PR8-X | 105p30 | 105p30 |
| 6 | PR8-X | 105p30 | PR8-X | 105p30 | PR8-X | 105p30 |
| 7 | PR8-X | 105p30 | PR8-X | 105p30 | 105p30 | PR8-X |
| 8 | PR8-X | 105p30 | 105p30 | PR8-X | PR8-X | 105p30 |
| 9 | PR8-X | 105p30 | 105p30 | PR8-X | 105p30 | PR8-X |
| 10 | PR8-X | 105p30 | 105p30 | 105p30 | PR8-X | PR8-X |
| 11 | 105p30 | PR8-X | PR8-X | PR8-X | 105p30 | 105p30 |
| 12 | 105p30 | PR8-X | PR8-X | 105p30 | PR8-X | 105p30 |
| 13 | 105p30 | PR8-X | PR8-X | 105p30 | 105p30 | PR8-X |
| 14 | 105p30 | PR8-X | 105p30 | PR8-X | 105p30 | PR8-X |
| 15 | 105p30 | PR8-X | 105p30 | PR8-X | PR8-X | 105p30 |
| 16 | 105p30 | PR8-X | 105p30 | 105p30 | PR8-X | PR8-X |
| 17 | 105p30 | 105p30 | PR8-X | PR8-X | PR8-X | 105p30 |

TABLE 1-continued

| Backbone # | PB1 | PB2 | PA | NP | M | NS |
|---|---|---|---|---|---|---|
| 18 | 105p30 | 105p30 | PR8-X | PR8-X | 105p30 | PR8-X |
| 19 | 105p30 | 105p30 | PR8-X | 105p30 | PR8-X | PR8-X |
| 20 | 105p30 | 105p30 | 105p30 | PR8-X | PR8-X | PR8-X |

Reassortant influenza viruses which contain a backbone according to number 3, 4, 10, 11, 14 and 16-20 are rescuable. Influenza viruses which contain backbones number 3, 4, 10, 11 or 16 achieve viral titres of less than $10^2$ IU/mL. Influenza viruses containing backbone numbers 17 and 18 achieve viral titres between $10^2$ and $10^6$ IU/mL and influenza viruses having backbone numbers 19 and 20 even achieve titres of more than $10^6$ IU/mL.

These data show that influenza viruses in which the PB 1 and PB2 segments come from the same influenza donor strain can show a higher rescue efficiency compared with influenza viruses in which these segments come from different influenza donor strains.

Growth Characteristics of Reassortant Influenza Viruses Containing Backbone Segments from Two Donor Strains Reassortant influenza strains are created which contain backbone numbers 17, 18, 19 and 20 (as shown in table 1 above) and the HA and NA segments from a H3 influenza strain (strain 1). As controls, the equivalent wildtype H3 influenza virus, and a reassortant influenza virus comprising the same HA and NA segments and all backbone segments from PR8-X are used.

Furthermore, reassortant influenza strains are produced which contain backbone numbers 17 and 19 and the HA and NA segments from either a second H3 influenza (strain 1) virus or a pandemic H1 influenza virus (strain 3). As controls for the H3 strain, the equivalent wildtype H3 (strain 2) influenza virus, and a reassortant influenza virus comprising the same HA and NA segments and all backbone segments from PR8-X is used. For the pandemic H1 influenza virus a reassortant influenza virus comprising the same HA and NA segments and all backbone segments from PR8-X is used.

Figure 13:
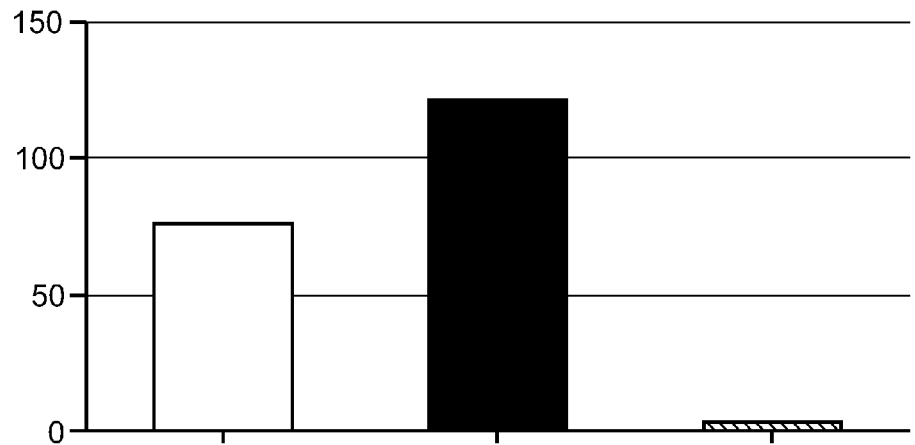
FIG. 13 compares HA yields (by lectin-capture ELISA) at 60 hr post-infection in MDCK cells of different 6:2 reassortant viruses made with either the chimeric #19 (empty columns) or PR8-X backbone (solid columns) plus the HA and NA segments from the following strains: (A) a pandemic H1 strain (strain 2), (B) a pandemic H1 strain (strain 4). Corresponding 6:2 reassortant viruses made by classical reassortment ("classical") with the wt PR8 backbone were included as controls (hatched columns). The y-axis shows the HA content in µg per mL.
Figure 13:
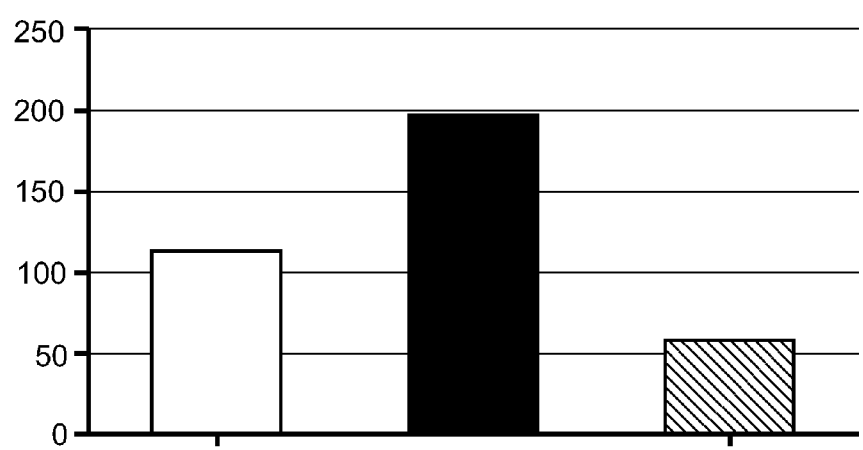
Figure 14:
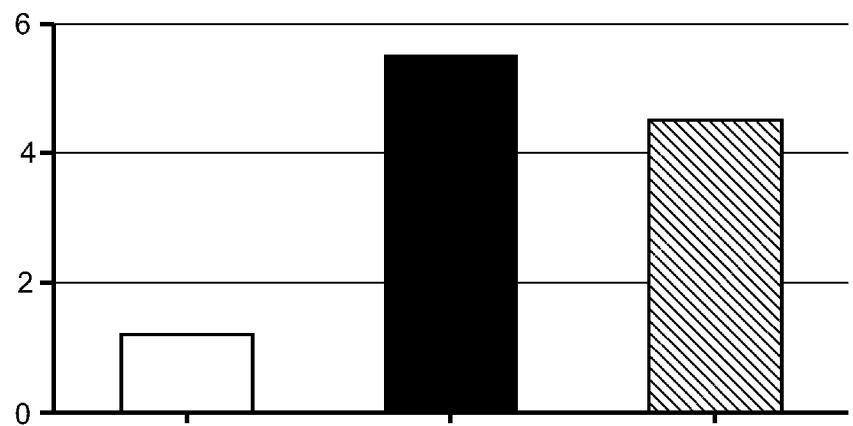
FIG. 14 compares HA yields (by lectin-capture ELISA) at 60 hr post-infection in MDCK cells of different 6:2 reassortant viruses made with either the chimeric #19 (empty columns) or PR8-X backbone (solid columns) plus the HA and NA segments from the following strains: (C) a H3 strain (strain 1), or (D) a H3 strain (strain 2). Corresponding 6:2 reassortant viruses made by classical reassortment ("classical") with the wt PR8 backbone were included as controls (hatched columns) The y-axis shows the HA content in µg per mL.
Figure 14:
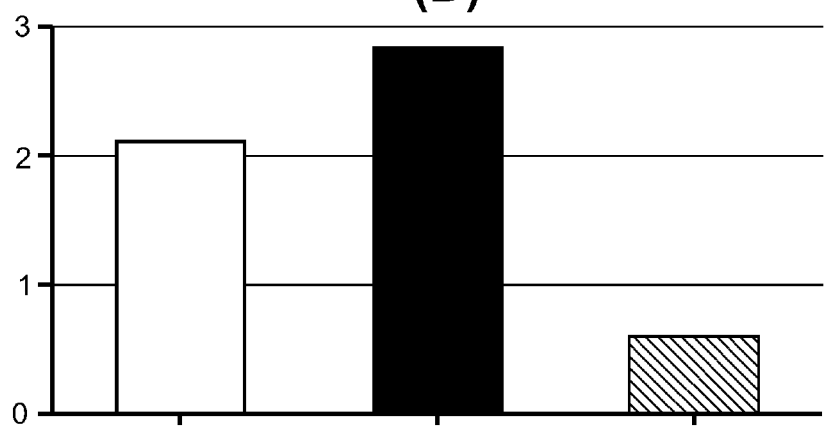
Figure 15:
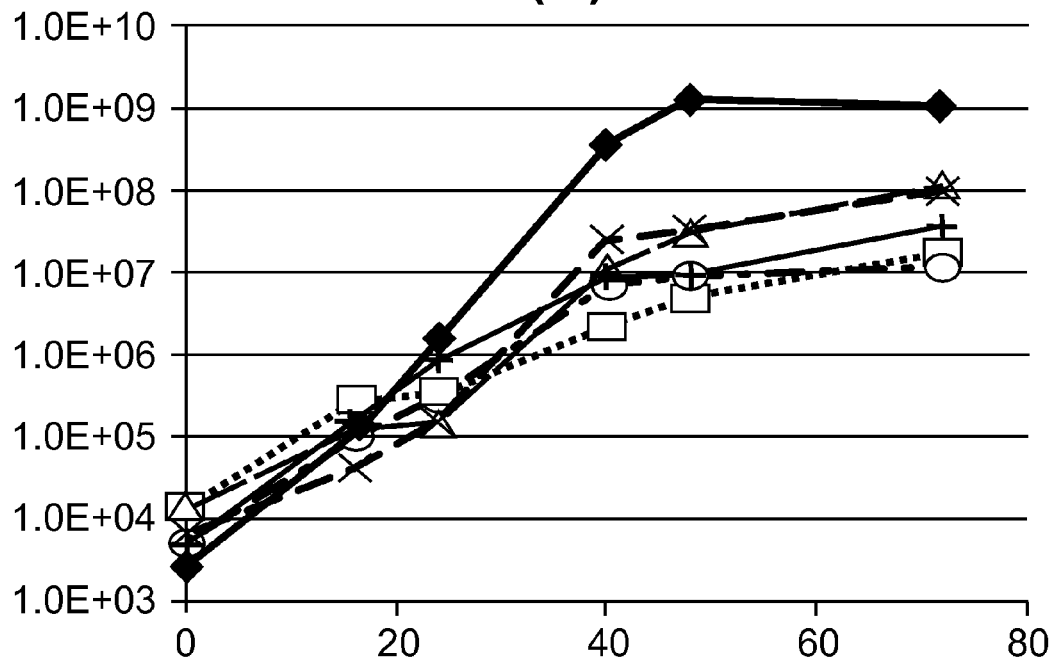
FIG. 15 shows the growth curves of reassortant influenza viruses. (A) shows growth curves of reassortant influenza viruses comprising backbones 17, 18, 19 and 20 (as shown in table 1; line with diamonds, squares, triangles and crosses, respectively), a control comprising the same HA and NA segments from a H3 influenza strain (strain 1) but all backbone segments from PR8-X (line with circles) and the equivalent wildtype strain (line with plus sign). The x axis indicates the hours post infection (hpi) and the y-axis shows IU/mL. (B) shows the growth curve of reassortant influenza viruses comprising backbones 17 and 19 (line with diamonds and triangles, respectively) and the HA segments from a H3 influenza strain (strain 3), a control comprising the same HA and NA segments but all backbone segments from PR8-X (line with plus sign) and the equivalent wildtype strain (line with circles).
Figure 15:
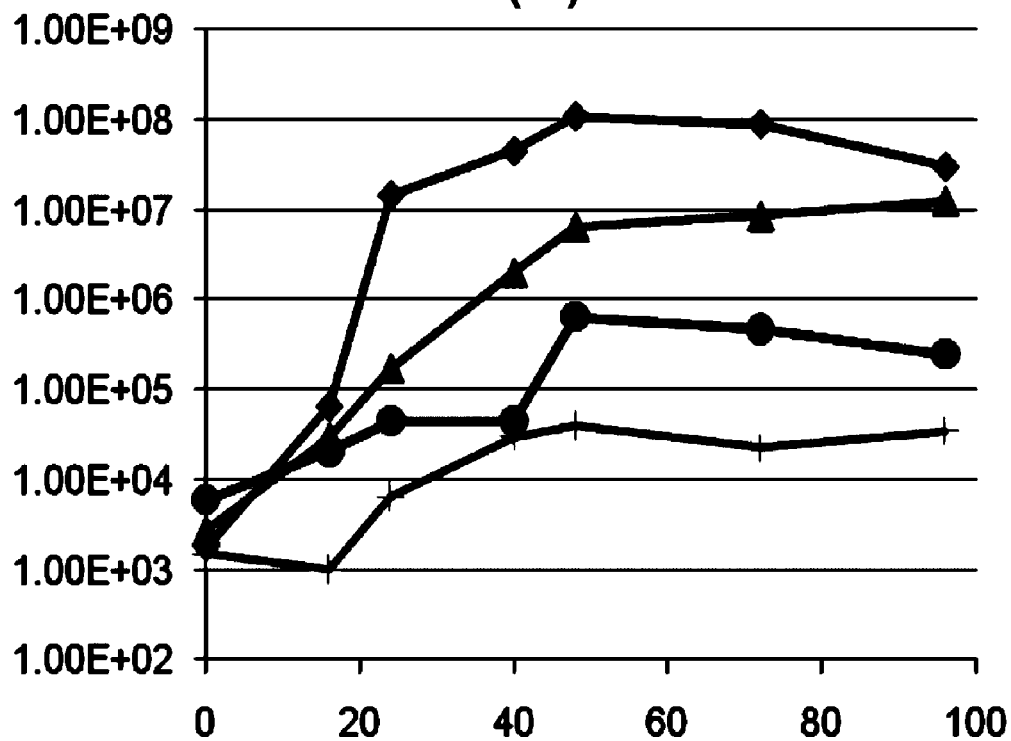

The reassortant influenza viruses and the control viruses are grown in MDCK cells and the viral titre is measured by FFA at different time points. For the reassortant H3 viruses (strain 1) containing backbones 17, 19 and 20, and the H3 influenza viruses (strain 3) containing backbones 17 and 19, the influenza viruses containing backbone segments from two donor strains grow to higher titres compared with the wildtype virus and the reassortant virus which contains backbone segments from only a single donor strain (see FIG. 13, FIG. 14 and FIG. 15(A)).

Figure 9:
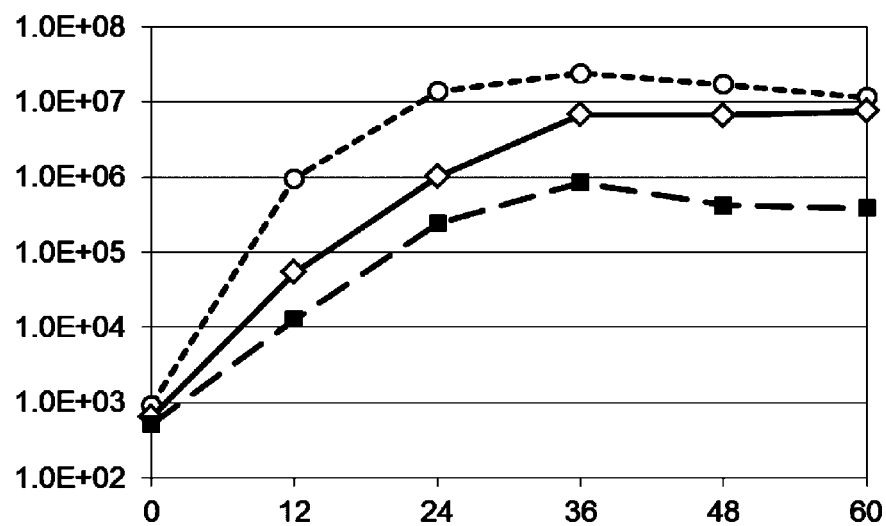
FIG. 9 compares virus titers by a focus-formation assay (FFA) at different times post-infection in MDCK cells of reverse genetics-derived 6:2 reassortant viruses made with either the #17, #19, or PR8-X backbone in combination with the HA and NA segments from (A) a pandemic H1 strain (strain 3) or (B) a H3 (strain 1). In (A) and (B), the dotted lines with the circle markers represent results with the #17 backbone. The solid lines with diamond markers represent results with the #19 backbone. The dotted lines with square markers represent results with the PR8-X backbone. The x-axis shows the hours post infection and the y-axis shows the virus titer (IU/ml).
Figure 9:
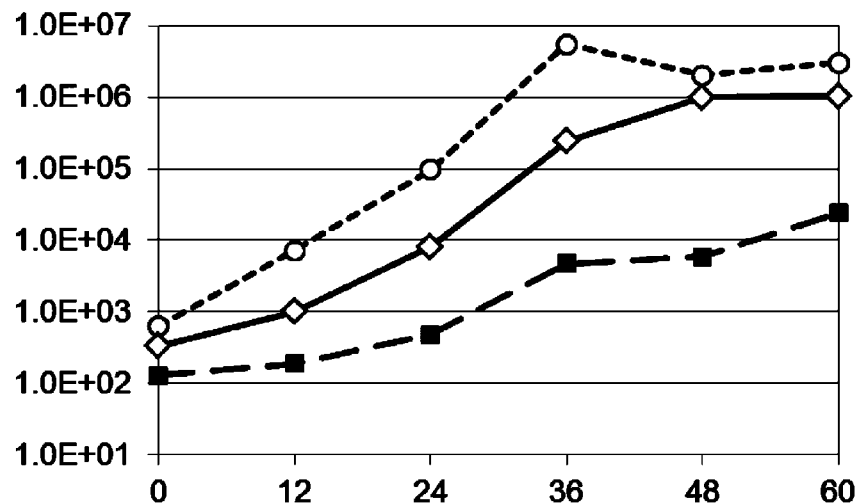

For the pandemic H1 influenza virus, the reassortant influenza strains containing backbones 17 and 19 grow to higher titres compared with the control which contained all backbone segments from PR8-X (see FIG. 9).

The data show that reassortant influenza viruses which contain backbone segments from two different donor strains can show improved growth rates compared with reassortant influenza viruses which contain backbone segments from only a single donor strain.

Figure 10:
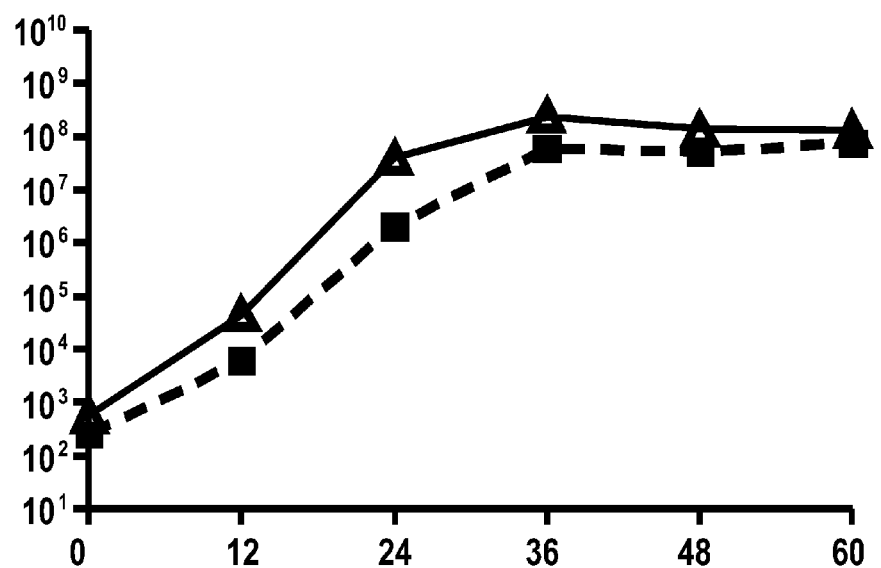
FIG. 10 compares virus titers by a focus-formation assay (FFA) at different times post-infection in MDCK cells of a panel of different reverse genetics-derived 6:2 reassortant viruses made with either the chimeric #19 or PR8-X backbone plus the HA and NA segments from the following strains: (A) a pandemic H1 strain (strain 2), (B) a pandemic H1 strain (strain 4)-In (A) and (B), the solid lines with the triangle markers represent results with the #19 backbone. The dotted lines with square markers represent results with the PR8-X backbone. The x-axis shows the hours post infection and the y-axis shows the virus titer (IU/ml).
Figure 10:
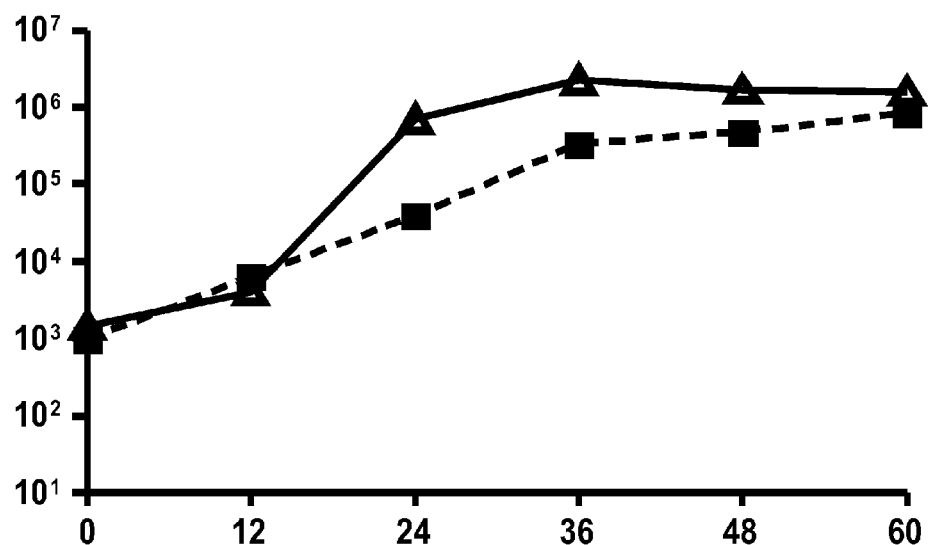
Figure 11:
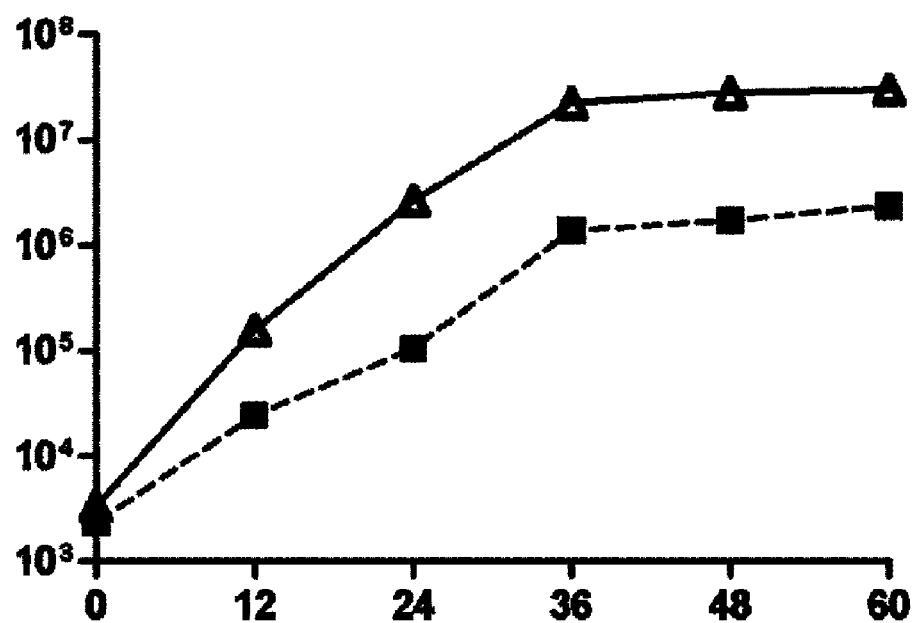
FIG. 11 compares virus titers by a focus-formation assay (FFA) at different times post-infection in MDCK cells of a panel of different reverse genetics-derived 6:2 reassortant viruses made with either the chimeric #19 or PR8-X backbone plus the HA and NA segments from the following strains: (C) a H1 strain (strain 2), (D) a H1 strain (strain 3). In (C) and (D), the solid lines with the triangle markers represent results with the #19 backbone. The dotted lines with square markers represent results with the PR8-X backbone. The x-axis shows the hours post infection and the y-axis shows the virus titer (IU/ml).
Figure 11:
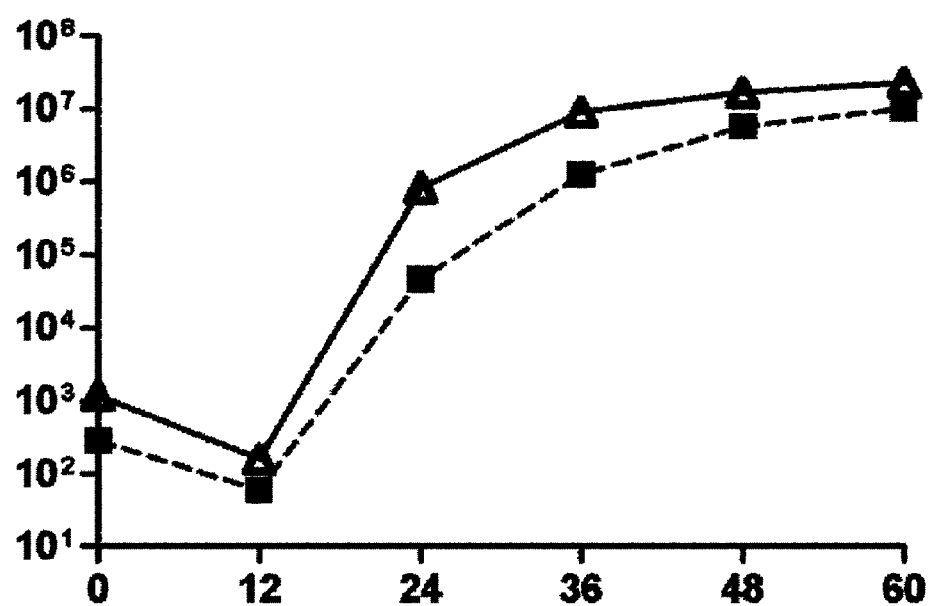
Figure 12:
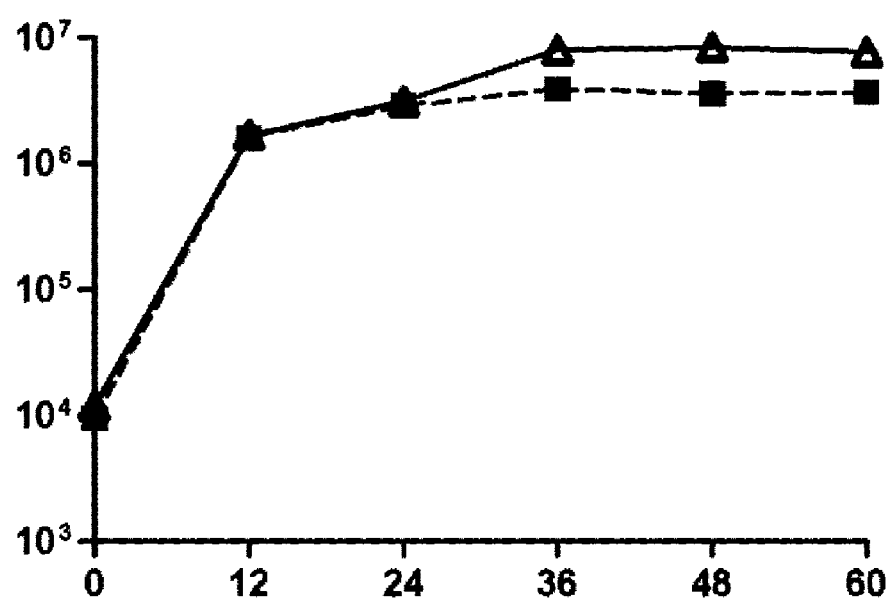
FIG. 12 compares virus titers by a focus-formation assay (FFA) at different times post-infection in MDCK cells of a panel of different reverse genetics-derived 6:2 reassortant viruses made with either the chimeric #19 or PR8-X backbone plus the HA and NA segments from the following strain: a H3 strain (strain 2).

The experiments were also repeated using reassortant influenza viruses which contain backbone 19 or the backbone segments from PR8-X in combination with the HA and NA segments from four different H1 strains or a H3 strain. The results are shown in FIG. 10, FIG. 11, and FIG. 12.

Reassortant Influenza Viruses with Backbone Segments from Two Different Donor Strains Give Higher Yields To test whether reassortant influenza viruses containing backbone segments from two different influenza donor strains can also provide higher yields, the HA yield of the reassortant strains is tested by HA-ELISA. To this end, the same reassortant influenza viruses as described above containing backbone #19 and the HA/NA segments of the H3 (strain 2) and H1 influenza strains are used. As controls, the equivalent wildtype influenza viruses and reassortant influenza viruses comprising the same HA and NA segments and all backbone segments from PR8-X are used. In addition, the viral titres are confirmed with a FFA assay.

Figure 16:
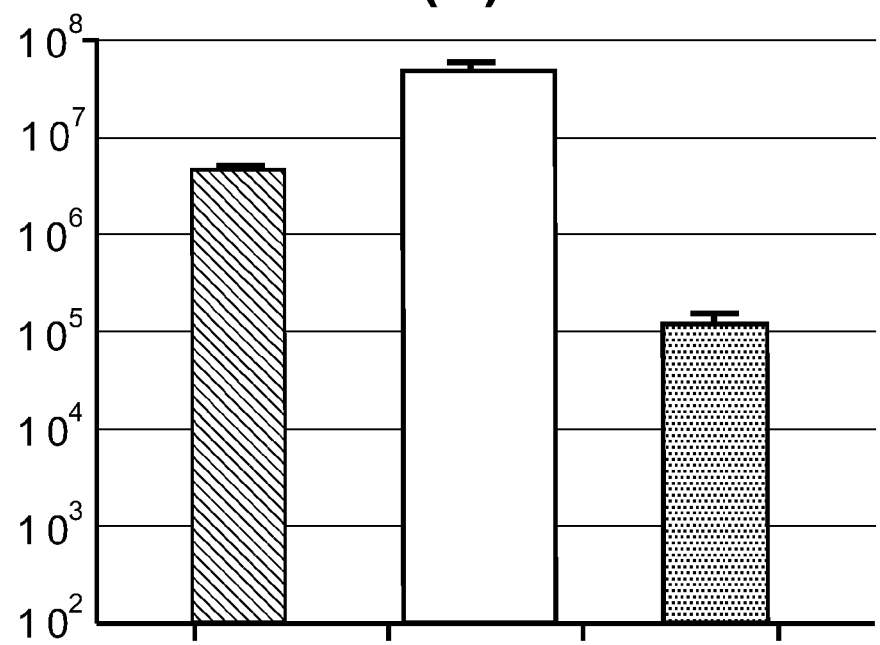
FIG. 16 shows the results of a FFA (A) and HA-ELISA (B) assay using reassortant influenza viruses comprising backbone 19 (open box), PR8-X backbone (hatched box) and the wildtype influenza virus (dotted box). (A) and (B) show the results with a H1 influenza strain (strain 2). The y axis in (A) indicates the virus titre in IU/mL and the y axis in (B) indicates HA in µg/mL.
Figure 16:
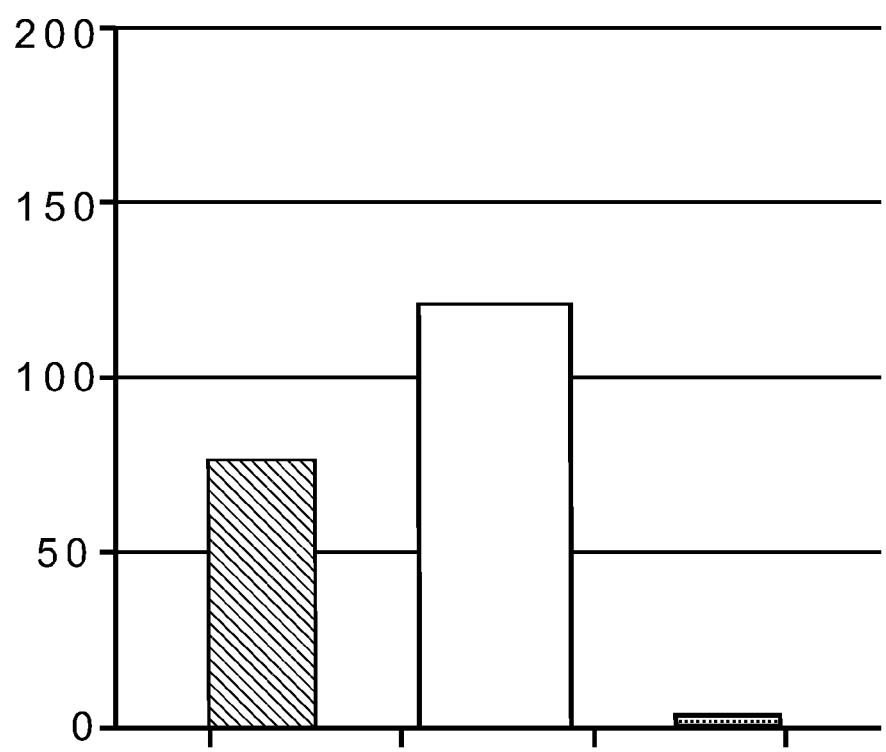
Figure 17:
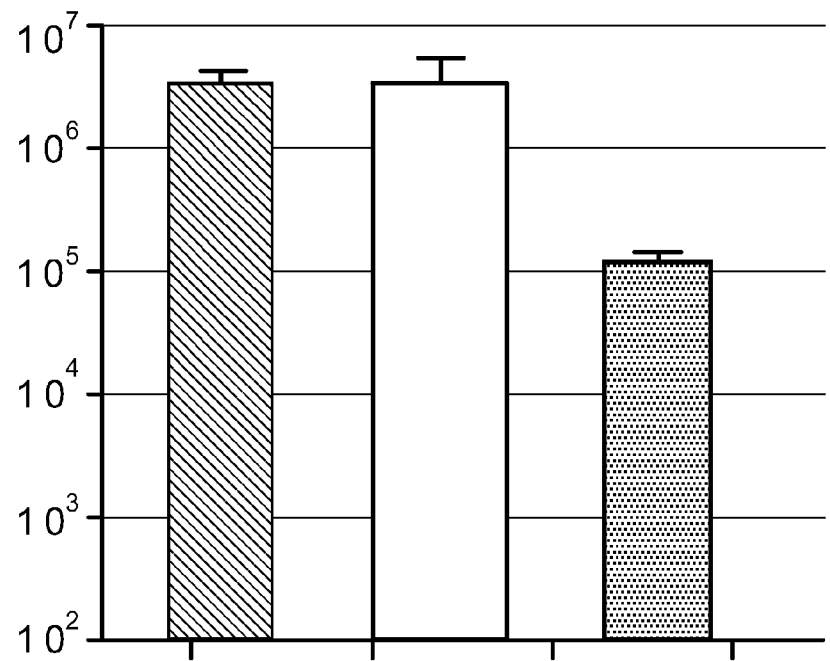
FIG. 17 shows the results of a FFA (C) and HA-ELISA (D) assay using reassortant influenza viruses comprising backbone 19 (open box), PR8-X backbone (hatched box) and the wildtype influenza virus (dotted box). (C) and (D) show the results with a H3 influenza virus strain. The y axis in (C) indicates the virus titre in IU/mL and the y axis in (D) indicates HA in µg/mL.
Figure 17:
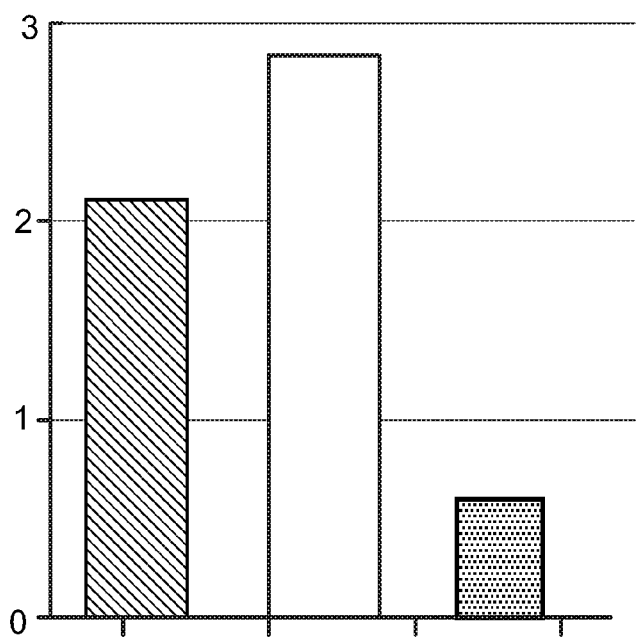

The results confirm that the reassortant influenza strains which contain backbone segments from two different donor strains can grow to higher yields compared with influenza viruses which contained all backbones from PR8-X (see FIG. 16 (A) and FIG. 17 (C)). Furthermore, reassortant influenza viruses comprising backbone segments from two donor strains also give higher HA yields (see FIG. 16 (B) and FIG. 17 (D)).

These data show that reassortant influenza viruses which contain backbone segments from two donor strains give higher yields compared with reassortant influenza viruses which contain backbone segments from only a single donor strains.

It will be understood that the invention has been described by way of example only and modifications may be made whilst remaining within the scope and spirit of the invention.

SEQUENCES

DEPOSIT INFORMATION
A deposit of the microorganism MDCK 33016 (DSM ACC2219) was deposited on
Jun. 7, 1995 according to the Budapest Treaty-
 in the International Depository
Authority DSM-Deutsche Sammlung Von Mikroorganismem und Zellkulturen GmbH,
Mascheroder Weg 1b, D-38124 Braunschweig.

SEQUENCE: 1 (PA, A/New Caledonia/20/1999)
GATTCGAAATGGAAGATTTTGTGCGACAATGCTTCAATCCGATGATTGTCGAGCTTGCGGAAAAGGCAATGAAAG

AGTATGGAGAGGACCTGAAAATCGAAACAAACAAATTTGCAGCAATATGCACTCACTTGGAAGTATGCTTCATGT

ATTCAGATTTTCATTTCATCAATGAGCAAGGCGAATCAATAATAGTAGAGCCTGAGGACCCAAATGCACTTTTAA

AGCACAGATTTGAGATAATAGAGGGACGAGATCGTACAATGGCATGGACAGTTGTAAACAGTATTTGCAACACCA

CAGGAGCTGAGAAACCAAAGTTTCTGCCAGATCTGTATGATTACAAAGAGAATAGATTCATCGAGATTGGAGTGA

CAAGGAGGGAAGTTCACATATACTATCTGGAAAAGGCCAACAAAATTAAATCTGAGAAGACACACATTCACATTT

| SEQUENCES |
|---|
| TCTCATTCACTGGCGAAGAAATGGCCACAAAGGCCGATTACACTCTCGATGAAGAAAGCAGGGCTAGGATTAAAA |
| CCAGACTATTCACCATAAGACAAGAAATGGCAAGCAGAGGTCTTTGGGACTCCTTTCGTCAGTCCGAAAGAGGCG |
| AAGAAACAATTGAAGAAAGATTTGAAATCACAGGGACAATGCGCAGGCTCGCTGACCAAAGCCTTCCGCCGAACT |
| TCTCCTGCATTGAGAATTTTAGAGCCTATGTGGATGGATTTGAACCGAACGGCTACATTGAGGGCAAGCTTTCTC |
| AAATGTCCAAAGAAGTAAATGCTAGAATTGAGCCTTTTTTGAAAACAACACCACGACCAATTAGACTTCCGGATG |
| GGCCTCCTTGTTTTCAGCGGTCAAAATTCCTGCTGATGGATTCTTTAAAATTAAGCATTGAGGATCCAAATCATG |
| AAGGAGAGGGAATACCACTATATGATGCAATCAAGTGTATGAGAACATTCTTTGGATGGAAAGAACCCTCTGTTG |
| TCAAGCCACACGGGAAGGGAATAAATCCGAATTATCTGCTGTCATGGAAGCAGGTATTGGAAGAGCTGCAGGACA |
| TTGAGAGTGAGGAGAAGATTCCAAGAACAAAAAACATGAAAAAAACGAGTCAGCTAAAGTGGGCACTTGGTGAGA |
| ACATGGCACCAGAGAAGGTGGATTTTGATGACTGTAAAGATATAAGCGATTTGAAGCAATATGATAGTGACGAAC |
| CTGAATTAAGGTCATTTTCAAGTTGGATCCAGAATGAGTTCAACAAGGCATGCGAGCTGACCGATTCAATCTGGA |
| TAGAGCTCGATGAGATTGGAGAAGATGTGGCCCCGATTGAACACATTGCAAGCATGAGAAGAAATTACTTCACAG |
| CTGAGGTGTCCCATTGCAGAGCCACAGAATATATAATGAAGGGGGTATACATTAATACTGCTTTGCTTAATGCAT |
| CCTGTGCAGCAATGGATGATTTCCAACTAATTCCCATGATAAGCAAATGTAGAACTAAAGAGGGAAGGAGAAAGA |
| CCAATTTGTACGGCTTCATCGTAAAAGGAAGATCTCACTTAAGGAATGACACCGATGTGGTAAACTTTGTGAGCA |
| TGGAGTTTTCCCTCACTGACCCAAGACTTGAGCCACACAAATGGGAGAAGTACTGTGTTCTTGAGATAGGAGATA |
| TGCTTCTAAGGAGTGCAATAGGCCAAGTGTCAAGGCCCATGTTCTTGTATGTAAGGACAAATGGAACCTCAAAAA |
| TTAAAATGAAATGGGGAATGGAGATGAGGCGTTGCCTCCTCCAATCCCTTCAACAAATAGAGAGCATGATTGAAG |
| CTGAGTCCTCCGTCAAGGAGAAAGACATGACAAAAGAGTTTTTTGAGAATAGATCAGAAACATGGCCCATTGGAG |
| AGTCACCAAAGGAGTGGAAGAAGGTTCCATTGGGAAAGTATGCAGGACACTATTGGCTAAGTCAGTATTCAATA |
| GTCTGTATGCATCTCCACAATTAGAAGGATTTTCAGCTGAGTCAAGAAAGTTGCTCCTCATTGTTCAGGCTCTTA |
| GGGACAATCTGGAACCTGGGACCTTTGATCTTGGGGGCTATATGAAGCAATTGAGGAGTGCCTGATTAATGATC |
| CCTGGGTTTTGCTTAATGCTTCTTGGTTCAACTCCTTCCTAACACATGCATTGAGATAGCTGGGGCAATGCTACT |
| ATTTACTATCCATACTGTCCAAAAAA |

SEQUENCE: 2 (PB1, A/New Caledonia/20/1999)
AATGGATGTCAATCCGACATTACTTTTCTTAAAAGTGCCAGCACAAAATGCTATAAGCACAACTTTTCCTTATAC

TGGTGACCCTCCTTACAGCCATGGGACAGGAACAGGGTACACCATGGATACAGTCAACAGGACACATCAGTACTC

AGAAAGAGGAAGATGGACAAAAAATACCGAAACTGGAGCACCGCAACTCAACCCAATTGATGGGCCACTACCAAA

AGACAATGAACCAAGTGGCTATGCCCAAACAGATTGTGTATTAGAAGCAATGGCTTTCCTTGAGGAATCCCATCC

TGGTATTTTTGAAAACTCTTGTATTGAAACAATGGAGGTTGTTCAGCAAACAAGGGTGGACAAACTGACACAAGG

CAGACAGACCTATGACTGGACTCTAAATAGGAACCAGCCTGCTGCCACAGCATTGGCCAACACTATAGAAGTGTT

CAGATCAAACGGCCTCATAGCAAATGAATCTGGGAGGCTAATAGACTTCCTTAAAGATGTAATGGAGTCGATGGA

CAGAGACGAAGTAGAGATCACAACTCATTTTCAAAGAAAGAGGAGAGTGAGAGACAATGTAACTAAAAAATGGT

GACCCAAAGAACAATAGGCAAAAGAAACATAAATTAGACAAAGAAGTTACCTAATTAGGGCATTAACCCTGAA

CACAATGACCAAAGATGCTGAGAGGGGGAAACTAAAACGCAGAGCAATTGCAACCCCAGGAATGCAAATAAGGGG

GTTTGTATACTTTGTTGAGACACTGGCAAGAAGCATATGTGAAAAGCTTGAACAATCAGGGTTGCCAGTTGGAGG

AAATGAAAGAAAGCAAAGTTAGCAAATGTTGTAAGGAAGATGATGACCAACTCCCAGGACACTGAAATTTCTTT

CACCATCACTGGAGATAACACAAAATGGAACGAAAATCAAACCCTAGAATGTTCTTGGCCATGATCACATATAT

AACCAAAAATCAGCCTGAATGGTTCAGAAATATTCTAAGTATTGCTCCAATAATGTTTTCAAACAAAATGGCGAG

| SEQUENCES |
|---|
| ACTAGGTAAGGGGTACATGTTTGAAAGCAAGAGTATGAAACTGAGAACTCAAATACCTGCAGAGATGCTAGCCAA |
| CATAGATTTGAAATATTTCAATGATTCAACTAAAAAGAAAATTGAAAAAATCCGGCCATTATTAATAGATGGAAC |
| TGCATCATTGAGTCCTGGAATGATGATGGGCATGTTCAATATGTTAAGCACCGTCTTGGGCGTCTCCATTCTGAA |
| TCTTGGGCAAAAGAGATACACCAAGACTACTTACTGGTGGGATGGTCTTCAATCGTCTGATGATTTTGCTCTGAT |
| TGTGAATGCACCCAACTATGCAGGAATTCAAGCTGGAGTTGACAGGTTTTATCGAACCTGTAAGCTGCTCGGAAT |
| TAATATGAGCAAAAGAAGTCTTACATAAACAGAACAGGTACCTTTGAGTTCACGAGCTTTTTCTATCGTTATGG |
| GTTTGTTGCCAATTTCAGCATGGAGCTTCCTAGTTTTGGGGTGTCTGGGGTCAATGAATCTGCAGACATGAGTAT |
| TGGAGTCACTGTCATCAAAAACAATATGATAAACAATGACCTTGGCCCAGCAACTGCTCAAATGGCCCTTCAGTT |
| ATTTATAAAAGATTACAGGTACACGTATCGATGCCACAGAGGTGACACACAAATACAAACCCGGAGATCATTTGA |
| GATAAAGAAACTATGGGACCAAACCCGCTCCAAAGCTGGGCTGTTGGTCTCTGATGGAGGCCCCAATTTATATAA |
| CATTAGAAATCTCCATATTCCTGAAGTCTGCTTGAAATGGGAGTTGATGGATGAGGATTACCAGGGGCGTTTATG |
| CAACCCATTGAACCCGTTTGTCAGTCATAAAGAGATTGAATCAGTGAACAATGCAGTGATGATGCCGGCACATGG |
| TCCAGCCAAAAATATGGAGTATGACGCTGTTGCAACAACACACTCCTGGGTTCCCAAAAGGAATCGATCCATTTT |
| GAATACGAGCCAAAGGGGGATACTTGAGGATGAGCAAATGTATCAGAGGTGCTGCAATTTATTTGAAAAATTCTT |
| CCCAAGTAGCTCATACAGAAGACCAGTTGGAATATCCAGTATGGTAGAGGCTATGGTTTCCAGAGCCCGAATTGA |
| TGCACGGATTGATTTCGAATCTGGAAGGATAAAAAAAGAGGAATTCGCTGAGATCATGAAGACCTGTTCCACCAT |
| TGAAGACCTCAGACGGCAAAAATAGGGAATTTGGCTTGTCCTTCATGAAAA |

SEQUENCE: 3 (PB2, A/New Caledonia/20/1999)
| |
|---|
| AATATGGAAAGAATAAAAGAGCTAAGGAATCTGATGTCACAATCTCGCACTCGCGAGATACTTACAAAAACTACT |
| GTAGACCACATGGCCATAATCAAGAAATACACATCAGGAAGACAGGAGAAAAACCCATCACTTAGAATGAAATGG |
| ATGATGGCAATGAAATACCCAATTACAGCAGATAAAAGGATAACGGAAATGATTCCTGAAAGAAATGAGCAAGGA |
| CAGACATTATGGAGTAAAGTGAATGATGCCGGATCAGACCGAGTGATGATATCACCCCTGGCTGTGACATGGTGG |
| AACAGAAATGGACCAGTGGCAAGTACTATTCACTATCCAAAAATCTACAAAACTTACTTTGAAAAGGTTGAAAGG |
| TTAAAACATGGAACCTTTGGCCCTGTACACTTTAGAAACCAAGTCAAAATACGCCGAAGAGTCGACATAAATCCT |
| GGTCATGCAGACCTCAGCGCCAAGGAGGCACAGGATGTAATTATGGAAGTTGTTTTCCCTAATGAAGTGGGAGCC |
| AGAATACTAACATCAGAATCGCAATTAACGATAACCAAGGAGAAAAAGAAGAACTCCAGAATTGCAAAATTTCC |
| CCTTTGATGGTTGCATACATGTTAGAGAGGGAACTTGTCCGCAAAACGAGATTTCTCCCGGTTGCTGGTGGAACA |
| AGCAGTGTGTACATTGAAGTTTTGCATTTAACACAGGGGACATGCTGGGAGCAGATGTACACTCCAGGTGGGGAG |
| GTGAGGAATGATGATGTTGATCAAAGCCTAATTATTGCTGCTAGGAACATAGTGAGAAGAGCTGCAGTATCAGCA |
| GATCCACTAGCATCTTTATTAGAAATGTGCCATAGCACACAGATTGGTGGGACAAGGATGGTGGATATTCTCAGG |
| CAAAATCCAACAGAAGAACAAGCTGTGGATATATGCAAAGCAGCAATGGGGCTGAGAATCAGTTCATCCTTCAGT |
| TTTGGCGGATTCACATTTAAGAGAACAAGTGGATCATCAGTCAAAGGGAGGAAGAAGTGCTCACGGGCAATCTG |
| CAAACATTGAAGCTAACTGTGCATGAGGGATATGAAGAGTTCACAATGGTTGGGAAAAGGGCAACAGCTATACTC |
| AGAAAAGCAACCAGGAGATTGATTCAACTAATAGTGAGTGGAAGAGACGAACAGTCAATAGTCGAAGCAATAGTT |
| GTAGCAATGGTATTCTCACAAGAAGATTGCATGGTAAAAGCAGTTAGAGGTGATCTGAATTTCGTTAATAGAGCG |
| AATCAGCGGTTGAATCCCATGCATCAACTTTTGAGACATTTTCAGAAGGATGCTAAAGTACTTTTCTTAAATTGG |
| GGAATTGAACCTATCGACAATGTGATGGGAATGATTGGGATATTACCTGATATGACTCCAAGTACCGAGATGTCA |
| ATGAGAGGAGTGAGAGTCAGCAAAATGGGTGTAGATGAATACTCCAATGCTGAAGGGTAGTGGTGAGCATTGAC |
| CGTTTTTTGAGAGTCCGGGACCAAAGAGGAAATGTACTACTGTCTCCAGAGGAAGTCAGTGAAACACAGGGAACA |

| SEQUENCES |
|---|
| GAGAAACTGACAATAACTTACTCTTCATCAATGATGTGGGAGATTAATGGCCCTGAGTCAGTGTTGATCAATACC |
| TATCAGTGGATCATCAGAAACTGGGAGACTGTTAAAATTCAGTGGTCTCAGAACCCTACAATGCTATACAATAAA |
| ATGGAATTCGAGCCATTTCAGTCTCTAGTCCCTAAGGCCATTAGAGGCCAATACAGTGGGTTTGTTAGAACTCTA |
| TTTCAACAAATGAGGGATGTGCTTGGACCTTTGACACAACTCAGATAATAAAACTTCTTCCCTTTGCAGCCGCT |
| CCACCAAAGCAAAGTAGAATGCAATTCTCATCATTGACTGTGAATGTGAGGGGATCAGGAATGAGAATACTTGTA |
| AGGGGTAATTCTCCAGTATTCAACTACAACAAGACCACTAAGAGACTCACAGTCCTCGGAAAGGATGCTGGCACT |
| TTAACTGAAGACCCAGATGAAGGCACAGCTGGAGTGGAATCTGCTGTTCTAAGGGGATTCCTCATTCTAGGCAAA |
| GAAGATAGAAGATATGGGCCAGCATTAAGCATCAATGAATTGAGCAACCTTGCGAAAGGGGAAAAAGCTAATGTG |
| CTAATTGGGCAAGGGGACGTAGTGTTGGTAATGAAACGAAAACGGGACTCTAGCATACTTACTGACAGCCAGACA |
| GCGACCAAAAGAATTCGGATGGCCATCAATTAATTTCGAATAATTTAAA |
| SEQUENCE: 4 (NP, A/New Caledonia/20/1999)<br>ATCACTCACTGAGTGACATCAAAGTCATGGCGTCCCAAGGCACCAAACGGTCTTACGAACAGATGGAGACTGATG |
| GGGAACGCCAGAATGCAACTGAAATCAGAGCATCCGTCGGAAGAATGATTGGTGGAATTGGGCGATTCTACATCC |
| AAATGTGCACCGAGCTTAAACTCAATGATTATGAGGGACGACTGATCCAGAACAGCTTGACAATAGAGAATGG |
| TGCTCTCTGCTTTTGATGAGAGGAGGAATAAATATCTGGAAGAACATCCCAGCGCGGGGAAAGATCCTAAGAAAA |
| CTGGAGGACCCATATACAAGAGAGTAGATGGAAAGTGGGTGAGGGAACTCGTCCTTTATGACAAAGAAGAAATAA |
| GGCGGATTTGGCGCCAAGCCAACAATGGTGATGATGCAACGGCTGGTTTGACTCACATTATGATCTGGCATTCTA |
| ATTTGAATGATACAACTTACCAGAGGACAAGAGCTCTTGTCCGCACCGGAATGGATCCCAGGATGTGCTCTTTGA |
| TGCAAGGTTCAACTCTCCCTAGAAGATCTGGAGCAGCAGGCGCTGCAGTCAAAGGAGTTGGGACAATGGTGTTGG |
| AGTTAATCAGGATGATCAAACGTGGGATCAATGACCGAAACTTCTGGAGGGGTGAGAATGGAAGAAAAACAAGGA |
| TTGCTTATGAGAGAATGTGCAACATTCTCAAAGGAAAATTTCAAACAGCTGCACAAAAAGCAATGATGGATCAAG |
| TGAGAGAAAGCCGGAACCCAGGAAATGCTGAGATCGAAGATCTCACTTTTCTGGCACGGTCTGCACTCATATTAA |
| GAGGGTCAGTTGCTCACAAGTCTTGCCTGCCTGCCTGTGTGTATGGACCAGCCGTAGCCAGTGGGTACGACTTCG |
| AAAAAGAGGGATACTCTTTGGTAGGGGTAGACCCTTTTAAACTGCTTCAAACCAGTCAGGTATACAGCCTAATCA |
| GACCAAACGAGAATCCCGCACACAAGAGTCAGTTGGTGTGGATGGCATGCAATTCTGCTGCATTTGAAGATCTAA |
| GAGTGTCAAGCTTCATCAGAGGGACAAGAGTACTTCCAAGGGGGAAGCTCTCCACTAGAGGAGTACAAATTGCTT |
| CAAATGAAAACATGGATGCTATTGTATCAAGTACTCTTGAACTGAGAAGCAGATACTGGGCCATAAGAACCAGAA |
| GTGGAGGGAACACTAATCAACAAGGGCCTCTGCGGGCCAAATCAGCACACAACCTACGTTTTCTGTGCAGAGAA |
| ACCTCCCATTTGACAAAACAACCATCATGGCAGCATTCACTGGGAATACGGAGGGAAGAACATCAGACATGAGGG |
| CAGAAATCATAAAGATGATGGAAAGTGCAAGACCAGAAGAAGTGTCCTTCCAGGGGCGGGGAGTCTTTGAGCTCT |
| CGGACGAAAGGGCAACGAACCCGATCGTGCCCTCCTTTGACATGAGTAATGAAGGATCTTATTTCTTCGGAGACA |
| ATGCAGAGGAGTACGACAATTAATGAA |
| SEQUENCE: 5 (M, A/New Caledonia/20/1999)<br>GATGAGTCTTCTAACCGAGGTCGAAACGTACGTTCTCTATCGTCCCGTCAGGCCCCCTCAAAGCCGAGATCGC |
| ACAGAGACTTGAAAATGTCTTTGCTGGAAAGAATACCGATCTTGAGGCTCTCATGGAATGGCTAAAGACAAGACC |
| AATCCTGTCACCTCTGACTAAGGGGATTTTAGGATTTGTGTTCACGCTCACCGTGCCCAGTGAGCGAGGACTGCA |
| GCGTAGACGCTTTGTCCAAAATGCCCTTAATGGGAATGGGGATCCAAATAATATGGACAGAGCAGTTAAACTGTA |
| TCGAAAGCTTAAGAGGGAGATAACATTCCATGGGGCAAAGAAATAGCACTCAGTTATTCTGCTGGTGCACTTGC |
| CAGTTGTATGGGACTCATATACAACAGGATGGGGGCTGTGACCACCGAATCAGCATTTGGCCTTATATGCGCAAC |
| CTGTGAACAGATTGCCGACTCCCAGCATAAGTCTCATAGGCAAATGGTAACAACAACCAACCCATTAATAAGACA |

TGAGAACAGAATGGTTCTGGCCAGCACTACAGCTAAGGCTATGGAGCAAATGGCTGGATCGAGTGAACAAGCAGC

TGAGGCCATGGAGGTTGCTAGTCAGGCCAGGCAGATGGTGCAGGCAATGAGAGCCATTGGGACTCATCCTAGCTC

TAGCACTGGTCTGAAAAATGATCTCCTTGAAAATTTGCAGGCCTATCAGAAACGAATGGGGGTGCAGATGCAACG

ATTCAAGTGATCCTCTTGTTGTTGCCGCAAGTATAATTGGGATTGTGCACCTGATATTGTGGATTATTGATCGCC

TTTTTTCCAAAAGCATTTATCGTATCTTTAAACACGGTTTAAAAAGAGGGCCTTCTACGGAAGGAGTACCAGAGT

CTATGAGGGAAGAATATCGAGAGGAACAGCAGAATGCTGTGGATGCTGACGATGGTCATTTGTCAGCATAGAGC

TAGAGTAAA

SEQUENCE: 6 (NS, A/New Caledonia/20/1999)
ATGGATTCCCACACTGTGTCAAGCTTTCAGGTAGATTGCTTCCTTTGGCATGTCCGCAAACAAGTTGCAGACCAA

GATCTAGGCGATGCCCCATTCCTTGATCGGCTTCGCCGAGATCAGAAGTCTCTAAAGGGAAGAGGCAGCACTCTC

GGTCTGAACATCGAAACAGCCACTTGTGTTGGAAAGCAAATAGTAGAGAGGATTCTGAAAGAAGAATCCGATGAG

GCATTTAAAATGACCATGGCCTCCGCACTTGCTTCGCGGTACCTAACTGACATGACTATTGAAGAAATGTCAAGG

GACTGGTTCATGCTCATGCCCAAGCAGAAAGTGGCTGGCCCTCTTTGTGTCAGAATGGACCAGGCGATAATGGAT

AAGAACATCATACTGAAAGCGAATTTCAGTGTGATTTTTGACCGGTTGGAGAATCTGACATTACTAAGGGCTTTC

ACCGAAGAGGGAGCAATTGTTGGCGAAATTTCACCATTGCCTTCTCTTCCAGGACATACTAATGAGGATGTCAAA

AATGCAATTGGGGTCCTCATCGGGGGACTTGAATGGAATGATAACACAGTTCGAGTCTCTGAAACTCTACAGAGA

TTCGCTTGGAGAAGCAGTAATGAGACTGGGGGACCTCCATTCACTCCAACACAGAAACGGAAAATGGCGGGAACA

ATTAGGTCAGAAGTTTGAAGAAATAAGATGGCTGATTGAAGAAGTGAGGCATAAATTGAAGACGACAGAGAATAG

TTTTGAGCAAATAACATTTATGCAAGCATTACAGCTATTGTTTGAAGTGGAACAAGAGATTAGAACGTTTTCGTT

TCAGCTTATTTAATGATAA

SEQUENCE: 7 (HA, A/New Caledonia/20/1999)
CCAAAATGAAAGCAAAACTACTGGTCCTGTTATGTACATTTACAGCTACATATGCAGACACAATATGTATAGGCT

ACCATGCCAACAACTCAACCGACACTGTTGACACAGTACTTGAGAAGAATGTGACAGTGACACACTCTGTCAACC

TACTTGAGGACAGTCACAATGGAAAACTATGTCTACTAAAAGGAATAGCCCCACTACAATTGGGTAATTGCAGCG

TTGCCGGATGGATCTTAGGAAACCCAGAATGCGAATTACTGATTTCCAAGGAATCATGGTCCTACATTGTAGAAA

CACCAAATCCTGAGAATGGAACATGTTACCCAGGGTATTTCGCCGACTATGAGGAACTGAGGGAGCAATTGAGTT

CAGTATCTTCATTTGAGAGATTCGAAATATTCCCCAAAGAAAGCTCATGGCCCAACCACACCGTAACCGGAGTAT

CAGCATCATGCTCCCATAATGGGAAAAGCAGTTTTTACAGAAATTTGCTATGGCTGACGGGAAGAATGGTTTGT

ACCCAAACCTGAGCAAGTCCTATGTAAACAACAAGAGAAAGAAGTCCTTGTACTATGGGGTGTTCATCACCCGC

CTAACATAGGGAACCAAAGGGCCCTCTATCATACAGAAAATGCTTATGTCTCTGTAGTGTCTTCACATTATAGCA

GAAGATTCACCCCAGAAATAGCCAAAAGACCCAAAGTAAGAGATCAGGAAGGAAGAATCAACTACTACTGGACTC

TGCTGGAACCTGGGGATACAATAATATTTGAGGCAAATGGAAATCTAATAGCGCCATGGTATGCTTTTGCACTGA

GTAGAGGCTTTGGATCAGGAATCATCACCTCAAATGCACCAATGGATGAATGTGATGCGAAGTGTCAAACACCTC

AGGGAGCTATAAACAGCAGTCTTCCTTTCCAGAATGTACACCCAGTCACAATAGGAGAGTGTCCAAAGTATGTCA

GGAGTGCAAAATTAAGGATGGTTACAGGACTAAGGAACATCCCATCCATTCAATCCAGAGGTTTGTTTGGAGCCA

TTGCCGGTTTCATTGAAGGGGGGTGGACTGGAATGGTAGATGGGTGGTATGGTTATCATCATCAGAATGAGCAAG

GATCTGGCTATGCTGCAGATCAAAAAAGTACACAAAATGCCATTAACGGGATTACAAACAAGGTGAATTCTGTAA

TTGAGAAATGAACACTCAATTCACAGCTGTGGGCAAAGAATTCAACAAATTGGAAAGAAGGATGGAAAACTTAA

ATAAAAAAGTTGATGATGGGTTTCTAGACATTTGGACATATAATGCAGAATTGTTGGTTCTACTGGAAAATGAAA

| SEQUENCES |
|---|
| GGACTTTGGATTTCCATGACTCCAATGTGAAGAATCTGTATGAGAAAGTAAAAAGCCAATTAAAGAATAATGCCA |
| AAGAAATAGGAAACGGGTGTTTTGAATTCTATCACAAGTGTAACAATGAATGCATGGAGAGTGTGAAAAATGGAA |
| CTTATGACTATCCAAAATATTCCGAAGAATCAAAGTTAAACAGGGAGAAAATTGATGGAGTGAAATTGGAATCAA |
| TGGGAGTCTATCAGATTCTGGCGATCTACTCAACTGTCGCCAGTTCCCTGGTTCTTTTGGTCTCCCTGGGGGCAA |
| TCAGCTTCTGGATGTGTTCCAATGGGTCTTTGCAGTGTAGAATATGCATCTGAGACCAGAATTTCAGAAATATAA |
| GAA |
| SEQUENCE: 8 (NA, A/New Caledonia/20/1999) |
| AATGAATCCAAATCAAAAAATAATAACCATTGGATCAATCAGTATAGCAATCGGAATAATTAGTCTAATGTTGCA |
| AATAGGAAATATTATTTCAATATGGGCTAGTCACTCAATCCAAACTGGAAGTCAAAACCACACTGGAGTATGCAA |
| CCAAAGAATCATCACATATGAAAACAGCACCTGGGTGAATCACACATATGTTAATATTAACAACACTAATGTTGT |
| TGCTGGAAAGGACAAAACTTCAGTGACATTGGCCGGCAATTCATCTCTTTGTTCTATCAGTGGATGGGCTATATA |
| CACAAAAGACAACAGCATAAGAATTGGCTCCAAAGGAGATGTTTTTGTCATAAGAGAACCTTTCATATCATGTTC |
| TCACTTGGAATGCAGAACCTTTTTTCTGACCCAAGGTGCTCTATTAAATGACAAACATTCAAATGGGACCGTTAA |
| GGACAGAAGTCCTTATAGGGCCTTAATGAGCTGTCCTCTAGGTGAAGCTCCGTCCCCATACAATTCAAAGTTTGA |
| ATCAGTTGCATGGTCAGCAAGCGCATGCCATGATGGCATGGGCTGGTTAACAATCGGAATTTCTGGTCCAGACAA |
| TGGAGCTGTGGCTGTACTAAAATACAACGGCATAATAACTGAAACCATAAAAAGTTGGAAAAAGCGAATATTAAG |
| AACACAAGAGTCTGAATGTGTCTGTGTGAACGGGTCATGTTTCACCATAATGACCGATGGCCCGAGTAATGGGGC |
| CGCCTCGTACAAAATCTTCAAGATCGAAAAGGGGAAGGTTACTAAATCAATAGAGTTGAATGCACCCAATTTTCA |
| TTATGAGGAATGTTCCTGTTACCCAGACACTGGCACAGTGATGTGTGTATGCAGGGACAACTGGCATGGTTCAAA |
| TCGACCTTGGGTGTCTTTTAATCAAAACCTGGATTATCAAATAGGATACATCTGCAGTGGGGTGTTCGGTGACAA |
| TCCGCGTCCCAAAGATGGAGAGGGCAGCTGTAATCCAGTGACTGTTGATGGAGCAGACGGAGTAAAGGGGTTTTC |
| ATACAAATATGGTAATGGTGTTTGGATAGGAAGGACTAAAAGTAACAGACTTAGAAAGGGGTTTGAGATGATTTG |
| GGATCCTAATGGATGGACAGATACCGACAGTGATTTCTCAGTGAAACAGGATGTTGTGGCAATAACTGATTGGTC |
| AGGGTACAGCGGAAGTTTCGTTCAACATCCTGAGTTAACAGGATTGGACTGTATAAGACCTTGCTTCTGGGTTGA |
| GTTAGTCAGAGGACTGCCTAGAGAAAATACAACAATCTGGACTAGTGGGAGCAGCATTTCTTTTTGTGGCGTAAA |
| TAGTGATACTGCAAACTGGTCTTGGCCAGACGGTGCTGAGTTGCCGTTCACCATTGACAAGTAG |
| SEQUENCE: 9 (PA, PR8-X) |
| AGCGAAAGCAGGTACTGATCCAAAATGGAAGATTTTGTGCGACAATGCTTCAATCCGATGATTGTCGAGCTTGCG |
| GAAAAAACAATGAAAGAGTATGGGGAGGACCTGAAAATCGAAACAAACAAATTTGCAGCAATATGCACTCACTTG |
| GAAGTATGCTTCATGTATTCAGATTTTCACTTCATCAATGAGCAAGGCGAGTCAATAATCGTAGAACTTGGTGAT |
| CCAAATGCACTTTTGAAGCACAGATTTGAAATAATCGAGGGAAGAGATCGCACAATGGCCTGGACAGTAGTAAAC |
| AGTATTTGCAACACTACAGGGGCTGAGAAACCAAAGTTTCTACCAGATTTGTATGATTACAAGGAGAATAGATTT |
| ATCGAAATTGGAGTAACAAGGAGAGAAGTTCACATATACTATCTGGAAAAGGCCAATAAAATTAAATCTGAGAAA |
| ACACACATCCACATTTTCTCGTTCACTGGGGAAGAAATGGCCACAAAGGCAGACTACACTCTCGATGAAGAAAGC |
| AGGGCTAGGATCAAAACCAGACTATTCACCATAAGACAAGAAATGGCCAGCAGAGGCCTCTGGGATTCCTTTCGT |
| CAGTCCGAGAGAGGAGAAGAGACAATTGAAGAAAGGTTTGAAATCACAGGAACAATGCGCAAGCTTGCCGACCAA |
| AGTCTCCCGCCGAACTTCTCCAGCCTTGAAAATTTTAGAGCCTATGTGGATGGATTCGAACCGAACGGCTACATT |
| GAGGGCAAGCTGTCTCAAATGTCCAAAGAAGTAAATGCTAGAATTGAACCTTTTTTGAAAACAACACCACGACCA |
| CTTAGACTTCCGAATGGGCCTCCCTGTTCTCAGCGGTCCAAATTCCTGCTGATGGATGCCTTAAAATTAAGCATT |
| GAGGACCCAAGTCATGAAGGAGAGGGAATACCGCTATATGATGCAATCAAATGCATGAGAACATTCTTTGGATGG |

| SEQUENCES |
|---|
| AAGGAACCCAATGTTGTTAAACCACACGAAAAGGGAATAAATCCAAATTATCTTCTGTCATGGAAGCAAGTACTG |
| GCAGAACTGCAGGACATTGAGAATGAGGAGAAAATTCCAAAGACTAAAAATATGAAGAAAACAAGTCAGCTAAAG |
| TGGGCACTTGGTGAGAACATGGCACCAGAAAAGGTAGACTTTGACGACTGTAAAGATGTAGGTGATTTGAAGCAA |
| TATGATAGTGATGAACCAGAATTGAGGTCGCTTGCAAGTTGGATTCAGAATGAGTTTAACAAGGCATGCGAACTG |
| ACAGATTCAAGCTGGATAGAGCTCGATGAGATTGGAGAAGATGTGGCTCCAATTGAACACATTGCAAGCATGAGA |
| AGGAATTATTTCACATCAGAGGTGTCTCACTGCAGAGCCACAGAATACATAATGAAGGGGGTGTACATCAATACT |
| GCCTTGCTTAATGCATCTTGTGCAGCAATGGATGATTTCCAATTAATTCAATGATAAGCAAGTGTAGAACTAAG |
| GAGGGAAGGCGAAAGACCAACTTGTATGGTTTCATCATAAAAGGAAGATCCCACTTAAGGAATGACACCGACGTG |
| GTAAACTTTGTGAGCATGGAGTTTTCTCTCACTGACCCAAGACTTGAACCACATAAATGGGAGAAGTACTGTGTT |
| CTTGAGATAGGAGATATGCTTATAAGAAGTGCCATAGGCCAGGTTTCAAGGCCCATGTTCTTGTATGTGAGAACA |
| AATGGAACCTCAAAAATTAAAATGAAATGGGGAATGGAGATGAGGCGTTGCCTCCTCCAGTCACTTCAACAAATT |
| GAGAGTATGATTGAAGCTGAGTCCTCTGTCAAAGAGAAAGACATGACCAAAGAGTTCTTTGAGAACAAATCAGAA |
| ACATGGCCCATTGGAGAGTCCCCCAAAGGAGTGGAGGAAAGTTCCATTGGGAAGGTCTGCAGGACTTTATTAGCA |
| AAGTCGGTATTCAACAGCTTGTATGCATCTCCACAACTAGAAGGATTTTCAGCTGAATCAAGAAAACTGCTTCTT |
| ATCGTTCAGGCTCTTAGGGACAACCTTGAACCTGGGACCTTTGATCTTGGGGGGCTATATGAAGCAATTGAGGAG |
| TGCCTGATTAATGATCCCTGGGTTTTGCTTAATGCTTCTTGGTTCAACTCCTTCCTTACACATGCATTGAGTTAG |
| TTGTGGCAGTGCTACTATTTGCTATCCATACTGTCCAAAAAAGTACCTTGTTTCTACT |

SEQUENCE: 10 (PB1, PR8-X)
AGCGAAAGCAGGCAAACCATTTGAATGGATGTCAATCCGACCTTACTTTTCTTAAAAGTGCCAACACAAAATGCT
ATAAGCACAACTTTCCCTTATACTGGAGACCCTCCTTACAGCCATGGGACAGGAACAGGATACACCATGGATACT
GTCAACAGGACACATCAGTACTCAGAAAAGGGAAGATGGACAACAAACACCGAAACTGGAGCACCGCAACTCAAC
CCGATTGATGGGCCACTGCCAGAAGACAATGAACCAAGTGGTTATGCCCAAACAGATTGTGTATTGGAGGCGATG
GCTTTCCTTGAGGAATCCCATCCTGGTATTTTTGAAAACTCGTGTATTGAAACGATGGAGGTTGTTCAGCAAACA
CGAGTAGACAAGCTGACACAAGGCCGACAGACCTATGACTGGACTCTAAATAGAAACCAACCTGCTGCAACAGCA
TTGGCCAACACAATAGAAGTGTTCAGATCAAATGGCCTCACGGCCAATGAGTCTGGAAGGCTCATAGACTTCCTT
AAGGATGTAATGGAGTCAATGAACAAAGAAGAAATGGGGATCACAACTCATTTTCAGAGAAAGAGACGGGTGAGA
GACAATATGACTAAGAAAATGATAACACAGAGAACAATGGGTAAAAGAAGCAGAGATTGAACAAAGGAGTTAT
CTAATTAGAGCATTGACCCTGAACACAATGACCAAAGATGCTGAGAGAGGGAAGCTAAAACGGAGAGCAATTGCA
ACCCCAGGGATGCAAATAAGGGGGTTTGTATACTTTGTTGAGACACTGGCAAGGAGTATATGTGAGAAACTTGAA
CAATCAGGGTTGCCAGTTGGAGGCAATGAGAAGAAAGCAAAGTTGGCAAATGTTGTAAGGAAGATGATGACCAAT
TCTCAGGACACCGAACTTTCTTTCACCATCACTGGAGATAACACCAAATGGAACGAAAATCAGAATCCTCGGATG
TTTTTGGCCATGATCACATATATGACCAGAAATCAGCCCGAATGGTTCAGAAATGTTCTAAGTATTGCTCCAATA
ATGTTCTCAAACAAAATGGCGAGACTGGGAAAAGGGTATATGTTTGAGAGCAAGAGTATGAAACTTAGAACTCAA
ATACCTGCAGAAATGCTAGCAAGCATCGATTTGAAATATTTCAATGATTCAACAAGAAGAAGATTGAAAAAATC
CGACCGCTCTTAATAGAGGGGACTGCATCATTGAGCCCTGGAATGATGATGGGCATGTTCAATATGTTAAGCACT
GTATTAGGCGTCTCCATCCTGAATCTTGGACAAAAGAGATACACCAAGACTACTTACTGGTGGGATGGTCTTCAA
TCCTCTGACGATTTTGCTCTGATTGTGAATGCACCCAATCATGAAGGGATTCAAGCCGGAGTCGACAGGTTTTAT
CGAACCTGTAAGCTACTTGGAATCAATATGAGCAAGAAAAGTCTTACATAAACAGAACAGGTACATTTGAATTC
ACAAGTTTTTTCTATCGTTATGGGTTTGTTGCCAATTTCAGCATGGAGCTTCCCAGTTTTGGGGTGTCTGGGATC

| SEQUENCES |
| --- |
| AACGAGTCAGCGGACATGAGTATTGGAGTTACTGTCATCAAAAACAATATGATAAACAATGATCTTGGTCCAGCA
ACAGCTCAAATGGCCCTTCAGTTGTTCATCAAAGATTACAGGTACACGTACCGATGCCATAGAGGTGACACACAA
ATACAAACCCGAAGATCATTTGAAATAAAGAAACTGTGGGAGCAAACCCGTTCCAAAGCTGGACTGCTGGTCTCC
GACGGAGGCCCAAATTTATACAACATTAGAAATCTCCACATTCCTGAAGTCTGCCTAAAATGGGAATTGATGGAT
GAGGATTACCAGGGGCGTTTATGCAACCCACTGAACCCATTTGTCAGCCATAAAGAAATTGAATCAATGAACAAT
GCAGTGATGATGCCAGCACATGGTCCAGCCAAAAACATGGAGTATGATGCTGTTGCAACAACACACTCCTGGATC
CCCAAAAGAAATCGATCCATCTTGAATACAAGTCAAAGAGGAGTACTTGAGGATGAACAAATGTACCAAAGGTGC
TGCAATTTATTTGAAAAATTCTTCCCCAGCAGTTCATACAGAAGACCAGTCGGGATATCCAGTATGGTGGAGGCT
ATGGTTTCCAGAGCCCGAATTGATGCACGGATTGATTTCGAATCTGGAAGGATAAAGAAAGAAGAGTTCACTGAG
ATCATGAAGATCTGTTCCACCATTGAAGAGCTCAGACGGCAAAAATAGTGAATTTAGCTTGTCCTTCATGAAAAA
ATGCCTTGTTTCTACT |
| SEQUENCE: 11 (PB2, PR8-X)
AGCGAAAGCAGGTCAATTATATTCAATATGGAAAGAATAAAAGAACTAAGAAATCTAATGTCGCAGTCTCGCACC
CGCGAGATACTCACAAAAACCACCGTGGACCATATGGCCATAATCAAGAAGTACACATCAGGAAGACAGGAGAAG
AACCCAGCACTTAGGATGAAATGGATGATGGCAATGAAATATCCAATTACAGCAGACAAGAGGATAACGGAAATG
ATTCCTGAGAGAAATGAGCAAGGACAAACTTTATGGAGTAAAATGAATGATGCCGGATCAGACCGAGTGATGGTA
TCACCTCTGGCTGTGACATGGTGGAATAGGAATGGACCAATAACAAATACAGTTCATTATCCAAAAATCTACAAA
ACTTATTTTGAAAGAGTAGAAAGGCTAAAGCATGGAACCTTTGGCCCTGTCCATTTTAGAAACCAAGTCAAAATA
CGTCGGAGAGTTGACATAAATCCTGGTCATGCAGATCTCAGTGCCAAGGAGGCACAGGATGTAATCATGGAAGTT
GTTTTCCCTAACGAAGTGGGAGCCAGGATACTAACATCGGAATCGCAACTAACGATAACAAAGAGAAGAAAGAA
GAACTCCAGGATTGCAAAATTTCTCCTTTGATGGTTGCATACATGTTGGAGAGAGAACTGGTCCGCAAAACGAGA
TTCCTCCCAGTGGCTGGTGGAACAAGCAGTGTGTACATTGAAGTGTTGCATTTGACTCAAGGAACATGCTGGGAA
CAGATGTATACTCCAGGAGGGGAAGTGAGGAATGATGATGTTGATCAAAGCTTGATTATTGCTGCTAGGAACATA
GTGAGAAGAGCTGCAGTATCAGCAGATCCACTAGCATCTTTATTGGAGATGTGCCACAGCACACAGATTGGTGGA
ATTAGGATGGTAGACATCCTTAGGCAGAACCCAACAGAAGAGCAAGCCGTGGATATATGCAAGGCTGCAATGGGA
CTGAGAATTAGCTCATCCTTCAGTTTTGGTGGATTCACATTTAAGAGAACAAGCGGATCATCAGTCAAGAGAGAG
GAAGAGGTGCTTACGGGAAATCTTCAAACATTGAAGATAAGAGTGCATGAGGGATATGAAGAGTTCACAATGGTT
GGGAGAAGAGCAACAGCCATACTCAGAAAAGCAACCAGGAGATTGATTCAGCTGATAGTGAGTGGGAGAGACGAA
CAGTCGATTGCCGAAGCAATAATTGTGGCCATGGTATTTTCACAAGAGGATTGTATGATAAAAGCAGTCAGAGGT
GATCTGAATTTCGTCAATAGGGCGAATCAGCGATTGAATCCTATGCATCAACTTTTAAGACATTTTCAGAAGGAT
GCGAGAGTGCTTTTTCAAAATTGGGGAGTTGAACCTATCGACAATGTGATGGGAATGATTGGGATATTGCCCGAC
ATGACTCCAAGCATCGAGATGTCAATGAGAGGAGTGAGAATCAGCAAAATGGGTGTAGATGAGTACTCCAGCACG
GAGAGGGTAGTGGTGAGCATTGACCGTTTTTTGAGAATCCGGGACCAACGAGGAAATGTACTACTGTCTCCCGAG
GAGGTCAGTGAAACACAGGGAACAGAGAAACTGACAATAACTTACTCATCGTCAATGATGTGGGAGATTAATGGT
CCTGAATCAGTATTGGTCAATACCTATCAATGGATCATCAGAAACTGGGAAACTGTTAAAATTCAGTGGTCCCAG
AACCCTACAATGCTATACAATAAAATGGAATTTGAACCATTTCAGTCTTTAGTACCTAAGGCCATTAGAGGCCAA
TACAGTGGGTTTGTAAGAACTCTGTTCCAACAAATGAGGGATGTGCTTGGGACATTTGATACCGCACAGATAATA
AAACTTCTTCCCTTCGCAGCCGCTCCACCAAAGCAAAGTAGAATGCAGTTCTCCTCATTTACTGTGAATGTGAGG
GGATCAGGAATGAGAATACTTGTAAGGGGCAATTCTCCTGTATTCAACTATAACAAGGCCACGAAGAGACTCACA |

| SEQUENCES |
|---|
| GTTCTCGGAAAGGATGCTGGCACTTTAACTGAAGACCCAGATGAAGGCACAGCTGGAGTGGAGTCCGCTGTTCTG |
| AGGGGATTCCTCATTCTGGGCAAAGAAGACAAGAGATATGGGCCAGCACTAAGCATCAATGAACTGAGCAACCTT |
| GCGAAAGGAGAGAAGGCTAATGTGCTAATTGGGCAAGGAGACGTGGTGTTGGTAATGAAACGGAAACGGGACTCT |
| AGCATACTTACTGACAGCCAGACAGCGACCAAAAGAATTCGGATGGCCATCAATTAGTGTCGAATAGTTTAAAAA |
| CGACCTTGTTTCTACT |
| SEQUENCE: 12 (NP, PR8-X) |
| AGCAAAAGCAGGGTAGATAATCACTCACTGAGTGACATCAAAATCATGGCGTCTCAAGGCACCAAACGATCTTAC |
| GAACAGATGGAGACTGATGGAGAACGCCAGAATGCCACTGAAATCAGAGCATCCGTCGGAAAAATGATTGGTGGA |
| ATTGGACGATTCTACATCCAAATGTGCACCGAACTCAAACTCAGTGATTATGAGGGACGGTTGATCCAAAACAGC |
| TTAACAATAGAGAGAATGGTGCTCTCTGCTTTTGACGAAAGGAGAAATAAATACCTTGAAGAACATCCCAGTGCG |
| GGAAAAGATCCTAAGAAAACTGGAGGACCTATATACAGGAGAGTAAACGGAAAGTGGATGAGAGAACTCATCCTT |
| TATGACAAAGAAGAAATAAGGCGAATCTGGCGCCAAGCTAATAATGGTGACGATGCAACGGCTGGTCTGACTCAC |
| ATGATGATCTGGCATTCCAATTTGAATGATGCAACTTATCAGAGGACAAGAGCTCTTGTTCGCACCGGAATGGAT |
| CCCAGGATGTGCTCTCTGATGCAAGGTTCAACTCTCCCTAGGAGGTCTGGAGCCGCAGGTGCTGCAGTCAAAGGA |
| GTTGGAACAATGGTGATGGAATTGGTCAGAATGATCAAACGTGGGATCAATGATCGGAACTTCTGGAGGGGTGAG |
| AATGGACGAAAAACAAGAATTGCTTATGAAAGAATGTGCAACATTCTCAAAGGGAAATTTCAAACTGCTGCACAA |
| AAAGCAATGATGGATCAAGTGAGAGAGAGCCGGAACCCAGGGAATGCTGAGTTCGAAGATCTCACTTTTCTAGCA |
| CGGTCTGCACTCATATTGAGAGGGTCGGTTGCTCACAAGTCCTGCCTGCCTGCCTGTGTGTATGGACCTGCCGTA |
| GCCAGTGGGTACGACTTTGAAAGGGAGGGATACTCTCTAGTCGGAATAGACCCTTTCAGACTGCTTCAAAACAGC |
| CAAGTGTACAGCCTAATCAGACCAAATGAGAATCCAGCACACAAGAGTCAACTGGTGTGGATGGCATGCCATTCT |
| GCCGCATTTGAAGATCTAAGAGTATTAAGCTTCATCAAAGGGACGAAGGTGCTCCCAAGAGGGAAGCTTTCCACT |
| AGAGGAGTTCAAATTGCTTCCAATGAAAATATGGAGACTATGGAATCAAGTACACTTGAACTGAGAAGCAGGTAC |
| TGGGCCATAAGGACCAGAAGTGGAGGAAACACCAATCAACAGAGGGCATCTGCGGGCCAAATCAGCATACAACCT |
| ACGTTCTCAGTACAGAGAAATCTCCCTTTTGACAGAACAACCATTATGGCAGCATTCAATGGGAATACAGAGGGG |
| AGAACATCTGACATGAGGACCGAAATCATAAGGATGATGGAAAGTGCAAGACCAGAAGATGTGTCTTTCCAGGGG |
| CGGGGAGTCTTCGAGCTCTCGGACGAAAAGGCAGCGAGCCCGATCGTGCCTTCCTTTGACATGAGTAATGAAGGA |
| TCTTATTTCTTCGGAGACAATGCAGAGGAGTACGACAATTAAAGAAAAATACCCTTGTTTCTACT |
| SEQUENCE: 13 (M, PR8-X) |
| AGCAAAAGCAGGTAGATATTGAAAGATGAGTCTTCTAACCGAGGTCGAAACGTACGTACTCTCTATCATCCCGTC |
| AGGCCCCCTCAAAGCCGAGATCGCACAGAGACTTGAAGATGTCTTTGCAGGGAAGAACACCGATCTTGAGGTTCT |
| CATGGAATGGCTAAAGACAAGACCAATCCTGTCACCTCTGACTAAGGGGATTTTAGGATTTGTGTTCACGCTCAC |
| CGTGCCCAGTGAGCGAGGACTGCAGCGTAGACGCTTTGTCCAAAATGCCCTTAATGGGAACGGGGATCCAAATAA |
| CATGGACAAAGCAGTTAAACTGTATAGGAAGCTCAAGAGGGAGATAACATTCCATGGGCCAAAGAAATCTCACT |
| CAGTTATTCTGCTGGTGCACTTGCCAGTTGTATGGGCCTCATATACAACAGGATGGGGCTGTGACCACTGAAGT |
| GGCATTTGGCCTGGTATGTGCAACCTGTGAACAGATTGCTGACTCCCAGCATCGGTCTCATAGGCAAATGGTGAC |
| AACAACCAATCCACTAATCAGACATGAGAACAGAATGGTTTTAGCCAGCACTACAGCTAAGGCTATGGAGCAAAT |
| GGCTGGATCGAGTGAGCAAGCAGCAGAGGCCATGGAGGTTGCTAGTCAGGCTAGACAAATGGTGCAAGCGATGAG |
| AACCATTGGGACTCATCCTAGCTCCAGTGCTGGTCTGAAAAATGATCTTCTTGAAAATTTGCAGGCCTATCAGAA |
| ACGAATGGGGGTGCAGATGCAACGGTTCAAGTGATCCTCTCACTATTGCCGCAAATATCATTGGGATCTTGCACT |

-continued

| SEQUENCES |
|---|

TGACATTGTGGATTCTTGATCGTCTTTTTTTCAAATGCATTTACCGTCGCTTTAAATACGGACTGAAAGGAGGGC

CTTCTACGGAAGGAGTGCCAAAGTCTATGAGGGAAGAATATCGAAAGGAACAGCAGAGTGCTGTGGATGCTGACG

ATGGTCATTTTGTCAGCATAGAGCTGGAGTAAAAAACTACCTTGTTTCTACT

SEQUENCE: 14 (NS, PR8-X)
AGCAAAAGCAGGGTGACAAAAACATAATGGATCCAAACACTGTGTCAAGCTTTCAGGTAGATTGCTTTCTTTGGC

ATGTCCGCAAACGAGTTGCAGACCAAGAACTAGGTGATGCCCCATTCCTTGATCGGCTTCGCCGAGATCAGAAAT

CCCTAAGAGGAAGGGGCAGTACTCTCGGTCTGGACATCAAGACAGCCACACGTGCTGGAAAGCAGATAGTGGAGC

GGATTCTGAAAGAAGAATCCGATGAGGCACTTAAAATGACCATGGCCTCTGTACCTGCGTCGCGTTACCTAACTG

ACATGACTCTTGAGGAAATGTCAAGGGACTGGTCCATGCTCATACCCAAGCAGAAAGTGGCAGGCCCTCTTTGTA

TCAGAATGGACCAGGCGATCATGGATAAGAACATCATACTGAAAGCGAACTTCAGTGTGATTTTTGACCGGCTGG

AGACTCTAATATTGCTAAGGGCTTTCACCGAAGAGGGAGCAATTGTTGGCGAAATTTCACCATTGCCTTCTCTTC

CAGGACATACTGCTGAGGATGTCAAAAATGCAGTTGGAGTCCTCATCGGAGGACTTGAATGGAATGATAACACAG

TTCGAGTCTCTGAAACTCTACAGAGATTCGCTTGGAGAAGCAGTAATGAGAATGGGAGACCTCCACTCACTCCAA

AACAGAAACGAGAAATGGCGGGAACAATTAGGTCAGAAGTTTGAAGAAATAAGATGGTTGATTGAAGAAGTGAGA

CACAAACTGAAGATAACAGAGAATAGTTTTGAGCAAATAACATTTATGCAAGCCTTACATCTATTGCTTGAAGTG

GAGCAAGAGATAAGAACTTTCTCGTTTCAGCTTATTTAGTACTAAAAAACACCCTTGTTTCTACT

SEQUENCE: 15 (HA, PR8-X)
AGCAAAAGCAGGGGAAAATAAAAACAACCAAAATGAAGGCAAACCTACTGGTCCTGTTATGTGCACTTGCAGCTG

CAGATGCAGACACAATATGTATAGGCTACCATACGAACAATTCAACCGACACTGTTGACACAGTACTCGAGAAGA

ATGTGACAGTGACACACTCTGTTAACCTGCTCGAAGACAGCCACAACGGAAAACTATGTAGATTAAAAGGAATAG

CCCCACTACAATTGGGGAAATGTAACATCGCCGGATGGCTCTTGGGAAACCCAGAATGCGACCCACTGCTTCCAG

TGAGATCATGGTCCTACATTGTAGAAACACCCAAACTCTGAGAATGGAATATGTTATCCAGGAGATTTCATCGACT

ATGAGGAGCTGAGGGAGCAATTGAGCTCAGTGTCATCATTCGAAAGATTCGAAATATTTCCCAAAGAAAGCTCAT

GGCCCAACCACAACACAAACGGAGTAACGGCAGCATGCTCCCATGAGGGGAAAAGCAGTTTTTACAGAAATTTGC

TATGGCTGACGGAGAAGGAGGGCTCATACCCAAAGCTGAAAAATTCTTATGTGAACAAAAAAGGGAAAGAAGTCC

TTGTACTGTGGGGTATTCATCACCCGCCTAACAGTAAGGAACAACAGAATCTCTATCAGAATGAAAATGCTTATG

TCTCTGTAGTGACTTCAAATTATAACAGGAGATTTACCCCGGAAATAGCAGAAAGACCCAAAGTAAGAGATCAAG

CTGGGAGGATGAACTATTACTGGACCTTGCTAAAACCCGGAGACACAATAATATTTGAGGCAAATGGAAATCTAA

TAGCACCAATGTATGCTTTCGCACTGAGTAGAGGCTTTGGGTCCGGCATCATCACCTCAAACGCATCAATGCATG

AGTGTAACACGAAGTGTCAAACACCCCTGGGAGCTATAAACAGCAGTCTCCCTTACCAGAATATACACCCAGTCA

CAATAGGAGAGTGCCCAAAATACGTCAGGAGTGCCAAATTGAGGATGGTTACAGGACTAAGGAACATTCCGTCCA

TTCAATCCAGAGGTCTATTTGGAGCCATTGCCGGTTTTATTGAAGGGGGATGGACTGGAATGATAGATGGATGGT

ATGGTTATCATCATCAGAATGAACAGGGATCAGGCTATGCAGCGGATCAAAAAAGCACACAAAATGCCATTAACG

GGATTACAAACAAGGTGAACACTGTTATCGAGAAAATGAACATTCAATTCACAGCTGTGGGTAAAGAATTCAACA

AATTAGAAAAAGGATGGAAAATTTAAATAAAAAAGTTGATGATGGATTTCTGGACATTTGGACATATAATGCAG

AATTGTTAGTTCTACTGGAAAATGAAAGGACTCTGGAATTCCATGACTCAAATGTGAAGAATCTGTATGAGAAAG

TAAAAAGCCAATTAAAGAATAATGCCAAAGAAATCGGAAATGGATGTTTTGAGTTCTACCACAAGTGTGACAATG

AATGCATGGAAAGTGTAAGAAATGGGACTTATGATTATCCCAAATATTCAGAAGAGTCAAAGTTGAACAGGGAAA

| SEQUENCES |
|---|
| AGGTAGATGGAGTGAAATTGGAATCAATGGGGATCTATCAGATTCTGGCGATCTACTCAACTGTCGCCAGTTCAC |
| TGGTGCTTTTGGTCTCCCTGGGGGCAATCAGTTTCTGGATGTGTTCTAATGGATCTTTGCAGTGCAGAATATGCA |
| TCTGAGATTAGAATTTCAGAGATATGAGGAAAAACACCCTTGTTTCTACT |

SEQUENCE: 16 (NA, PR8-X)
AGCAAAAGCAGGGGTTTAAAATGAATCCAAATCAGAAAATAATAACCATTGGATCAATCTGTCTGGTAGTCGGAC

TAATTAGCCTAATATTGCAAATAGGGAATATAATCTCAATATGGATTAGCCATTCAATTCAAACTGGAAGTCAAA

ACCATACTGGAATATGCAACCAAAACATCATTACCTATAAAAATAGCACCTGGGTAAAGGACACAACTTCAGTGA

TATTAACCGGCAATTCATCTCTTTGTCCCATCCGTGGGTGGCTATATACAGCAAAGACAATAGCATAAGAATTG

GTTCCAAAGGAGACGTTTTTGTCATAAGAGAGCCCTTTATTTCATGTTCTCACTTGGAATGCAGGACCTTTTTC

TGACCCAAGGTGCCTTACTGAATGACAAGCATTCAAGTGGGACTGTTAAGGACAGAAGCCCTTATAGGGCCTTAA

TGAGCTGCCCTGTCGGTGAAGCTCCGTCCCCGTACAATTCAAGATTTGAATCGGTTGCTTGGTCAGCAAGTGCAT

GTCATGATGGCATGGGCTGGCTAACAATCGGAATTTCAGGTCCAGATAATGGAGCAGTGGCTGTATTAAAATACA

ACGGCATAATAACTGAAACCATAAAAAGTTGGAGGAAGAAAATATTGAGGACACAAGAGTCTGAATGTGCCTGTG

TAAATGGTTCATGTTTTACTATAATGACTGATGGCCCGAGTGATGGGCTGGCCTCGTACAAAATTTTCAAGATCG

AAAAGGGGAAGGTTACTAAATCAATAGAGTTGAATGCACCTAATTCTCACTATGAGGAATGTTCCTGTTACCCTG

ATACCGACAAAGTGATGTGTGTGCAGAGACAATTGGCATGGTTCGAACCGGCCATGGGTGTCTTTCGATCAAA

ACCTGGATTATCAAATAGGATACATCTGCAGTGGGGTTTTCGGTGACAACCCGCGTCCCGAAGATGGAACAGGCA

GCTGTGGTCCAGTGTATGTTGATGGAGCAAACGGAGTAAAGGGATTTTCATATAGGTATGGTAATGGTGTTTGGA

TAGGAAGGACCAAAAGTCACAGTTCCAGACATGGGTTTGAGATGATTTGGGATCCTAATGGATGGACAGAGACTG

ATAGTAAGTTCTCTGTGAGGCAAGATGTTGTGGCAATGACTGATTGGTCAGGGTATAGCGGAAGTTTCGTTCAAC

ATCCTGAGCTGACAGGGCTAGACTGTATGAGGCCGTGCTTCTGGGTTGAATTAATCAGGGGACGACCTAAAGAAA

AAACAATCTGGACTAGTGCGAGCAGCATTTCTTTTTGTGGCGTGAATAGTGATACTGTAGATTGGTCTTGGCCAG

ACGGTGCTGAGTTGCCATTCAGCATTGACAAGTAGTCTGTTCAAAAAACTCCTTGTTTCTACT

SEQUENCE: 17 (PA, 105p30)
AGCGAAAGCAGGTACTGATTCGAAATGGAAGATTTTGTGCGACAATGCTTCAATCCGATGATTGTCGAGCTTGCG

GAAAAGGCAATGAAAGAGTATGGAGAGGACCTGAAAATCGAAACAAACAAATTTGCAGCAATATGCACCCACTTG

GAAGTATGCTTCATGTATTCAGATTTTCATTTCATCAATGAGCAAGGCGAATCAATAATAGTAGAGCCTGAGGAC

CCAAATGCACTTTTAAAACACAGATTTGAGATAATAGAGGGGCGAGATCGTACAATGGCATGGACAGTTGTAAAC

AGTATTTGCAACACCACAGGAGCTGAGAAACCAAAGTTTCTGCCAGATCTGTATGATTACAAAGAGAATAGGTTC

ATCGAAATTGGAGTGACAAGGAGAGAAGTTCACATATACTATCTGGAAAAGGCCAACAAAATTAAATCTGAGAAG

ACACATATTCACATTTTCTCATTTACTGGCGAAGAAATGGCCACAAAGGCCGATTACACTCTCGATGAAGAAAGC

AGGGCTAGAATTAAAACCAGACTATTCACCATAAGGCAAGAAATGGCAAGCAGAGGTCTTTGGGACTCCTTTCGT

CAGTCCGAAAGAGGCGAAGAGACAATTGAAGAAAGGTTTGAAATCACAGGGACAATGCGCAGGCTCGCTGATCAA

AGCCTTCCGCCGAACTTCTCCTGCATTGAGAATTTTAGAGCCTATGTGGATGGATTTGAACCGAACGGCTACATT

GAGGGCAAGCTTTCTCAAATGTCCAAAGAAGTAAATGCTAAAATTGAGCCTTTTTTGAAAACAACACCTCGACCA

ATTAGACTTCCGAATGGGCCTCCTTGTTTTCAGCGGTCAAAATTCCTGCTGATGGATTCTTTAAAATTAAGCATT

GAGGATCCAAATCATGAAGGGGAGGGAATACCACTATATGATGCAATCAAGTGTATGAGAACATTCTTTGGATGG

AAAGAACCCACTGTTGTCAAGCCACACGAGAAGGGAATAAATCCGAATTATCTGCTGTCGTGGAAGCAGGTGTTG

GAAGAGCTGCAGGACATTGAGAGTGAGGAGAAGATTCCAAGAACAAAAAACATGAAAAAAACGAGTCAGTTAAAG

TGGGCACTTGGTGAGAACATGGCACCAGAGAAGGTGGATTTTGATGACTGTAAAGATATAAGCGATTTGAAGCAA

| SEQUENCES |
|---|
| TATGATAGTGACGAACCTGAATTAAGGTCATTTTCAAGTTGGATCCAGAATGAGTTCAACAAGGCATGCGAGCTG |
| ACCGATTCAATCTGGATAGAGCTCGATGAGATTGGAGAAGATGTGGCCCCGATTGAACACATTGCAAGCATGAGA |
| AGAAATTACTTCACAGCTGAGGTGTCCCATTGCAGAGCCACTGAATATATAATGAAAGGGGTATACATTAATACT |
| GCTTTGCTTAATGCATCCTGTGCAGCAATGGATGATTTCCAACTAATTCCTATGATAAGCAAATGTAGAACTAAA |
| GAGGGAAGGAGAAAGACCAATTTGTACGGCTTCATCATAAAAGGAAGATCTCACTTAAGGAATGATACCGATGTG |
| GTAAACTTTGTGAGCATGGAGTTTTCCCTCACTGACCCAAGACTTGAGCCACACAAATGGGAGAAGTACTGTGTT |
| CTTGAGATAGGAGATATGCTTCTAAGGAGTGCAATAGGCCAAGTGTCAAGGCCCATGTTCTTGTATGTAAGAACA |
| AATGGAACCTCAAAAATTAAAATGAAATGGGGAATGGAGATGAGGCGTTGCCTCCTCCAATCCCTCCAACAAATA |
| GAGAGCATGATTGAAGCTGAGTCCTCTGTCAAGGAGAAAGACATGACAAAAGAGTTTTTTGAGAATAGATCAGAA |
| ACATGGCCCATTGGAGAGTCACCAAAAGGAGTGGAAGAAGGTTCCATTGGGAAAGTATGCAGGACACTATTGGCT |
| AAATCAGTATTCAATAGTCTGTATGCATCTCCACAATTAGAAGGATTTTCAGCTGAGTCAAGAAAGTTGCTCCTT |
| ATTGTTCAGGCTCTTAGGGACAATCTGGAACCTGGGACCTTTGATCTTGGGGACTATATGAAGCAATTGAGGAG |
| TGCCTGATTAATGATCCCTGGGTTTTGCTTAATGCTTCTTGGTTCAACTCCTTCCTAAAACATGCATTGAGATAG |
| CTGAGGCAATGCTACTATTTGTTATCCATACTGTCCAAAAAGTA |

SEQUENCE: 18 (PB1, 105p30)
AGCGAAAGCAGGCAAACCATTTGAATGGATGTCAATCCGACATTACTTTTCTTAAAAGTGCCAGCACAAAATGCT
ATAAGCACAACTTTTCCTTATACTGGTGACCCTCCTTACAGCCATGGAACAGGAACAGGATACACCATGGATACA
GTCAACAGGACACATCAGTACTCAGAAAGAGGAAGATGGACGAAAAATACCGAAACTGGAGCACCGCAACTCAAC
CCAATTGATGGGCCACTACCAGAAGACAATGAACCAAGTGGCTATGCCCAAACAGATTGTGTATTAGAGGCAATG
GCTTTCCTTGAAGAATCCCATCCTGGTATTTTTGAAAACTCTTGTATTGAAACAATGGAGGTTGTTCAGCAAACA
AGGGTGGACAAACTGACACAAGGCAGACAAACCTATGACTGGACTCTAAATAGGAACCAGCCTGCTGCCACAGCA
TTGGCAAACACCATAGAAGTATTCAGATCAAATGGCCTCATAGCAAATGAATCTGGAAGGCTAATAGACTTCCTT
AAAGATGTAATGGAGTCGATGGACAGAGACGAAGTAGAGGTCACAACTCATTTTCAAAGAAAGAGGAGAGTGAGA
GACAATGTAACTAAAAAAATGGTGACCCAAAGAACAATAGGAAAAAGAAACATAAATTAGACAAAAGAAGTTAC
CTAATTAGGGCATTAACCCTGAACACAATGACCAAAGATGCTGAGAGGGGGAAACTAAAACGCAGAGCAATTGCA
ACCCCAGGAATGCAAATAAGGGGGTTTGTATACTTTGTTGAGACACTGGCAAGAAGCATATGTGAAAAGCTTGAA
CAATCAGGGTTGCCAGTTGGAGGAAATGAGAAGAAAGCAAAGTTAGCAAATGTTGTAAGGAAGATGATGACCAAC
TCCCAGGACACTGAAATTTCTTTTACCATCACTGGAGATAACACAAAATGGAACGAAAATCAAACCCTAGAATG
TTCTTGGCCATGATCACATATATAACCAAAGATCAGCCTGAATGGTTCAGAAATATTCTAAGTATTGCTCCAATA
ATGTTTTCAAACAAAATGGCGAGACTAGGTAGGGGGTATATGTTTGAAAGCAAGAGTATGAAACTGAGAACCCAA
ATACCTGCAGAGATGCTAGCCAACATAGATTTGAAATATTTCAATGATTCAACTAAAAAGAAAATTGAAAAAATT
CGACCATTATTAATAGATGGAACTGCATCATTGAGTCCTGGAATGATGATGGGCATGTTCAATATGTTAAGCACC
GTCTTGGGCGTTTCCATTCTGAATCTTGGGCAAAAAGATACACCAAGACTACTTACTGGTGGGATGGTCTTCAA
TCGTCTGATGATTTTGCTTTGATTGTGAATGCACCCAATTATGCAGGAATTCAAGCTGGAGTTGACAGGTTTTAT
CGAACCTGTAAGCTGCTCGGAATTAATATGAGCAAAAAGAAGTCTTACATAAACAGAACAGGTACCTTTGAATTC
ACGAGCTTTTTCTATCGTTATGGGTTTGTTGCCAATTTCAGCATGGAGCTTCCTAGTTTTGGGGTGTCTGGGGTC
AATGAATCTGCAGACATGAGTATTGGAGTCACTGTCATCAAAAACAATATGATAAACAATGACCTTGGCCCAGCA
ACTGCTCAAATGGCCCTTCAGTTATTTATAAAAGATTACAGGTACACTTATCGATGCCACAGAGGTGACACACAA
ATACAAACCCGGAGATCATTTGAAATAAAGAAACTATGGGACCAAACCCGCTCCAAAGCTGGGCTGTTGGTCTCT

| SEQUENCES |
| --- |

GATGGAGGCCCCAATTTATATAACATTAGGAATCTACATATTCCTGAAGTCTGCTTGAAATGGGAGTTGATGGAT

GAGGATTACCAGGGGCGTTTATGCAACCCATTGAACCCGTTTGTCAGCCATAAAGAGATTGAATCAGTGAACAAT

GCAGTGATAATGCCGGCACATGGTCCAGCCAAAAATATGGAGTATGACGCTGTTGCAACAACACACTCTTGGGTC

CCCAAAAGAAATCGATCCATTTTAAACACGAGCCAAAGAGGGATACTTGAAGATGAGCAAATGTACCAAGGTGC

TGCAATTTATTTGAAAAATTCTTCCCAAGTAGCTCATACAGAAGACCAGTTGGAATATCCAGTATGGTAGAGGCT

ATGGTTTCAAGAGCCCGAATTGATGCACGGATTGATTTCGAATCTGGAAGGATAAAGAAAGAGGAATTCGCTGAG

ATCATGAAGACCTGTTCCACCATTGAAGACCTCAGACGGCAAAAATAGGGAATTTGGCTTGTCCTTCATGAAAAA

ATGCCTTGTTTCTACT

SEQUENCE: 19 (PB2, 105p30)
AGCGAAAGCAGGTCAATTATATTCAATATGGAAAGAATAAAAGAGCTAAGGAATCTGATGTCACAATCTCGCACT

CGCGAGATACTTACCAAAACTACTGTAGACCACATGGCCATAATAAAGAAATACACATCAGGAAGACAGGAGAAA

AACCCATCACTTAGGATGAAATGGATGATGGCAATGAAATACCCAATTACAGCTGATAAAAGGATAACGGAAATG

ATTCCTGAAAGAAATGAGCAAGGACAGACACTATGGAGTAAAGTGAATGATGCCGGATCAGACCGAGTGATGATA

TCACCCCTAGCTGTGACATGGTGGAACAGAAATGGACCAGTGGCAAACACTATCCACTATCCAAAAATCTACAAA

ACTTACTTTGAAAAGGTTGAAAGGTTAAAACATGGAACCTTTGGCCCTGTACACTTTAGAAACCAAGTCAAAATA

CGCCGAAGAGTCGACATAAATCCTGGTCATGCAGACCTCAGCGCCAAGGAGGCACAGGATGTAATTATGGAAGTT

GTTTTCCCTAATGAAGTGGGGAGCCAGAATACTAACATCAGAATCGCAATTAACGATAACTAAGGAGAAAAAGAG

GAACTCCAGAATTGCAAAATTTCCCCTTTGATGGTTGCATACATGTTAGAGAGGGAACTTGTCCGCAAAACAAGA

TTTCTCCCGGTTGCAGGTGGAACAAGCAGTGTGTACATTGAAGTTTTGCATTTAACACAGGGGACATGCTGGGAG

CAGATGTACACTCCAGGTGGGGAGGTGAGGAATGATGATGTTGATCAAAGCCTAATTATTGCTGCTAGGAACATA

GTGAGAAGAGCTGCAGTATCAGCAGATCCACTAGCATCTTTATTAGAAATGTGCCATAGCACACAGATTGGTGGA

ACAAGGATGGTGGATATTCTCAGGCAAAATCCAACAGAAGAACAAGCTGTGGACATATGCAAAGCAGCAATGGGG

CTGAGAATCAGTTCATCCTTCAGTTTTGGCGGATTCACATTTAAGAGAACAAGTGGATCGTCAGTCAAAAGGGAG

GAAGAAGTGCTAACGGGCAATCTGCAAACATTGAAGCTAACTGTGCATGAGGGATATGAAGAATTCACAATAGTT

GGGAAAAAGGCAACAGCTATACTCAGAAAAGCAACCAGGAGATTGATTCAACTAATAGTGAGTGGAAGAGACGAA

CAGTCAATAGTCGAAGCAATAGTTGTAGCAATGGTATTCTCACAAGAAGATTGCATGGTAAAAGCGGTTAGAGGT

GATCTGAATTTCGTTAATAGAGCGAATCAGCGGTTGAATCCCATGCATCAACTTTTGAGACATTTTCAGAAGGAT

GCTAAAGTACTTTTCCTAAATTGGGGAATTGAACATATTGACAATGTGATGGGAATGATTGGGATATTACCTGAT

ATGACTCCAAGTACCGAGATGTCAATGAGAGGAGTGAGAGTCAGCAAAATGGGTGTAGATGAATACTCCAATGCT

GAAAGGGTAGTGGTAAGCATTGACCGTTTTTTGAGGGTCCGGGACCAAAGAGGAAATGTATTACTGTCTCCAGAG

GAAGTCAGTGAAACACAAGGAACAGAGAAACTGACAATAACTTACTCTTCATCATTGATGTGGGAGATTAATGGC

CCTGAGTCAGTGTTGATCAATACCTACCAATGGATCATCAGAAACTGGGAGACTGTTAAAATTCAGTGGTCTCAG

AACCCTACAATGCTATACAATAAAATGGAATTTGAGCCATTTCAATCTCTAGTCCCCAAGGCCATTAGAGGCCAA

TACAGTGGGTTTGTTAGAACTCTATTTCAACAAATGAGGGATGTGCTCGGGACCTTTGACACAACTCAGATAATA

AAACTTCTTCCCTTTGCAGCCGCTCCACCAAAGCAAAGTAGAATGCAATTCTCGTCATTAACTGTGAATGTGAGG

GGATCAGGAATGAGAATACTTGTAAGGGGTAATTCTCCAGTATTCAACTACAACAAGACCACTAAGAGACTCACA

ATCCTCGGAAAGGATGCTGGCACTTTAACTGAAGACCCAGATGAAGGCACAGCTGGAGTGGAATCTGCTGTTTTA

AGGGGATTCCTCATTCTAGGCAAAGAAGATAGAAGATATGGGCCAGCATTAAGCATCAGTGAATTGAGCAACCTT

GCGAAAGGGGAGAAAGCTAATGTGCTAATTGGGCAAGGGGATGTAGTGTTGGTAATGAAACGAAAACGGGACTCT

-continued

SEQUENCES

AGCATACTTACTGACAGCCAGACAGCGACCAAAAGAATTCGGATGGCCATCAATTAATTTCGAATAATTTAAAAA

CGACCTTGTTTCTACT

SEQUENCE: 20 (NP, 105p30)
AGCAAAAGCAGGGTAGATAATCACTCACTGAGTGACATCAAAGTCATGGCGTCCCAAGGCACCAAACGGTCTTAC

GAACAGATGGAGACTGATGGGGAACGCCAGAATGCAACTGAAATCAGAGCATCCGTCGGAAGAATGATTGGGGGA

ATTGGGCGATTCTACATCCAAATGTGCACCGAGCTTAAGCTCAATGATTATGAGGGACGACTGATCCAGAACAGC

TTAACAATAGAGAGAATGGTGCTTTCTGCTTTTGATGAGAGGAGAAATAAATATCTGGAAGAACATCCCAGCGCA

GGGAAAGATCCTAAGAAAACTGGAGGACCCATATACAAGAGAGTAGATGGAAAGTGGGTGAGGGAACTCGTCCTT

TATGACAAAGAAGAAATAAGGCGGATTTGGCGCCAAGCCAACAATGGTGATGATGCAACAGCTGGTTTGACTCAC

ATTATGATCTGGCATTCTAATTTGAATGATACAACTTACCAGAGGACAAGAGCTCTTGTCCGCACCGGAATGGAT

CCCAGGATGTGCTCTTTGATGCAAGGTTCAACTCTCCCTAGAAGATCGGAGCAGCAGGCGCTGCAGTCAAAGGA

GTTGGGACAATGGTATTGGAGTTAATCAGGATGATCAAACGTGGGATCAACGACCGAAACTTCTGGAGGGGTGAG

AATGGGAGAAAACAAGGATTGCTTATGAGAGAATGTGCAACATTCTCAAAGGAAAATTTCAAACAGCTGCACAA

AAAGCAATGATGGATCAAGTGAGAGAAAGCCGGAACCCAGGAAATGCTGAGATCGAAGATCTCACTTTTCTGGCA

CGGTCTGCACTCATATTGAGAGGATCAGTTGCTCACAAGTCTTGCCTGCCTGCTTGTGTGTATGGACCAGCCGTA

GCCAGTGGGTATGACTTCGAAAAAGAGGGATACTCTTTGGTGGGAGTAGACCCTTTCAAACTGCTTCAAACCAGT

CAGGTATACAGCCTAATTAGACCAAACGAGAATCCCGCACACAAGAGCCAGTTGGTGTGGATGGCATGCAATTCT

GCTGCATTTGAAGATCTAAGAGTGTCAAGCTTCATCAGAGGGACAAGAGTACTTCCAAGGGGGAAGCTCTCCACT

AGAGGAGTACAAATTGCTTCAAATGAAAACATGGATGCTATTGTCTCAAGTACTCTTGAACTGAGAAGCAGATAC

TGGGCCATAAGAACCAGAAGTGGAGGGAACACCAATCAACAAAGGGCCTCTGCGGGCCAAATCAGCACACAACCT

ACGTTTTCTGTGCAGAGAAACCTCCCATTTGACAAAACAACCATCATGGCAGCATTCACTGGGAATACAGAGGGA

AGAACATCAGACATGCGGGCAGAAATCATAAAGATGATGGAAAGTGCAAGACCAGAAGAAGTGTCCTTCCAGGGA

CGGGGAGTCTTTGAGCTCTCGGACGAAAGGGCAACGAACCCGATCGTGCCCTCCTTTGACATGAGTAATGAAGGA

TCTTATTTCTTCGGAGACAATGCAGAGGAGTACGACAATTAATGAAAAATACCCTTGTTTCTACT

SEQUENCE: 21 (M, 105p30)
AGCAAAAGCAGGTAGATATTGAAAGATGAGTCTTCTAACCGAGGTCGAAACGTACGTTCTCTCTATCGTCCCATC

AGGCCCCCTCAAAGCCGAGATCGCACAGAGACTTGAAGATGTATTTGCTGGAAAGAATACCGATCTTGAGGCTCT

CATGGAATGGCTAAAGACAAGACCAATCCTGTCACCTCTGACTAAGGGGATTTTAGGATTTGTGTTCACGCTCAC

CGTGCCCAGTGAGCGAGGACTGCAGCGTAGACGCTTTGTCCAAAATGCCCTTAATGGGAATGGGGATCCAAATAA

TATGGACAAGGCTGTCAAACTGTATCGAAAGCTTAAGAGGGAGATAACATTCCATGGGGCCAAAGAAATAGCACT

CAGTTATTCTGCTGGAGCACTTGCCAGTTGTATGGGACTCATATACAACAGGATGGGGCTGTGACCACCGAATC

AGCATTTGGCCTTATATGTGCAACCTGTGAACAGATTGCCGACTCCCAGCATAAGTCTCATAGGCAAATGGTAAC

AACAACCAATCCATTAATAAGACATGAGAACAGAATGGTTCTGGCCAGCACTACAGCTAAGGCTATGGAGCAAAT

GGCTGGATCGAGTGAACAAGCAGCTGAGGCCATGGAGGTTGCTAGTCAGGCCAGGCAGATGGTGCAGGCAATGAG

AGCCATTGGGACTCATCCTAGCTCTAGCACTGGTCTGAAAAATGATCTCCTTGAAAATTTGCAGGCCTATCAGAA

ACGAATGGGGGTGCAGATGCAACGATTCAAGTGATCCTCTTGTTGTTGCCGCAAGTATAATTGGGATTGTGCACC

TGATATTGTGGATTATTGATCGCCTTTTTTCCAAAAGCATTTATCGTATTTTTAAACACGGTTTAAAAGAGGGC

CTTCTACGAAGGAGTACCGGAGTCTATGAGGGAAGAATATCGAGAGGAACAGCAGAATGCTGTGGATGCTGACG

ATGGTCATTTTGTCAGCATAGAGCTAGAGTAAAAAACTACCTTGTTTCTACT

| SEQUENCES |
| --- |

SEQUENCE: 22 (NS, 105p30)
AGCAAAAGCAGGGTGGCAAAGACATAATGGATTCCCACACTGTGTCAAGCTTTCAGGTAGATTGTTTCCTTTGGC

ATGTCCGCAAACAAGTTGCAGACCAAGATCTAGGCGATGCCCCCTTCCTTGATCGGCTTCGCCGAGATCAGAAGT

CTCTAAAGGGACGAGGCAACACTCTCGGTCTGAACATCGAAACAGCCACTTGTGTTGGAAAGCAAATAGTAGAGA

GGATTCTGAAAGAAGAATCCGATGAGACATTTAGAATGACCATGGCCTCCGCACTTGCTTCGCGGTACCTAACTG

ACATGACTGTTGAAGAAATGTCAAGGGACTGGTTCATGCTCATGCCCAAGCAGAAAGTGGCTGGCCCTCTTTGTG

TCAGAATGGACCAGGCGATAATGGATAAGAACATCATACTGAAAGCGAACTTCAGTGTGATTTTTGACCGGTTGG

AGAATCTGACATTACTAAGGGCTTTCACCGAAGAGGGAGCAATTGTTGGCGAAATTTCACCATTGCCTTCTTTTC

CAGGACATACTAATGAGGATGTCAAAAATGCAATTGGGGTCCTCATCGGGGGACTTGAATGGAATGATAACACAG

TTCGAGTCTCTGAAGCTCTACAGAGATTCGCTTGGAGAAGCAGTAATGAGACTGGGGGACCTCCATTCACTACAA

CACAGAAACGGAAAATGGCGGGAACAATTAGGTCAGAAGTTTGAAGAAATAAGATGGCTGATTGAAGAAGTGAGG

CATAAATTGAAGACGACAGAGAGTAGTTTTGAACAAATAACATTTATGCAAGCATTACAGCTATTGTTTGAAGTG

GAACAAGAGATTAGAACGTTCTCGTTTCAGCTTATTTAATGATAAAAACACCCTTGTTTCTACT

SEQUENCE: 23 (HA, 105p30)
AGCGAAAGCAGGGGAAAATAAAAGCAACCAAAATGAAAGTAAAACTACTGGTTCTGTTATGTACATTTACAGCTA

CATATGCAGACACAATATGTATAGGCTACCATGCCAACAACTCAACCGACACTGTTGACACAGTACTTGAGAAGA

ATGTAACAGTGACACACTCTGTCAACCTACTTGAGGACAGTCACAATGGAAAACTATGTCTACTAAAAGGAATAG

CCCCACTACAATTGGGTAATTGCAGCGTTGCCGGATGGATCTTAGGAAACCCAGAATGCGAATTACTGATTTCCA

AGGAATCATGGTCCTACATTGTAGAAACACCAAATCCTGAGAATGGAACATGTTACCCAGGGTATTTCGCCGACT

ATGAGGAACTGAGGGAGCAATTGAGTTCAGTATCTTCATTTGAAAGGTTCGAAATATTCCCCAAAGAGAGCTCAT

GGCCCAACCACACCGTAACCGGAGTATCAGCATCATGCTCCCATAACGGGAAAAGCAGTTTTTACAGAAATTTGC

TATGGCTGACGGGGAAGAATGGTTTGTACCCAAACCTGAGCAAGTCCTATGCAAACAACAAAGAGAAAGAAGTCC

TTGTACTATGGGGTGTTCATCACCCGCCTAACATAGGGGACCAAAGGGCCCTCTATCATACAGAAAATGCTTATG

TCTCTGTAGTGTCTTCACATTATAGCAGAAGATTCACCCCAGAAATAGCCAAAAGACCCAAGGTGAGAGACCAGG

AAGGAAGAATCAACTACTACTGGACTCTGCTGGAACCCGGGGATACAATAATATTTGAGGCAAATGGAAATCTAA

TAGCGCCAAGGTATGCTTTCGCACTGAGTAGAGGCTTGGGATCAGGAATCATCACCTCAAATGCACCAATGGATG

AATGTGATGCAAAGTGTCAAACACCTCAGGGAGCTATAAACAGCAGTCTTCCTTTCCAGAATGTACACCCAGTCA

CAATAGGAGAGTGTCCAAAGTATGTCAGGAGTGCAAAATTAAGGATGGTTACAGGACTAAGGAACATCCCATCCA

TTCAATCCAGAGGTTTGTTTGGAGCAATTGCCGGTTTCATTGAAGGGGGGTGGACTGGAATGGTAGATGGTTGGT

ATGGTTATCATCATCAGAATGAGCAAGGATCTGGGTATGCTGCAGATCAAAAAAGCACACAAAATGCCATTAACG

GGATTACAAACAAGGTGAATTCTGTAATTGAGAAATGAACACTCAATTCACAGCTGTGGGCAAAGAATTCAACA

AATTGGAAAGAAGGATGGAAAACTTAAATAAAAAAGTTGATGATGGGTTTCTAGACATTTGGACCTATAATGCAG

AATTGTTGGTTCTACTGGAAAATGAAAGGACTTTGGATTTCCATGACTCCAACGTGAAGAATCTGTATGAGAAAG

TAAAAAGCCAATTAAAGAATAATGCCAAAGAAATAGGAAACGGGTGTTTTGAATTCTATCACAAGTGTAACGATG

AATGCATGGAGAGTGTGAAAAATGGAACTTATGACTATCCAAAATATTCCGAAGAATCAAAGTTAAACAGAGAGA

AAATTGATGGAGTGAAATTGGAATCAATGGGAGTCTATCAGATTCTGGCGATCTACTCAACAGTCGCCAGTTCCC

TGGTTCTTTTGGTCTCCCTGGGGGCAATCAGCTTCTGGATGTGTTCCAATGGGTCTTTGCAGTGTAGAATATGCA

TCTAAGACCAGAATTTCAGAAATATAAGGAAAAACACCCTTGTTTCTACT

-continued

SEQUENCES

SEQUENCE: 24 (NA, 105p30)
AGCAAAAGCAGGAGTTTAAAATGAATCCAAATCAAAAAATAATAACCATTGGATCAATCAGTATAGCAATCGGAA
TAATTAGTCTAATGTTGCAAATAGGAAATATTATTTCAATATGGGCTAGTCACTCAATCCAAACTGGAAGTCAAA
ACCACACTGGAATATGCAACCAAAAAATCATCACATATGAAAACAGCACCTGGGTGAATCACACATATGTTAATA
TTAACAACACTAATGTTGTTGCTGGAAAGGACAAAACTTCAGTGACACTGGCCGGCAATTCATCTCTTTGTCCTA
TCAGTGGATGGGCTATATACAAAAGACAACAGCATAAGAATTGGCTCCAAAGGAGATGTTTTGTCATAAGAG
AACCTTTCATATCATGTTCTCACTTGGAATGCAGAACCTTTTTTCTGACCCAAGGTGCTCTATTAAATGACAAAC
ATTCAAATGGAACCGTTAAGGACAGAAGTCCTTATAGGGCCTTAATGAGCTGTCCTCTAGGTGAAGCCCCGTCAC
CATACAATTCAAAGTTTGAATCAGTTGCATGGTCAGCAAGCGCATGCCATGATGGCAAGGGCTGGTTAACAATCG
GAATTTCTGGTCCAGACAATGGAGCTGTGGCTGTACTAAAATACAACGGAATAATAACTGAAACCATAAAAGTT
GGGAAAAGCGAATATTGAGAACACAAGAGTCTGAATGTGTTTGTGTGAACGGGTCATGTTTCACCATAATGACCG
ATGGCCCGAGTAATGGGCCGCCTCGTACAAAATCTTCAAGATCGAAAAGGGGAAGGTTACTAAATCAACAGAGT
TGAATGCACCCAATTTTCATTATGAGGAATGTTCCTGTTACCCAGACACTGGCACAGTGATGTGTGTATGCAGGG
ACAACTGGCATGGTTCAAATCGACCTTGGGTATCTTTTAATCAAAACTTGGATTATCAAATAGGATACATCTGCA
GTGGAGTGTTCGGTGACAATCCGCGTCCCAAAGATGGGAAGGGCAGCTGTAATCCAGTGACTGTTGATGGAGCAG
ACGGAGTTAAGGGGTTTTCATACAAATATGGTAATGGTGTTTGGATAGGAAGGACTAAAAGTAACAGACTTAGAA
AGGGGTTTGAGATGATTTGGGATCCTAATGGATGGACAGATACCGACAGTGATTTCTCAGTGAAACAGGATGTTG
TGGCAATAACTGATTGGTCAGGGTACAGCGGAAGTTTCGTCCAACATCCTGAGTTAACAGGATTGGACTGTATAA
GACCTTGCTTCTGGGTTGAGTTAGTCAGAGGACTGCCTAGAGAAAATACAACAATCTGGACTAGTGGGAGCAGCA
TTTCTTTTTGTGGCGTTGATAGTGATACTGCAAATTGGTCTTGGCCAGACGGTGCTGAGTTGCCGTTCACCATTG
ACAAGTAGCTCGTTGAAAAAAACTCCTTGTTTCTACT

SEQUENCE: 25 (HA, A/Chile/1/1983)
MKAKLLVLLCALSATDADTICIGYHANNSTDTVDTVLEKNVTVTHSVNLLEDNHNGKLCKLKGIAPLQLGKCSIA
GWILGNPECESLFSKKSWSYIAETPNSENGTCYPGYFADYEELREQLSSVSSFERFEIFPKESSWPKHNVTKGVT
AACSHKGKSSFYRNLLWLTEKNGSYPNLSKSYVNNKEKEVLVLWGVHHPSNIEDQKTIYRKENAYVSVVSSHYNR
RFTPEIAKRPKVRNQEGRINYYWTLLEPGDTIIFEANGNLIAPWYAFALSRGFGSGIITSNASMDECDAKCQTPQ
GAINSSLPFQNVHPVTIGECPKYVRSTKLRMVTGLRNIPSIQSRGLFGAIAGFIEGGWTGMIDGWYGYHHQNEQG
SGYAADQKSTQNAINGITNKVNSIIEKMNTQFTAVGKEENKLEKRMENLNKKVDDGFLDIWTYNAELLVLLENER
TLDFHDSNVKNLYEKVKSQLKNNAKEIGNGCFEFYHKCNNECMESVKNGTYDYPKYSEESKLNREKIDGVKLESM
GVYQILAIYSTVASSLVLLVSLGAISFWMCSNGSLQCRICI SEQUENCE: 26 (NA, A/Chile/1/1983)
MNPNQKIITIGSICMTIGIISLILQIGNIISIWVSHSIQTGSQNHTGICNQRIITYENSTWVNQTYVNINNTNVV
AGKDTTSVTLAGNSSLCPIRGWAIYSKDNSIRIGSKGDVFVIREPFISCSHLECRTFFLTQGALLNDKHSNGTVK
DRSPYRALMSCPIGEAPSPYNSRFESVAWSASACHDGMGWLTIGISGPDDGAVAVLKYNGIITETIKSWRKRILR
TQESECVCVNGSCFTIMTDGPSNGPASYRIFKIEKGKITKSIELDAPNSHYEECSCYPDTGTVMCVCRDNWHGSN
RPWVSFNQNLDYQIGYICSGVFGDNPRPKDGKGSCDPVTVDGADGVKGFSYRYGNGVWIGRTKSNSSRKGFEMIW
DPNGWTDTDSNFLVKQDVVAMTDWSGYSGSFVQHPELTGLDCMRPCFWVELVRGRPREGTTVWTSGSSISFCGVN
SDTANWSWPDGAELPFTIDK SEQUENCE: 27 (NA, A/California/04/09)
MNPNQKIITIGSVCMTIGMANLILQIGNIISIWISHSIQLGNQNQIETCNQSVITYENNTWVNQTYVNISNTNFA
AGQSVVSVKLAGNSSLCPVSGWAIYSKDNSVRIGSKGDVFVIREPFISCSPLECRTFFLTQGALLNDKHSNGTIK

| SEQUENCES |
|---|
| DRSPYRTLMSCPIGEVPSPYNSRFESVAWSASACHDGINWLTIGISGPDNGAVAVLKYNGIITDTIKSWRNNILR |
| TQESECACVNGSCFTVMTDGPSNGQASYKIFRIEKGKIVKSVEMNAPNYHYEECSCYPDSSEITCVCRDNWHGSN |
| RPWVSFNQNLEYQIGYICSGIFGDNPRPNDKTGSCGPVSSNGANGVKGFSFKYGNGVWIGRTKSISSRNGFEMIW |
| DPNGWTGTDNNFSIKQDIVGINEWSGYSGSFVQHPELTGLDCIRPCFWVELIRGRPKENTIWTSGSSISFCGVNS |
| DTVGWSWPDGAELPFTIDK |
| SEQUENCE: 28 (encodes the same amino acid sequence as SEQUENCE: 3)<br>ATGGAACGCATTAAAGAACTGCGCAACCTGATGAGCCAGAGCCGCACCCGCGAAATTCTGACCAAAACCACCGTG |
| GATCATATGGCGATTATTAAAAAATATACCAGCGGCCGCCAGGAAAAAAACCCGAGCCTGCGCATGAAATGGATG |
| ATGGCGATGAAATATCCGATTACCGCGGATAAACGCATTACCGAAATGATTCCGGAACGCAACGAACAGGGCCAG |
| ACCCTGTGGAGCAAAGTGAACGATGCGGGCAGCGATCGCGTGATGATTAGCCCGCTGGCGGTGACCTGGTGGAAC |
| CGCAACGGCCCGGTGGCGAGCACCATTCATTATCCGAAAATTTATAAACCTATTTTGAAAAAGTGGAACGCCTG |
| AAACATGGCACCTTTGGCCCGGTGCATTTTCGCAACCAGGTGAAAATTCGCCGCCGCGTGGATATTAACCCGGGC |
| CATGCGGATCTGAGCGCGAAAGAAGCGCAGGATGTGATTATGGAAGTGGTGTTTCCGAACGAAGTGGGCGCGCGC |
| ATTCTGACCAGCGAAAGCCAGCTGACCATTACCAAAGAAAAAAAGAAGAACTGCAGAACTGCAAAATTAGCCCG |
| CTGATGGTGGCGTATATGCTGGAACGCGAACTGGTGCGCAAAACCCGCTTTCTGCCGGTGGCGGGCGGCACCAGC |
| AGCGTGTATATTGAAGTGCTGCATCTGACCCAGGGCACCTGCTGGGAACAGATGTATACCCCGGGCGGCGAAGTG |
| CGCAACGATGATGTGGATCAGAGCCTGATTATTGCGGCGCGCAACATTGTGCGCCGCGCGGCGGTGAGCGCGGAT |
| CCGCTGGCGAGCCTGCTGGAAATGTGCCATAGCACCCAGATTGGCGGCACCCGCATGGTGGATATTCTGCGCCAG |
| AACCCGACCGAAGAACAGGCGGTGGATATTTGCAAAGCGGCGATGGGCCTGCGCATTAGCAGCAGCTTTAGCTTT |
| GGCGGCTTTACCTTTAAACGCACCAGCGGCAGCAGCGTGAAACGCGAAGAAGAAGTGCTGACCGGCAACCTGCAG |
| ACCCTGAAACTGACCGTGCATGAAGGCTATGAAGAATTTACCATGGTGGGCAAACGCGCGACCGCGATTCTGCGC |
| AAAGCGACCCGCCGCCTGATTCAGCTGATTGTGAGCGGCCGCGATGAACAGAGCATTGTGGAAGCGATTGTGGTG |
| GCGATGGTGTTTAGCCAGGAAGATTGCATGGTGAAAGCGGTGCGCGGCGATCTGAACTTTGTGAACCGCGCGAAC |
| CAGCGCCTGAACCCGATGCATCAGCTGCTGCGCCATTTTCAGAAAGATGCGAAAGTGCTGTTTCTGAACTGGGGC |
| ATTGAACCGATTGATAACGTGATGGGCATGATTGGCATTCTGCCGGATATGACCCCGAGCACCGAAATGAGCATG |
| CGCGGCGTGCGCGTGAGCAAAATGGGCGTGGATGAATATAGCAACGCGGAACGCGTGGTGGTGAGCATTGATCGC |
| TTTCTGCGCGTGCGCGATCAGCGCGGCAACGTGCTGCTGAGCCCGGAAGAAGTGAGCGAAACCCAGGGCACCGAA |
| AAACTGACCATTACCTATAGCAGCAGCATGATGTGGGAAATTAACGGCCCGGAAAGCGTGCTGATTAACACCTAT |
| CAGTGGATTATTCGCAACTGGGAAACCGTGAAAATTCAGTGGAGCCAGAACCCGACCATGCTGTATAACAAAATG |
| GAATTTGAACCGTTTCAGAGCCTGGTGCCGAAAGCGATTCGCGGCCAGTATAGCGGCTTTGTGCGCACCCTGTTT |
| CAGCAGATGCGCGATGTGCTGGGCACCTTTGATACCACCCAGATTATTAAACTGCTGCCGTTTGCGGCGGCGCCG |
| CCGAAACAGAGCCGCATGCAGTTTAGCAGCCTGACCGTGAACGTGCGCGGCAGCGGCATGCGCATTCTGGTGCGC |
| GGCAACAGCCCGGTGTTTAACTATAACAAAACCACCAAACGCCTGACCGTGCTGGGCAAAGATGCGGGCACCCTG |
| ACCGAAGATCCGGATGAAGGCACCGCGGGCGTGGAAAGCGCGGTGCTGCGCGGCTTTCTGATTCTGGGCAAAGAA |
| GATCGCCGCTATGGCCCGGCGCTGAGCATTAACGAACTGAGCAACCTGGCGAAAGGCGAAAAGCGAACGTGCTG |
| ATTGGCCAGGGCGATGTGGTGCTGGTGATGAAACGCAAACGCGATAGCAGCATTCTGACCGATAGCCAGACCGCG |
| ACCAAACGCATTCGCATGGCGATTAAC |

-continued

SEQUENCES

SEQUENCE: 29 (PA, A/New Caledonia/20/1999)
medfvrqcfnpmivelaekamkeygedpkietnkfaaicthlevcfmysdfhfidergesiivesgdpnallkhr
feiiegrdrimawtvvnsicnttgvekpkflpdlydykenrfieigvtrrevhiyylekankiksekthihifsf
tgeematkadytldeesrariktrlftirqemasrslwdsfrqsergeetieekfeitgtmrkladqslppnfps
lenfrayvdgfepngcieqklsqmskevnakiepflrttprplrlpdgplchqrskfllmdalklsiedpshege
giplydaikcmktffgwkepnivkphekginpnylmawkqvlaelqdieneekiprtknmkrtsqlkwalgenma
pekvdfddckdvgdlkqydsdepeprslaswvqnefnkaceltdsswieldeigedvapiehiasmrrnyftaev
shcrateyimkgvyintallnascaamddfqlipmiskcrtkegrrktnlygfiikgrshlrndtdvvnfvsmef
sltdprlephkwekycvleigdmllrtaigqvsrpmflyvrtngtskikmkwgmemrrcllqslqqiesmieaes
svkekdmtkeffenksetwpigesprgveegsigkvcrtllaksvfnslyaspqlegfsaesrklllivqalrdn
lepgtfdlgglyeaieeclindpwvllnaswfnsflthalk SEQUENCE: 30 (PB1, A/New Caledonia/20/1999)
mdvnptllflkvpaqnaisttfpytgdppyshgtgtgytmdtvnrthqysergrwtkntetgapqlnpidgplpk
dnepsgyaqtdcvleamafleeshpgifenscietmevvqqtrvdkltqgrqtydwtlnrnqpaatalantievf
rsnglianesgrlidflkdvmesmdrdevevtthfqrkrrvrdnvtkkmvtqrtigkkkhkldkrsyliraltln
tmtkdaergklkrraiatpgmqirgfvyfvetlarsiceklleqsglpvggnekkaklanvvrkmmtnsqdteisf
titgdntkwnenqnprmflamityitknqpewfrnilsiapimfsnkmarlgkgymfesksmklrtqipaemlan
idlkyfndstkrkiekirpllidgtaslspgmmmgmfnmlstvlgvsilnlgqkrytkttywwdglqssddfali
vnapnyagiqagvdrfyrtckllginmskkksyinrtgtfeftsffyrygfvanfsmelpsfgvsgvnesadmsi
gvtviknnminndlgpataqmalqlfikdyrytyrchrgdtqiqtrrsfeikklwdqtrskagllvsdggpnlyn
irnlhipevclkwelmdedyqgrlcnpsnpfvshkeiesvnnavmmpahgpaknmeydavatthswvpkrnrsil
ntsqrgiledeqmyqrccnlfekffpsssyrrpvgissmveamvsraridaridfesgrikkeefaeimktcsti
edlrrqk SEQUENCE: 31 (PB2, A/New Caledonia/20/1999)
merikelrnlmsqsrtreiltkttvdhmaiikkytsgrqeknpslrmkwmmamkypitadkritemiperneqgq
tlwskvndagsdrvmisplavtwwnrngpvastihypkiyktyfekverlkhgtfgpvhfrnqvkirrrvdinpg
hadlsakeaqdvimevvfpnevgariltsesqltitkekkeelqnckisplmvaymlerelvrktrflpvaggts
svyievlhltqgtcweqmytpggevrnddvdqsliiaarnivrraavsadplaslemchstqiggtrmvdilrq
npteeqavdickaamglrisssfsfggftfkrtsgssvkreeevltgnlqtlkltvhegyeeftmvgkrataillr
katrrliqlivsgrdeqsiveaivvamvfsqedcmvkavrgdlnfvnranqrlnpmhqllrhfqkdakvlflnwg
iepidnvmgmigilpdmtpstemsmrgvrvskmgvdeysnaervvvsidrflrvrdqrgnvllspeevsetqgte
kltityssmmweingpesvlintyqwiirnwetvkiqwsqnptmlynkmefepfqslvpkairgqysgfvrtlf
qqmrdvlgtfdttqiikllpfaaappkqsrmqfssltvnvrgsgmrilvrgnspvfnynktttkrltvlgkdagtl
tedpdegtagvesavlrgflilgkedrrygpalsinelsnlakgekanvligqgdvvlvmkrkrdssiltdsqta
tkrirmain SEQUENCE: 32 (NP, A/New Caledonia/20/1999)
masqgtkrsyeqmetdgerqnateirasvgrmiggigrfyiqmctelklndyegrliqnsltiermvlsafderr
nkyleehpsagkdpkktggpiykrvdgkwvrelvlydkeeirriwrqanngddataglthimiwhsnlndttyqr
tralvrtgmdprmcslmqgstlprrsgaagaavkgvgtmvlelirmikrgindrnfwrgengrktriayermcni
lkgkfqtaaqkammdqvresrnpgnaeiedltflarsalilrgsvahksclpacvygpavasgydfekegyslvg
vdpfkllqtsqvyslirpnenpahksqlvwmacnsaafedlrvssfirgtrvlprgklstrgvqiasnenmdaiv

| SEQUENCES |
| --- | sstlelrsrywairtrsggntnqqrasagqistqptfsvqrnlpfdkttimaaftgntegrtsdmraeiikmmes arpeevsfqgrgvfelsderatnpivpsfdmsnegsyffgdnaeeydn SEQUENCE: 33 (M1, A/New Caledonia/20/1999)
mslltevetyvlsivpsgplkaeiaqrlenvfagkntdlealmewlktrpilspltkgilgfvftltvpserglq rrrfvqnalngngdpnnmdravklyrklkreitfhgakeialsysagalascmgliynrmgavttesafglicat ceqiadsqhkshrqmvtttnplirhenrmvlasttakameqmagsseqaaeamevasqarqmvqamraigthpss stglkndllenlqayqkrmgvqmqrfk SEQUENCE: 34 (NA, A/New Caledonia/20/1999)
mnpnqkiitigsisiaigiislmlqigniisiwashsiqtgsqnhtgvcnqriityenstwvnhtyvninntnvv agkdktsvtlagnsslcsisgwaiytkdnsirigskgdvfvirepfiscshlecrtffltqgallndkhsngtvk drspyralmscplgeapspynskfesvawsasachdgmgwltigisgpdngavavlkyngiitetikswkkrilr tqesecvcvngscftimtdgpsngaasykifkiekgkvtksielnapnfhyeecscypdtgtvmcvcrdnwhgsn rpwvsfnqnldyqigyicsgvfgdnprpkdgegscnpvtvdgadgvkgfsykygngvwigrtksnrlrkgfemiw dpngwtdtdsdfsvkqdvvaitdwsgysgsfvqhpeltgldcirpcfwvelvrglprenttiwtsgssisfcgvn sdtanwswpdgaelpftidk SEQUENCE: 35 (PA, A/Wisconsin/67/2005)
medfvrqcfnpmivelaekamkeygedlkietnkfaaicthlevcfmysdfhfineqgesivvelddpnallkhr feiiegrdrtmawtvvnsicnttgagkpkflpdlydykenrfieigvtrrevhiyylekankiksenthihifsf tgeematkadytldeesrariktrlftirqemanrglwdsfrqsergeetieekfeitgtmrrladqslppnfsc lenfrayvdgfepngcieglksqmskevnaqiepflktprpiklpngppcyqrskfllmdalklsiedpshege giplydaikcmktffgwkepyivkphekginsnyllswkqvlselqdieneekiprtknmkktsqlkwalgenma pekvdfencrdisdlkqydsdepelrslsswiqnefnkaceltdsvwieldeigedvapiehiasmrrnyftaev shcrateyimkgvyintallnascaamddfqlipmiskcrtkegrrktnlygfiikgrshlrndtdvvnfvsmef sltdprlephkwekycvleigdmllrsaigqisrpmflyvrtngtskvkmkwgmemrrcllqslqqiesmieaes svkekdmtkeffenkseawpigespkgveegsigkvcrtllaksvfnslyaspqlegfsaesrklllvvqalrdn lepgtfdlgglyeaieeclindpwvllnaswfnsflthalk SEQUENCE: 36 (PB1, A/Wisconsin/67/2005)
mdvnptllflkvpaqnaisttfpytgdppyshgtgtgytmdtvnrthqysekgkwttntetgapqlnpidgplpe dnepsgyaqtdcvleamafleeshpgifenscletmeavqqtrvdrltqgrqtydwtlnrnqpaatalantievf rsngltanesgrlidflkdvmesmdkeemeitthfqrkrrvrdnmtkkmvtqrtigkkkqrvnkrgyliraltln tmtkdaergklkrraiatpgmqirgfvyfvetlarsicekleqsglpvggnekkaklanvvrkmmtnsqdtelsf titgdntkwnenqnprmflamityitknqpewfrnilsiapimfsnkmarlgkgymfeskrmklrtqipaemlas idlkyfnestrkkiekirplllidgtaslspgmmmgmfnmlstvlgvsilnlgqkkytkttywwdglqssddfali vnapnhegiqagvnrfyrtcklvginmskkksyinktgtfeftsffyrygfvanfsmelpsfgvsginesadmsi gvtviknnminndlgpataqmalqlfikdyrytyrchrgdtqiqtrrsfelkklwdqtqsragllvsdggpnlyn irnlhipevclkwelmdenyrgrlcnplnpfvshkeiesvnnavvmpahgpaksmeydavatthswipkrnrsil ntsqrgiledeqmyqkccnlfekffpsssyrrpigissmveamvsraridaridfesgrikkeefseimkicsti eelrrqr SEQUENCE: 37 (PB2, A/Wisconsin/67/2005)
merikelrnlmsqsrtreiltkttvdhmaiikkytsgrqeknpslrmkwmmamkypitadkritemvperneqgq tlwskmsdagsdrvmvsplavtwwnrngpvtstvhypkvyktyfdkverlkhgtfgpvhfrnqvkirrrvdinpg

| SEQUENCES |
|---| hadlsakeaqdvimevvfpnevgariltsesqltitkekkeelrdckisplmvaymlerelvrktrflpvaggts siyievlhltqgtcweqmytpggevrnddvdqsliiaarnivrraavsadplasllemchstqiggtrmvdilrq npteeqavdickaamglrisssfsfggftfkrtsgssvkkeeevltgnlqtlkirvhegyeeftmvgkrataillr katrrlvqlivsgrdeqsiaeaiivamvfsqedcmikavrgdlnfvnranqrlnpmhqllrhfqkdakvlfqnwg iehidsvmgmvgvlpdmtpstemsmrgirvskmgvdeysstervvvsidrflrvrdqrgnvllspeevsetqgte rltityssssmmweingpesvlvntyqwiirnweavkiqwsqnpamlynkmefepfqslvpkairsqysgfvrtlf qqmrdvlgtfdttqiikllpfaaappkqsrmqfssltvnvrgsgmrilvrgnspvfnynkttkrltilgkdagtl iedpdestsgvesavlrgfliigkedrrygpalsinelsnlakgekanvligqgdvvlvmkrkrdssiltdsqta tkrirmain SEQUENCE: 38 (NP, A/Wisconsin/67/2005)
masqgtkrsyeqmetdgdrqnateirasvgkmidgigrfyiqmctelklsdyegrliqnsltiekmvlsafderr nkyleehpsagkdpkktggpiyrrvdgkwmrelvlydkeeirriwrqanngedataglthimiwhsnlndatyqr tralvrtgmdprmcslmqgstlprrsgaagaavkgigtmvmelirmvkrgindrnfwrgengrktrsayermcni lkgkfqtaaqramvdqvresrnpgnaeiedliflarsalilrgsvahksclpacvygpavssgynfekegyslvg idpfkllqnsqvyslirpnenpahksqlvwmachsaafedlrllsfirgtkvsprgklstrgvqiasnenmdnmg sgtlelrsgywairtrsggntnqqrasagqtsvqptfsvqrnlpfekstimaaftgntegrtsdmraeiirmmeg akpeevsfrgrgvfelsdekatnpivpsfdmsnegsyffgdnaeeydn SEQUENCE: 39 (M1, A/Wisconsin/67/2005)
mslltevetyvlsivpsgplkaeiaqrledvfagkntdlealmewlktrpilspltkgilgfvftltvpserglq rrrfvqnalngngdpnnmdkavklyrklkreitfhgakeialsysagalascmgliynrmgavttevafglvcat ceqiadsqhrshrqmvattnplirhenrmvlasttakameqmagsseqaaeameiasqarqmvqamraigthpss stglrddllenlqtyqkrmgvqmqrfk SEQUENCE: 40 (M2, A/Wisconsin/67/2005)
mslltevetpirnewgcrcndssdplvvaaniigilhlilwildrlffkcvyrlfkhglkrgpstegvpesmree yrkeqqnavdaddshfvsiele SEQUENCE: 41 (NS, A/Wisconsin/67/2005)
AATGGATTCCAACACTGTGTCAAGTTTCCAGGTAGATTGCTTTCTTTGGCATATCCGGAAACAAGTTGTAGACCA

AGAACTGAGTGATGCCCCATTCCTTGATCGGCTTCGCCGAGATCAGAGGTCCCTAAGGGGAAGAGGCAATACTCT

CGGTCTAGACATCAAAGCAGCCACCCATGTTGGAAAGCAAATTGTAGAAAAGATTCTGAAAGAAGAATCTGATGA

GGCACTTAAAATGACCATGGTCTCCACACCTGCTTCGCGATACATAACTGACATGACTATTGAGGAATTGTCAAG

AAACTGGTTCATGCTAATGCCCAAGCAGAAAGTGGAAGGACCTCTTTGCATCAGAATGGACCAGGCAATCATGGA

GAAAAACATCATGTTGAAAGCGAATTTCAGTGTGATTTCTGACCGACTAGAGACCATAGTATTACTAAGGGCTTT

CACCGAAGAGGGAGCAATTGTTGGCGAAATCTCACCATTGCCTTCTTTTCCAGGACATACTATTGAGGATGTCAA

AAATGCAATTGGGGTCCTCATCGGAGGACTTGAATGGAATGATAACACAGTTCGAGTCTCTAAAAATCTACAGAG

ATTCGCTTGGAGAAGCAGTAATGAGAATGGGGGACCTCCACTTACTCCAAAACAGAAACGGAAATGGCGAGAAC

AGCTAGGTCAAAAGTTTGAAGAGATAAGATGGCTGATTGAAGAAGTGAGACACAGACTAAAAACAACTGAAAATA

GCTTTGAACAAATAACATTCATGCAAGCATTACAACTGCTGTTTGAAGTGGAACAGGAGATAAGAACTTTCTCAT

TTCAGCTTATTTAATGATAAA

SEQUENCE: 42 (HA, A/Wisconsin/67/2005)
mktiialsyilclvfaqklpgndnstatlclghhavpngtivktitndqievtnatelvqssstggicdsphqil dgenctlidallgdpqcdgfqnkkwdlfverskaysncypydvpdyaslrslvassgtlefndesfnwtgvtqng -continued

SEQUENCES tsssckrrsnnsffsrlnwlthlkfkypalnvtmpnnekfdklyiwgvhhpvtdndqiflyaqasgritvstkrs qqtvipnigsrprirnipsrisiywtivkpgdillinstgnliaprgyfkirsgkssimrsdapigkcnsecitp ngsipndkpfqnvnritygacpryvkqntlklatgmrnvpekqtrgifgaiagfiengwegmvdgwygfrhqnse gigqaadlkstqaainqingklnrligktnekfhqiekefsevegriqdlekyvedtkidlwsynaellvalenq htidltdsemnklfertkkqlrenaedmgngcfkiyhkcdnacigsirngtydhdvyrdealnnrfqikgvelks gykdwilwisfaiscfllcvallgfimwacqkgnircnici SEQUENCE: 43 (NA, A/Wisconsin/67/2005)
mnpnqkiitigsvsltisticffmqiailittvtlhfkqyefnsppnnqvmlceptiierniteivyltnttiek eicpklaeyrnwskpqcnitgfapfskdnsirlsaggdiwvtrepyvscdpdkcyqfalgqgttlnnvhsndtvh drtpyrtllmnelgvpfhlgtkqvciawssssschdgkawlhvcvtgddknatasfiyngrlvdsivswskeilrt qesecvcingtctvvmtdgsasgkadtkilfieegkivhtstlsgsaqhveecscyprylgvrcvcrdnwkgsnr pivdinikdysivssyvcsglvgdtprkndsssshcldpnneegghgvkgwafddgndvwmgrtiseklrsgye tfkviegwsnpnsklqinrqvivdrgnrsgysgifsvegkscinrcfyvelirgrkeetevlwtsnsivvfcgts gtygtgswpdgadinlmpi SEQUENCE: 44 (PA, 105p30)
medfvrqcfnpmivelaekamkeygedpkietnkfaaicthlevcfmysdfhfidergesiivesgdpnallkhr feiiegrdrimawtvinsicnttgvekpkflpdlydykenrfieigvtrrevhiyylekankiksekthihifsf tgeematkadytldeesrariktrlftirqemaskslwdsfrqsergeetieekfeitgtmrkladqslppnfps lenfrayvdgfepngcieglksqmskevnakiepflrttprplrlpdgplchqrskfllmdalklsiedpshege giplydaikcmktffgwkepnivkphekginpnylmawkqvlaelqdieneekiprtknmkrtsqlkwalgenma pekvdfddckdvgdlkqydsdepeprslaswvqnefnkaceltdsswieldeigedvapiehiasmrrnyftaev shcrateyimkgvyintallnascaamddfqlipmiskcrtkegrrktnlygfiikgrshlrndtdvvnfvsmef sltdprlephkwekycvleigdmllrtaigqvsrpmflyvrtngtskikmkwgmemrrcllqslqqiesmieaes svkekdmtkeffenksetwpigesprgveegsigkvcrtllaksvfnslyaspqlegfsaesrklllivqalrdn lepgtfdlgglyeaieeclindpwvllnaswfnsflthalk SEQUENCE: 45 (M1, 105p30)
mslltevetyvlsivpsgplkaeiaqrlenvfagkntdlealmewlktrpilspltkgilgfvftltvpserglq rrrfvqnalngngdpnnmdkavklyrklkreitfhgakeialsysagalascmgliynrmgavttesafglicat ceqiadsqhkshrqmvtttnplirhenrmvlasttakameqmagsseqaaeamevasqarqmvqamraigthpss stglkndllenlqayqkrmgvqmqrfk SEQUENCE: 46 (A/Texas/1/77 PB1)
mdvnptllflkipaqnaisttfpytgdppyshgtgtgytmdtvnrthqysekgkwttntetgapqlnpidgplpe dnepsgyaqtdcvleamafleeshpgifenscletmevvqqtrvdrltqgrqtydwtlnrnqpaatalantievf rsngltanesgrlidflkdvmesmdkeeieitthfqrkrrvrdnmtkkmvtqrtigkkkqrvnkrsyliraltln tmtkdaergklkrraiatpgmqirgfvyfvetlarsicekleqsglpvggnekkaklanvvrkmmtnsqdtelsf titgdntkwnenqnprmflamityitknqpewfrnilsiapimfsnkmarlgkgymfeskrmklrtqipaemlas idlkyfnestrkkiekirplidgtaslspgmmmgmfnmlstvlgvsilnlgqkkytkttywwdglqssddfali vnapnhegiqagvdrfyrtcklvginmskkksyinrtgtfeftsffyrygfvanfsmelpsfgvsginesadmsi gvtviknnminndlgpataqmalqlfikdyrytyrchrgdtqiqtrrsfelkklweqtrskagllvsdggpnlyn irnlhipevclkwelmdedyqgrlcnplnpfvshkeiesvnnavvmpahgpaksmeydavatthswipkrnrsil -continued

| SEQUENCES |
|---|
| ntsqrgiledeqmyqkccnlfekffpsssyrrpvgissmveamvsraridaridfesgrikkeefseimkicsti |
| eelrrqkq |
| SEQUENCE: 47 (A/Puerto Rico/8/34 PA)<br>medfvrqcfnpmivelaektmkeygedlkietnkfaaicthlevcfmysdfhfineqgesiivelgdpnallkhr |
| feiiegrdrtmawtvvnsicnttgaekpkflpdlydykenrfieigvtrrevhiyylekankiksekthihifsf |
| tgeematkadytldeesrariktrlftirqemasrglwdsfrqsergeetieerfeitgtmrkladqslppnfss |
| lenfrayvdgfepngyiegklsqmskevnariepflkttprplrlpngppcsqrskfllmdalklsiedpshege |
| giplydaikcmrtffgwkepnvvkphekginpnyllswkqvlaelqdieneekipktknmkktsqlkwalgenma |
| pekvdfddckdvgdlkqydsdepelrslaswiqnefnkaceltdsswieldeigedvapiehiasmrrnyftsev |
| shcrateyimkgvyintallnascaamddfqlipmiskcrtkegrrktnlygfiikgrshlrndtdvvnfvsmef |
| sltdprlephkwekycvleigdmlirsaigqvsrpmflyvrtngtskikmkwgmemrrcllqslqqiesmieaes |
| svkekdmtkeffenksetwpigespkgveessigkvcrtllaksvfnslyaspqlegfsaesrklllivqalrdn |
| lepgtfdlgglyeaieeclindpwvllnaswfnsflthals |
| SEQUENCE: 48 (A/Puerto Rico/8/34 NP)<br>masqgtkrsyeqmetdgerqnateirasvgkmiggigrfyiqmctelklsdyegrliqnsltiermvlsafderr |
| nkyleehpsagkdpkktggpiyrrvngkwmrelilydkeeirriwrqanngddatagltnmmiwhsnlndatyqr |
| tralvrtgmdprmcslmqgstlprrsgaagaavkgvgtmvmelvrmikrgindrnfwrgengrktriayermcni |
| lkgkfqtaaqkammdqvresrdpgnaefedltflarsalilrgsvahksclpacvygpavasgydferegyslvg |
| idpfrllqnsqvyslirpnenpahks |
| SEQUENCE: 49 (A/Puerto Rico/8/34 M)<br>mslltevetyvlsiipsgplkaeiaqrledvfagkntdlevlmewlktrpilspltkgilgfvftltvpserglq |
| rrrfvqnalngngdpnnmdkavklyrklkreitfhgakeislsysagalascmgliynrmgavttevafglvcat |
| ceqiadsqhrshrqmvtttnplirhenrmvlasttakameqmagsseqaaeamevasqarqmvqamrtigthpss |
| saglkndllenlqayqkrmgvqmqrfk |
| SEQUENCE: 50 (HA, A/California/04/09)<br>mkailvvllytfatanadtlcigy-<br>hannstdtvdtvleknvtvthsvnlledkhngklcklrgvaplhlgkcniagw |
| ilgnpeceslstasswsyivetpssd-<br>ngtcypgdfidyeelreqlssyssferfeifpktsswpnhdsnkgvtaacp |
| hagaksfyknliwlvkkgnsypklsksy-<br>indkgkevlvlwgihhpstsadqqslyqnadtyvfvgssryskkfkpei |
| airpkvrdqegrmnyywtlvepgdkit-<br>featgnlvvpryafamernagsgiiisdtpvhdcnttcqtpkgaintslp |
| fqnihpitigkcpkyvkstklrlatglr-<br>nipsiqsrglfgaiagfieggwtgmvdgwygyhhqneqgsgyaadlkst |
| qnaideitnkvnsviek-<br>mntqftavgkefnhlekrienlnkkvddgfldiwtynaellvllenertldyhdsnvknl |
| yekvrsqlknnakeigngcfefyh-<br>kcdntcmesvkngtydypkyseeaklnreeidgvklestriyqilaiystvas |
| slvlvvslgaisfwmcsngslqcrici |

REFERENCES

[1] WO2007/002008
[2] WO2007/124327
[3] WO2010/070098
[4] Needleman & Wunsch (1970) *J. Mol. Biol.* 48, 443-453.
[5] Rice et al. (2000) *Trends Genet.* 16:276-277.
[6] Herlocher et al. (2004) *J Infect Dis* 190(9):1627-30.
[7] Le et al. (2005) *Nature* 437(7062):1108.
[8] U.S. Pat. No. 6,468,544.
[9] Neumann et al. (2005) Proc Natl Acad Sci USA 102: 16825-9
[10] WO2009/000891
[11] U.S. provisional application No. 61/273,151

[12] Sambrook et al, Molecular Cloning: A Laboratory Manual, 2 ed., 1989, Cold Spring Harbor Press, Cold Spring Harbor, N.Y.
[13] WO2011/012999
[14] Kistner et al. (1998) Vaccine 16:960-8.
[15] Bruhl et al. (2000) Vaccine 19:1149-58.
[16] Pau et al. (2001) Vaccine 19:2716-21.
[17] http://www.atcc.org/
[18] http://locus.umdnj.edu/
[19] WO97/37000.
[20] Halperin et al. (2002) Vaccine 20:1240-7.
[21] EP-A-1260581 (WO01/64846)
[22] WO2006/071563
[23] WO2005/113758
[24] WO97/37001
[25] WO02/28422.
[26] WO2005/113756.
[27] Huckriede et al. (2003) *Methods Enzymol* 373:74-91.
[28] Vaccines. (eds. Plotkins & Orenstein). 4th edition, 2004, ISBN: 0-7216-9688-0
[29] Treanor et al. (1996) *J Infect Dis* 173:1467-70.
[30] Keitel et al. (1996) *Clin Diagn Lab Immunol* 3:507-10.
[31] Herlocher et al. (2004) *J Infect Dis* 190(9):1627-30.
[32] Le et al. (2005) *Nature* 437(7062):1108.
[33] WO2008/068631.
[34] Gennaro (2000) *Remington: The Science and Practice of Pharmacy.* 20th edition, ISBN: 0683306472.
[35] Banzhoff (2000) *Immunology Letters* 71:91-96.
[36] Nony et al. (2001) *Vaccine* 27:3645-51.
[37] EP-B-0870508.
[38] U.S. Pat. No. 5,948,410.
[39] WO2007/052163.
[40] WO2007/052061
[41] WO90/14837.
[42] Podda (2001) *Vaccine* 19: 2673-2680.
[43*] Vaccine Design: The Subunit and Adjuvant Approach* (eds. Powell & Newman) Plenum Press 1995 (ISBN 0-306-44867-X).
[44*] Vaccine Adjuvants: Preparation Methods and Research Protocols* (Volume 42 of *Methods in Molecular Medicine* series). ISBN: 1-59259-083-7. Ed. O'Hagan.
[45] WO2008/043774.
[46] Allison & Byars (1992) *Res Immunol* 143:519-25.
[47] Hariharan et al. (1995) *Cancer Res* 55:3486-9.
[48] US-2007/014805.
[49] US-2007/0191314.
[50] Suli et al. (2004) *Vaccine* 22(25-26):3464-9.
[51] WO95/11700.
[52] U.S. Pat. No. 6,080,725.
[53] WO2005/097181.
[54] WO2006/113373.
[55] Potter & Oxford (1979) *Br Med Bull* 35: 69-75.
[56] Greenbaum et al. (2004) *Vaccine* 22:2566-77.
[57] Piascik (2003) *J Am Pharm Assoc* (Wash DC). 43:728-30.
[58] Mann et al. (2004) *Vaccine* 22:2425-9.
[59] Halperin et al. (1979) *Am J Public Health* 69:1247-50.
[60] Herbert et al. (1979) *J Infect Dis* 140:234-8.
[61] Chen et al. (2003) *Vaccine* 21:2830-6.
[62] *Current Protocols in Molecular Biology* (F. M. Ausubel et al., eds., 1987) Supplement 30.
[63] Smith & Waterman (1981) *Adv. Appl. Math.* 2: 482-489.

SEQUENCE LISTING

```
<160> NUMBER OF SEQ ID NOS: 50

<210> SEQ ID NO 1
<211> LENGTH: 2201
<212> TYPE: DNA
<213> ORGANISM: Influenza A virus

<400> SEQUENCE: 1
gattcgaaat ggaagatttt gtgcgacaat gcttcaatcc gatgattgtc gagcttgcgg      60
aaaaggcaat gaaagagtat ggagaggacc tgaaaatcga aacaaacaaa tttgcagcaa     120
tatgcactca cttggaagta tgcttcatgt attcagattt tcatttcatc aatgagcaag     180
gcgaatcaat aatagtagag cctgaggacc caaatgcact tttaaagcac agatttgaga     240
taatagaggg acgagatcgt acaatggcat ggacagttgt aaacagtatt tgcaacacca     300
caggagctga gaaaccaaag tttctgccag atctgtatga ttacaaagag aatagattca     360
tcgagattgg agtgacaagg agggaagttc acatatacta tctggaaaag gccaacaaaa     420
ttaaatctga gaagacacac attcacattt tctcattcac tggcgaagaa atggccacaa     480
aggccgatta cactctcgat gaagaaagca gggctaggat taaaaccaga ctattcacca     540
taagacaaga aatggcaagc agaggtcttt gggactcctt tcgtcagtcc gaaagaggcg     600
aagaaacaat tgaagaaaga tttgaaatca cagggacaat gcgcaggctc gctgaccaaa     660
gccttccgcc gaacttctcc tgcattgaga attttagagc ctatgtggat ggatttgaac     720
cgaacggcta cattgagggc aagctttctc aaatgtccaa agaagtaaat gctagaattg     780
agcctttttt gaaaacaaca ccacgaccaa ttagacttcc ggatgggcct ccttgttttc     840
agcggtcaaa attcctgctg atggattctt taaaattaag cattgaggat ccaaatcatg     900
```

-continued

```
aaggagaggg aataccacta tatgatgcaa tcaagtgtat gagaacattc tttggatgga     960
aagaaccctc tgttgtcaag ccacacggga agggaataaa tccgaattat ctgctgtcat    1020
ggaagcaggt attggaagag ctgcaggaca ttgagagtga ggagaagatt ccaagaacaa    1080
aaaacatgaa aaaacgagt  cagctaaagt gggcacttgg tgagaacatg gcaccagaga    1140
aggtggattt tgatgactgt aaagatataa gcgatttgaa gcaatatgat agtgacgaac    1200
ctgaattaag gtcattttca agttggatcc agaatgagtt caacaaggca tgcgagctga    1260
ccgattcaat ctggatagag ctcgatgaga ttggagaaga tgtggccccg attgaacaca    1320
ttgcaagcat gagaagaaat tacttcacag ctgaggtgtc ccattgcaga gccacagaat    1380
atataatgaa gggggtatac attaatactg cttttgcttaa tgcatcctgt gcagcaatgg    1440
atgatttcca actaattccc atgataagca aatgtagaac taaagaggga aggagaaaga    1500
ccaatttgta cggcttcatc gtaaaaggaa gatctcactt aaggaatgac accgatgtgg    1560
taaactttgt gagcatggag ttttcccctca ctgacccaag acttgagcca cacaaatggg    1620
agaagtactg tgttcttgag ataggagata tgcttctaag gagtgcaata ggccaagtgt    1680
caaggcccat gttcttgtat gtaaggacaa atggaacctc aaaaattaaa atgaaatggg    1740
gaatggagat gaggcgttgc ctcctccaat cccttcaaca aatagagagc atgattgaag    1800
ctgagtcctc cgtcaaggag aaagacatga caaaagagtt ttttgagaat agatcagaaa    1860
catggccat  tggagagtca ccaaaaggag tggaagaagg ttccattggg aaagtatgca    1920
ggacactatt ggctaagtca gtattcaata gtctgtatgc atctccacaa ttagaaggat    1980
tttcagctga gtcaagaaag ttgctcctca ttgttcaggc tcttagggac aatctggaac    2040
ctgggacctt tgatcttggg gggctatatg aagcaattga ggagtgcctg attaatgatc    2100
cctgggtttt gcttaatgct tcttggttca actccttcct aacacatgca ttgagatagc    2160
tggggcaatg ctactatttta ctatccatac tgtccaaaaa a                      2201
```

<210> SEQ ID NO 2
<211> LENGTH: 2301
<212> TYPE: DNA
<213> ORGANISM: Influenza A virus

<400> SEQUENCE: 2

```
aatggatgtc aatccgacat tactttttctt aaaagtgcca gcacaaaatg ctataagcac     60
aacttttcct tatactggtg accctcctta cagccatggg acaggaacag ggtacaccat    120
ggatacagta acaggacac  atcagtactc agaaagagga gatggacaa  aaaataccga    180
aactggagca ccgcaactca acccaattga tgggccacta ccaaaagaca atgaaccaag    240
tggctatgcc caaacagatt gtgtattaga agcaatggct ttccttgagg aatcccatcc    300
tggtattttt gaaaactctt gtattgaaac aatggaggtt gttcagcaaa caagggtgga    360
caaactgaca caaggcagac agacctatga ctggactcta ataggaaacc agcctgctgc    420
cacagcattg gccaacacta tagaagtgtt cagatcaaac ggcctcatag caaatgaatc    480
tgggaggcta atagacttcc ttaaagatgt aatggagtcg atggacagag acgaagtaga    540
gatcacaact cattttcaaa gaagaggag  agtgagagac aatgtaacta aaaaaatggt    600
gacccaaaga acaataggca aaagaaaca  taaattagac aaaagaagtt acctaattag    660
ggcattaacc ctgaacacaa tgaccaaaga tgctgagagg gggaaactaa aacgcagagc    720
aattgcaacc ccaggaatgc aaataagggg gtttgtatac tttgttgaga cactggcaag    780
```

-continued

```
aagcatatgt gaaaagcttg aacaatcagg gttgccagtt ggaggaaatg aaaagaaagc    840
aaagttagca aatgttgtaa ggaagatgat gaccaactcc caggacactg aaatttcttt    900
caccatcact ggagataaca caaaatggaa cgaaaatcaa aaccctagaa tgttcttggc    960
catgatcaca tatataacca aaaatcagcc tgaatggttc agaaatattc taagtattgc   1020
tccaataatg ttttcaaaca aaatggcgag actaggtaag gggtacatgt tgaaagcaa    1080 gagtatgaaa ctgagaactc aaatacctgc agagatgcta gccaacatag atttgaaata   1140
tttcaatgat tcaactaaaa agaaaattga aaaaatccgg ccattattaa tagatggaac   1200
tgcatcattg agtcctggaa tgatgatggg catgttcaat atgttaagca ccgtcttggg   1260
cgtctccatt ctgaatcttg gcaaaagag atacaccaag actacttact ggtgggatgg    1320
tcttcaatcg tctgatgatt ttgctctgat tgtgaatgca cccaactatg caggaattca   1380
agctggagtt gacaggtttt atcgaacctg taagctgctc ggaattaata tgagcaaaaa   1440
gaagtcttac ataaacagaa caggtacctt tgagttcacg agcttttct atcgttatgg    1500 gtttgttgcc aatttcagca tggagcttcc tagttttggg gtgtctgggg tcaatgaatc   1560
tgcagacatg agtattggag tcactgtcat caaaaacaat atgataaaca atgaccttgg   1620
cccagcaact gctcaaatgg cccttcagtt atttataaaa gattacaggt acacgtatcg   1680
atgccacaga ggtgacacac aaatacaaac ccggagatca tttgagataa agaaactatg   1740
ggaccaaacc cgctccaaag ctgggctgtt ggtctctgat ggaggcccca atttatataa   1800
cattagaaat ctccatattc ctgaagtctg cttgaaatgg gagttgatgg atgaggatta   1860 ccagggggcgt ttatgcaacc cattgaaccc gtttgtcagt cataaagaga ttgaatcagt   1920
gaacaatgca gtgatgatgc cggcacatgg tccagccaaa aatatggagt atgacgctgt   1980
tgcaacaaca cactcctggg ttcccaaaag gaatcgatcc atttgaata cgagccaaag   2040 ggggatactt gaggatgagc aaatgtatca gaggtgctgc aatttatttg aaaaattctt   2100
cccaagtagc tcatacagaa gaccagtggg aatatccagt atggtagagg ctatggtttc   2160
cagagcccga attgatgcac ggattgattt cgaatctgga aggataaaaa agaggaatt    2220 cgctgagatc atgaagacct gttccaccat tgaagacctc agacggcaaa ataggggaat   2280
ttggcttgtc cttcatgaaa a                                              2301
```

<210> SEQ ID NO 3
<211> LENGTH: 2299
<212> TYPE: DNA
<213> ORGANISM: Influenza A virus

<400> SEQUENCE: 3

```
aatatggaaa gaataaaaga gctaaggaat ctgatgtcac aatctcgcac tcgcgagata     60
cttacaaaaa ctactgtaga ccacatggcc ataatcaaga atacacatc aggaagacag    120 gagaaaaacc catcacttag aatgaaatgg atgatggcaa tgaaataccc aattacagca   180
gataaaagga taacggaaat gattcctgaa agaaatgagc aaggacagac attatggagt   240
aaagtgaatg atgccggatc agaccgagtg atgatatcac ccctggctgt gacatggtgg   300
aacagaaatg accagtggc aagtactatt cactatccaa aaatctacaa aacttacttt   360
gaaaaggttg aaaggttaaa acatggaacc tttggccctg tacactttag aaaccaagtc   420
aaaatacgcc gaagagtcga cataaatcct ggtcatgcag acctcagcgc caaggaggca   480
caggatgtaa ttatgaagt tgttttccct aatgaagtgg gagccagaat actaacatca    540
gaatcgcaat taacgataac caaggagaaa aagaagaac tccagaattg caaaatttcc   600
```

```
cctttgatgg ttgcatacat gttagagagg gaacttgtcc gcaaaacgag atttctcccg      660
gttgctggtg aacaagcag tgtgtacatt gaagttttgc atttaacaca ggggacatgc      720
```
(Note: the second line above should read as shown in image)

```
cctttgatgg ttgcatacat gttagagagg gaacttgtcc gcaaaacgag atttctcccg      660
gttgctggtg aacaagcag tgtgtacatt gaagttttgc atttaacaca ggggacatgc      720
tgggagcaga tgtacactcc aggtgggag gtgaggaatg atgatgttga tcaaagccta      780
attattgctg ctaggaacat agtgagaaga gctgcagtat cagcagatcc actagcatct      840
ttattagaaa tgtgccatag cacacagatt ggtgggacaa ggatggtgga tattctcagg      900
caaaatccaa cagaagaaca agctgtggat atatgcaaag cagcaatggg gctgagaatc      960
agttcatcct tcagttttgg cggattcaca tttaagagaa caagtggatc atcagtcaaa     1020
agggaggaag aagtgctcac gggcaatctg caaacattga agctaactgt gcatgaggga     1080
tatgaagagt tcacaatggt tgggaaaagg gcaacagcta tactcagaaa agcaaccagg     1140
agattgattc aactaatagt gagtggaaga acgaacagt caatagtcga agcaatagtt     1200
gtagcaatgg tattctcaca agaagattgc atggtaaaag cagttagagg tgatctgaat     1260
ttcgttaata gagcgaatca gcggttgaat cccatgcatc aacttttgag acattttcag     1320
aaggatgcta aagtactttt cttaaattgg ggaattgaac ctatcgacaa tgtgatggga     1380
atgattggga tattacctga tatgactcca agtaccgaga tgtcaatgag gaagagtgaga     1440 gtcagcaaaa tgggtgtaga tgaatactcc aatgctgaaa gggtagtggt gagcattgac     1500
cgttttttga gagtccggga ccaaagagga aatgtactac tgtctccaga ggaagtcagt     1560
gaaacacagg gaacagagaa actgacaata acttactctt catcaatgat gtgggagatt     1620
aatggccctg agtcagtgtt gatcaatacc tatcagtgga tcatcagaaa ctgggagact     1680
gttaaaattc agtggtctca gaaccctaca atgctataca ataaaatgga attcgagcca     1740
tttcagtctc tagtccctaa ggccattaga ggccaataca gtgggtttgt tagaactcta     1800
tttcaacaaa tgagggatgt gcttgggacc tttgacacaa ctcagataat aaaacttctt     1860
ccctttgcag ccgctccacc aaagcaaagt agaatgcaat tctcatcatt gactgtgaat     1920
gtgaggggat caggaatgag aatacttgta aggggtaatt ctccagtatt caactacaac     1980
aagaccacta gagactcac agtcctcgga aaggatgctg gcactttaac tgaagaccca     2040
gatgaaggca cagctggagt ggaatctgct gttctaaggg gattcctcat tctaggcaaa     2100
gaagatagaa gatatgggcc agcattaagc atcaatgaat tgagcaacct tgcgaagggg     2160
gaaaaagcta atgtgctaat tgggcaaggg gacgtagtgt tggtaatgaa acgaaaacgg     2220
gactctagca tacttactga cagccagaca gcgaccaaaa gaattcggat ggccatcaat     2280
taatttcgaa taatttaaa                                                2299
```

<210> SEQ ID NO 4
<211> LENGTH: 1527
<212> TYPE: DNA
<213> ORGANISM: Influenza A virus

<400> SEQUENCE: 4

```
atcactcact

```
acaaagaaga aataaggcgg atttggcgcc aagccaacaa tggtgatgat gcaacggctg    420
gtttgactca cattatgatc tggcattcta atttgaatga tacaacttac cagaggacaa    480
gagctcttgt ccgcaccgga atggatccca ggatgtgctc tttgatgcaa ggttcaactc    540
tccctagaag atctggagca gcaggcgctg cagtcaaagg agttgggaca atggtgttgg    600
agttaatcag gatgatcaaa cgtgggatca atgaccgaaa cttctggagg ggtgagaatg    660
gaagaaaaac aaggattgct tatgagagaa tgtgcaacat tctcaaagga aaatttcaaa    720
cagctgcaca aaaagcaatg atggatcaag tgagagaaag ccggaaccca ggaaatgctg    780
agatcgaaga tctcactttt ctggcacggt ctgcactcat attaagaggg tcagttgctc    840
acaagtcttg cctgcctgcc tgtgtgtatg gaccagccgt agccagtggg tacgacttcg    900
aaaaagaggg atactctttg gtaggggtag acccttttaa actgcttcaa accagtcagg    960
tatacagcct aatcagacca aacgagaatc ccgcacacaa gagtcagttg gtgtggatgg   1020
catgcaattc tgctgcattt gaagatctaa gagtgtcaag cttcatcaga gggacaagag   1080
tacttccaag ggggaagctc tccactagag gagtacaaat tgcttcaaat gaaaacatgg   1140
atgctattgt atcaagtact cttgaactga aagcagata ctgggccata agaaccagaa    1200
gtggagggaa cactaatcaa caagggcct ctgcgggcca aatcagcaca aacctacgt     1260
tttctgtgca gagaaacctc ccatttgaca aaacaaccat catggcagca ttcactggga   1320
atacggaggg aagaacatca gacatgaggg cagaaatcat aaagatgatg gaaagtgcaa   1380
gaccagaaga agtgtccttc caggggcggg gagtctttga gctctcggac gaaagggcaa   1440
cgaacccgat cgtgccctcc tttgacatga gtaatgaagg atcttatttc ttcggagaca   1500
atgcagagga gtacgacaat taatgaa                                       1527

<210> SEQ ID NO 5
<211> LENGTH: 984
<212> TYPE: DNA
<213> ORGANISM: Influenza A virus

<400> SEQUENCE: 5
gatgagtctt ctaaccgagg tcgaaacgta cgttctctct atcgtcccgt caggccccct     60
caaagccgag atcgcacaga gacttgaaaa tgtctttgct ggaaagaata ccgatcttga    120
ggctctcatg gaatggctaa agacaagacc aatcctgtca cctctgacta aggggatttt    180
aggatttgtg ttcacgctca ccgtgcccag tgagcgagga ctgcagcgta gacgctttgt    240
ccaaaatgcc cttaatggga atggggatcc aaataatatg gacagagcag ttaaactgta    300
tcgaaagctt aagagggaga taacattcca tggggccaaa gaaatagcac tcagttattc    360
tgctggtgca cttgccagtt gtatgggact catatacaac aggatggggg ctgtgaccac    420
cgaatcagca tttggcctta tatgcgcaac ctgtgaacag attgccgact cccagcataa    480
gtctcatagg caaatggtaa caacaaccaa cccattaata agacatgaga acagaatggt    540
tctggccagc actacagcta aggctatgga gcaaatggct ggatcgagtg aacaagcagc    600
tgaggccatg gaggttgcta gtcaggccag gcagatggtg caggcaatga gagccattgg    660
gactcatcct agctctagca ctggtctgaa aaatgatctc cttgaaaatt tgcaggccta    720
tcagaaacga atgggggtgc agatgcaacg attcaagtga tcctcttgtt gttgccgcaa    780
gtataattgg gattgtgcac ctgatattgt ggattattga tcgcctttt tccaaaagca    840
tttatcgtat ctttaaacac ggtttaaaaa gagggccttc tacggaagga gtaccagagt    900
ctatgaggga agaatatcga gaggaacagc agaatgctgt ggatgctgac gatggtcatt    960
```
ttgtcagcat agagctagag taaa                                               984

<210> SEQ ID NO 6
<211> LENGTH: 844
<212> TYPE: DNA
<213> ORGANISM: Influenza A virus

<400> SEQUENCE: 6
atggattccc acactgtgtc aagctttcag gtagattgct cctttggca tgtccgcaaa         60 caagttgcag accaagatct aggcgatgcc ccattccttg atcggcttcg ccgagatcag       120
aagtctctaa agggaagagg cagcactctc ggtctgaaca tcgaaacagc cacttgtgtt       180
ggaaagcaaa tagtagagag gattctgaaa gaagaatccg atgaggcatt taaaatgacc       240
atggcctccg cacttgcttc gcggtaccta actgacatga ctattgaaga atgtcaagg        300 gactggttca tgctcatgcc caagcagaaa gtggctggcc ctctttgtgt cagaatggac       360
caggcgataa tggataagaa catcatactg aaagcgaatt tcagtgtgat ttttgaccgg       420
ttggagaatc tgacattact aagggctttc accgaagagg gagcaattgt tggcgaaatt       480
tcaccattgc cttctcttcc aggacatact aatgaggatg tcaaaaatgc aattggggtc       540
ctcatcgggg gacttgaatg gaatgataac acagttcgag tctctgaaac tctacagaga       600
ttcgcttgga gaagcagtaa tgagactggg ggacctccat tcactccaac acagaaacgg       660
aaaatggcgg gaacaattag gtcagaagtt tgaagaaata agatggctga ttgaagaagt       720
gaggcataaa ttgaagacga cagagaatag ttttgagcaa ataacattta tgcaagcatt       780
acagctattg tttgaagtgg aacaagagat tagaacgttt tcgtttcagc ttatttaatg       840
ataa                                                                    844

<210> SEQ ID NO 7
<211> LENGTH: 1728
<212> TYPE: DNA
<213> ORGANISM: Influenza A virus

<400> SEQUENCE: 7
ccaaaatgaa agcaaaacta ctggtcctgt tatgtacatt tacagctaca tatgcagaca         60
caatatgtat aggctaccat gccaacaact caaccgacac tgttgacaca gtacttgaga       120
agaatgtgac agtgacacac tctgtcaacc tacttgagga cagtcacaat ggaaaactat       180
gtctactaaa aggaatagcc ccactacaat tgggtaattg cagcgttgcc ggatggatct       240
taggaaaccc agaatgcgaa ttactgattt ccaaggaatc atggtcctac attgtagaaa       300
caccaaatcc tgagaatgga acatgttacc cagggtattt cgccgactat gaggaactga       360
gggagcaatt gagttcagta tcttcatttg agagattcga atattccccc aaagaaagct       420
catggcccaa ccacaccgta accggagtat cagcatcatg ctcccataat gggaaaagca       480
gtttttacag aaatttgcta tggctgacgg ggaagaatgg tttgtaccca aacctgagca       540
agtcctatgt aaacaacaaa gagaagaag tccttgtact atggggtgtt catcacccgc       600
ctaacatagg gaaccaaagg gccctctatc atacagaaaa tgcttatgtc tctgtagtgt       660
cttcacatta tagcagaaga ttcacccag aaatagccaa aagacccaaa gtaagagatc        720
aggaaggaag aatcaactac tactggactc tgctggaacc tggggataca ataatatttg       780
aggcaaatgg aaatctaata gcgccatggt atgcttttgc actgagtaga ggctttggat       840
caggaatcat cacctcaaat gcaccaatgg atgaatgtga tgcgaagtgt caaacacctc       900

| | |
|---|---|
| agggagctat aaacagcagt cttcctttcc agaatgtaca cccagtcaca ataggagagt | 960 |
| gtccaaagta tgtcaggagt gcaaaattaa ggatggttac aggactaagg aacatcccat | 1020 |
| ccattcaatc cagaggtttg tttggagcca ttgccggttt cattgaaggg gggtggactg | 1080 |
| gaatggtaga tgggtggtat ggttatcatc atcagaatga gcaaggatct ggctatgctg | 1140 |
| cagatcaaaa aagtacacaa atgccatta acgggattac aaacaaggtg aattctgtaa | 1200 |
| ttgagaaaat gaacactcaa ttcacagctg tgggcaaaga attcaacaaa ttggaaagaa | 1260 |
| ggatggaaaa cttaaataaa aaagttgatg atgggtttct agacatttgg acatataatg | 1320 |
| cagaattgtt ggttctactg gaaaatgaaa ggactttgga tttccatgac tccaatgtga | 1380 |
| agaatctgta tgagaaagta aaaagccaat taaagaataa tgccaaagaa ataggaaacg | 1440 |
| ggtgttttga attctatcac aagtgtaaca atgaatgcat ggagagtgtg aaaaatggaa | 1500 |
| cttatgacta tccaaaatat tccgaagaat caaagttaaa cagggagaaa attgatggag | 1560 |
| tgaaattgga atcaatggga gtctatcaga ttctggcgat ctactcaact gtcgccagtt | 1620 |
| ccctggttct tttggtctcc ctgggggcaa tcagcttctg gatgtgttcc aatgggtctt | 1680 |
| tgcagtgtag aatatgcatc tgagaccaga atttcagaaa tataagaa | 1728 |

<210> SEQ ID NO 8
<211> LENGTH: 1414
<212> TYPE: DNA
<213> ORGANISM: Influenza A virus

<400> SEQUENCE: 8

| | |
|---|---|
| aatgaatcca atcaaaaaa taataaccat tggatcaatc agtatagcaa tcggaataat | 60 |
| tagtctaatg ttgcaaatag gaaatattat ttcaatatgg gctagtcact caatccaaac | 120 |
| tggaagtcaa aaccacactg gagtatgcaa ccaaagaatc atcacatatg aaaacagcac | 180 |
| ctgggtgaat cacacatatg ttaatattaa caacactaat gttgttgctg gaaaggacaa | 240 |
| aacttcagtg acattggccg gcaattcatc tctttgttct atcagtggat gggctatata | 300 |
| cacaaaagac aacagcataa gaattggctc caaaggagat gttttgtca agagagaacc | 360 |
| tttcatatca tgttctcact ggaatgcag aaccttttttt ctgacccaag gtgctctatt | 420 |
| aaatgacaaa cattcaaatg ggaccgttaa ggacagaagt ccttataggg ccttaatgag | 480 |
| ctgtcctcta ggtgaagctc cgtcccata caattcaaag tttgaatcag ttgcatggtc | 540 |
| agcaagcgca tgccatgatg gcatgggctg gttaacaatc ggaatttctg gtccagacaa | 600 |
| tggagctgtg gctgtactaa aatacaacgg cataataact gaaaccataa aaagttggaa | 660 |
| aaagcgaata ttaagaacac aagagtctga atgtgtctgt gtgaacgggt catgttttac | 720 |
| cataatgacc gatggcccga gtaatgggc cgcctcgtac aaaatcttca agatcgaaaa | 780 |
| ggggaaggtt actaaatcaa tagagttgaa tgcacccaat tttcattatg aggaatgttc | 840 |
| ctgttacccca gacactggca cagtgatgtg tgtatgcagg acaactggc atggttcaaa | 900 |
| tcgaccttgg gtgtctttta atcaaaacct ggattatcaa ataggataca tctgcagtgg | 960 |
| ggtgttcggt gacaatccgc gtcccaaaga tggagagggc agctgtaatc cagtgactgt | 1020 |
| tgatggagca gacggagtaa agggttttc atacaaatat ggtaatgtg tttgataagg | 1080 |
| aaggactaaa agtaacagac ttagaaaggg gttttgagatg atttgggatc ctaatggatg | 1140 |
| gacagatacc gacagtgatt tctcagtgaa acaggatgtt gtggcaataa ctgattggtc | 1200 |
| agggtacagc ggaagtttcg ttcaacatcc tgagttaaca ggattggact gtataagacc | 1260 |
| ttgcttctgg gttgagttag tcagaggact gcctagagaa aatacaacaa tctggactag | 1320 |

-continued tgggagcagc atttcttttt gtggcgtaaa tagtgatact gcaaactggt cttggccaga 1380
cggtgctgag ttgccgttca ccattgacaa gtag 1414

<210> SEQ ID NO 9
<211> LENGTH: 2233
<212> TYPE: DNA
<213> ORGANISM: Influenza A virus

<400> SEQUENCE: 9
agcgaaagca ggtactgatc caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agattttcac 180
ttcatcaatg agcaaggcga gtcaataatc gtagaacttg gtgatccaaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggagaata gatttatcga aattggagta acaaggagag aagttcacat atactatctg 420
gaaaaggcca ataaaattaa atctgagaaa acacacatcc acattttctc gttcactggg 480
gaagaaatgg ccacaaaggc agactacact ctcgatgaag aaagcagggc taggatcaaa 540
accagactat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc tttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaagaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagtttaac 1260
aaggcatgcg aactgacaga ttcaagctgg atagagctcg atgagattgg agaagatgtg 1320
gctccaattg aacacattgc aagcatgaga aggaattatt tcacatcaga ggtgtctcac 1380
tgcagagcca cagaatacat aatgaagggg gtgtacatca atactgcctt gcttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacata aatgggagaa gtactgtgtt cttgagatag gagatatgct tataagaagt 1680
gccataggcc aggtttcaag gcccatgttc ttgtatgtga gaacaaatgg aacctcaaaa 1740
attaaaatga aatggggaat ggagatgagg cgttgcctcc tccagtcact tcaacaaatt 1800
gagagtatga ttgaagctga gtcctctgtc aaagagaaag acatgaccaa agagttcttt 1860
gagaacaaat cagaaacatg gcccattgga gagtccccca aaggagtgga ggaaagttcc 1920
attgggaagg tctgcaggac tttattagca aagtcggtat tcaacagctt gtatgcatct 1980

```
ccacaactag aaggatttttc agctgaatca agaaaactgc ttcttatcgt tcaggctctt      2040
agggacaacc ttgaacctgg gacctttgat cttgggggc tatatgaagc aattgaggag        2100
tgcctgatta atgatccctg ggttttgctt aatgcttctt ggttcaactc cttccttaca       2160
catgcattga gttagttgtg gcagtgctac tatttgctat ccatactgtc caaaaaagta       2220
ccttgtttct act                                                          2233

<210> SEQ ID NO 10
<211> LENGTH: 2341
<212> TYPE: DNA
<213> ORGANISM: Influenza A virus

<400> SEQUENCE: 10
agcgaaagca ggcaaaccat ttgaatggat gtcaatccga ccttactttt cttaaaagtg         60
ccaacacaaa atgctataag cacaactttc ccttatactg gagaccctcc ttacagccat        120
gggacaggaa caggatacac catggatact gtcaacagga cacatcagta ctcagaaaag        180
ggaagatgga caacaaacac cgaaactgga gcaccgcaac tcaacccgat tgatgggcca        240
ctgccagaag acaatgaacc aagtggttat gcccaaacag attgtgtatt ggaggcgatg        300
gctttccttg aggaatccca tcctggtatt tttgaaaact cgtgtattga acgatggag         360 gttgttcagc aaacacgagt agacaagctg acacaaggcc gacagaccta tgactggact        420
ctaaatagaa accaacctgc tgcaacagca ttggccaaca atagaagt gttcagatca         480 aatggcctca cggccaatga gtctggaagg ctcatagact ccttaaggga tgtaatggag        540
tcaatgaaca agaagaaat ggggatcaca actcattttc agagaaagag acgggtgaga          600
gacaatatga ctaagaaaat gataacacag agaacaatgg gtaaaaagaa gcagagattg        660
aacaaaagga gttatctaat tagagcattg accctgaaca caatgaccaa agatgctgag        720
agagggaagc taaaacggag agcaattgca accccaggga tgcaaataag ggggtttgta        780
tactttgttg agacactggc aaggagtata tgtgagaaac ttgaacaatc agggttgcca        840
gttggaggca atgagaagaa agcaaagttg gcaaatgttg taaggaagat gatgaccaat        900
tctcaggaca ccgaactttc tttcaccatc actggagata caccaaatg gaacgaaaat         960 cagaatcctc ggatgttttt ggccatgatc acatatatga ccagaaatca gccgaatgg        1020 ttcagaaatg ttctaagtat tgctccaata atgttctcaa acaaaatggc gagactggga       1080 aagggtata tgtttgagag caagagtatg aaacttagaa ctcaaatacc tgcagaaatg        1140
ctagcaagca tcgatttgaa atatttcaat gattcaacaa gaagaagat tgaaaaaatc       1200 cgaccgctct aatagaggg gactgcatca ttgagccctg aatgatgat gggcatgttc        1260 aatatgttaa gcactgtatt aggcgtctcc atcctgaatc ttggacaaaa gagatacacc      1320
aagactactt actggtggga tggtcttcaa tcctctgacg attttgctct gattgtgaat      1380
gcacccaatc atgaagggat tcaagccgga gtcgacaggt tttatcgaac ctgtaagcta      1440
cttggaatca atatgagcaa gaaaaagtct tacataaaca gaacaggtac atttgaattc      1500
acaagttttt tctatcgtta tgggtttgtt gccaatttca gcatggagct tcccagtttt      1560
ggggtgtctg gatcaacga gtcagcggac atgagtattg gagttactgt catcaaaaac      1620
aatatgataa acaatgatct tggtccagca acagctcaaa tggcccttca gttgttcatc       1680
aaagattaca ggtacacgta ccgatgccat agaggtgaca cacaaataca aacccgaaga       1740
tcatttgaaa taagaaact gtgggagcaa accgttccaa agctggact gctggtctcc       1800 gacggaggcc caatttata caacattaga aatctccaca ttcctgaagt ctgcctaaaa       1860
```

| | |
|---|---|
| tgggaattga tggatgagga ttaccagggg cgtttatgca acccactgaa cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatccccaa agaaatcga | 2040 |
| tccatcttga atacaagtca aagaggagta cttgaggatg aacaaatgta ccaaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 11
<211> LENGTH: 2341
<212> TYPE: DNA
<213> ORGANISM: Influenza A virus

<400> SEQUENCE: 11

| | |
|---|---|
| agcgaaagca ggtcaattat attcaatatg gaaagaataa agaactaag aaatctaatg | 60 |
| tcgcagtctc gcacccgcga gatactcaca aaaaccaccg tggaccatat ggccataatc | 120 |
| aagaagtaca catcaggaag acaggagaag aacccagcac ttaggatgaa atggatgatg | 180 |
| gcaatgaaat atccaattac agcagacaag aggataacgg aaatgattcc tgagagaaat | 240 |
| gagcaaggac aaactttatg gagtaaaatg aatgatgccg gatcagaccg agtgatggta | 300 |
| tcacctctgg ctgtgacatg gtggaatagg aatggaccaa taacaaatac agttcattat | 360 |
| ccaaaaatct acaaaactta ttttgaaaga gtagaaaggc taaagcatgg aaccttttggc | 420 |
| cctgtccatt ttagaaacca agtcaaaata cgtcggagag ttgacataaa tcctggtcat | 480 |
| gcagatctca gtgccaagga ggcacaggat gtaatcatgg aagttgtttt ccctaacgaa | 540 |
| gtgggagcca ggatactaac atcggaatcg caactaacga taaccaaaga gaagaaagaa | 600 |
| gaactccagg attgcaaaat ttctcctttg atggttgcat acatgttgga gagagaactg | 660 |
| gtccgcaaaa cgagattcct cccagtggct ggtggaacaa gcagtgtgta cattgaagtg | 720 |
| ttgcatttga ctcaaggaac atgctgggaa cagatgtata ctccaggagg ggaagtgagg | 780 |
| aatgatgatg ttgatcaaag cttgattatt gctgctagga cataagtgag aagagctgca | 840 |
| gtatcagcag atccactagc atctttattg gagatgtgcc acagcacaca gattggtgga | 900 |
| attaggatgg tagacatcct taggcagaac ccaacagaag agcaagccgt ggatatatgc | 960 |
| aaggctgcaa tgggactgag aattagctca tccttcagtt ttggtggatt cacatttaag | 1020 |
| agaacaagcg gatcatcagt caagagagag gaagaggtgc ttacgggaaa tcttcaaaca | 1080 |
| ttgaagataa gagtgcatga gggatatgaa gagttcacaa tggttgggag aagagcaaca | 1140 |
| gccatactca gaaaagcaac caggagattg attcagctga tagtgagtgg gagagacgaa | 1200 |
| cagtcgattg ccgaagcaat aattgtggcc atggtatttt cacaagagga ttgtatgata | 1260 |
| aaagcagtca gaggtgatct gaatttcgtc aatagggcga atcagcgatt gaatcctatg | 1320 |
| catcaacttt aagacatttt tcagaaggat gcgagagtgc ttttttcaaaa ttggggagtt | 1380 |
| gaacctatcg acaatgtgat gggaatgatt gggatattgc ccgacatgac tccaagcatc | 1440 |
| gagatgtcaa tgagaggagt gagaatcagc aaaaatgggtg tagatgagta ctccagcacg | 1500 |
| gagagggtag tggtgagcat tgaccgtttt ttgagaatcc gggaccaacg aggaaatgta | 1560 |

```
ctactgtctc ccgaggaggt cagtgaaaca cagggaacag agaaactgac ataacttac      1620 tcatcgtcaa tgatgtggga gattaatggt cctgaatcag tattggtcaa tacctatcaa     1680
tggatcatca gaaactggga aactgttaaa attcagtggt cccagaaccc tacaatgcta     1740
tacaataaaa tggaatttga accatttcag tctttagtac taaggccat tagaggccaa      1800 tacagtgggt ttgtaagaac tctgttccaa caaatgaggg atgtgcttgg acatttgat     1860 accgcacaga taataaaact tcttcccttc gcagccgctc caccaaagca agtagaatg      1920 cagttctcct catttactgt gaatgtgagg ggatcaggaa tgagaatact tgtaaggggc     1980
aattctcctg tattcaacta taacaaggcc acgaagagac tcacagttct cggaaaggat    2040
gctggcactt taactgaaga cccagatgaa ggcacagctg gagtggagtc cgctgttctg    2100
aggggattcc tcattctggg caaagaagac aagagatatg gccagcact aagcatcaat      2160 gaactgagca accttgcgaa aggagagaag gctaatgtgc taattgggca aggagacgtg    2220
gtgttggtaa tgaaacggaa acgggactct agcatactta ctgacagcca gacagcgacc    2280
aaaagaattc ggatggccat caattagtgt cgaatagttt aaaaacgacc ttgtttctac    2340
t                                                                      2341

<210> SEQ ID NO 12
<211> LENGTH: 1565
<212> TYPE: DNA
<213> ORGANISM: Influenza A virus

<400> SEQUENCE: 12
agcaaaagca gggtagataa tcactcactg agtgacatca aaatcatggc gtctcaaggc       60
accaaacgat cttacgaaca gatggagact gatggagaac gccagaatgc cactgaaatc      120
agagcatccg tcggaaaaat gattggtgga attggacgat tctacatcca aatgtgcacc      180
gaactcaaac tcagtgatta tgagggacgg ttgatccaaa acagcttaac aatagagaga      240
atggtgctct ctgcttttga cgaaaggaga ataaatacc ttgaagaaca tcccagtgcg       300
ggaaaagatc ctaagaaaac tggaggacct atatacagga gagtaaacgg aaagtggatg      360
agagaactca tcctttatga caaagaagaa ataaggcgaa tctggcgcca agctaataat      420
ggtgacgatg caacggctgg tctgactcac atgatgatct ggcattccaa tttgaatgat      480
gcaacttatc agaggacaag agctcttgtt cgcaccggaa tggatcccag atgtgctct      540 ctgatgcaag gttcaactct ccctaggagg tctggagccg caggtgctgc agtcaaagga      600
gttggaacaa tggtgatgga attggtcaga atgatcaaac gtgggatcaa tgatcggaac      660
ttctggaggg gtgagaatgg acgaaaaaca agaattgctt atgaaagaat gtgcaacatt      720
ctcaaaggga aatttcaaac tgctgcacaa aaagcaatga tggatcaagt gagagagagc     780
cggaacccag ggaatgctga gttcgaagat ctcacttttc tagcacggtc tgcactcata     840
ttgagagggt cggttgctca caagtcctgc ctgcctgcct gtgtgtatgg acctgccgta    900
gccagtgggt acgactttga aagggaggga tactctctag tcggaataga cccttttcaga   960 ctgcttcaaa acagccaagt gtacagccta atcagaccaa atgagaatcc agcacacaag   1020
agtcaactgg tgtggatggc atgccattct gccgcatttg aagatctaag agtattaagc   1080
ttcatcaaag ggacgaaggt gctcccaaga gggaagcttt ccactagagg agttcaaatt   1140
gcttccaatg aaaatatgga gactatggaa tcaagtacac ttgaactgag aagcaggtac   1200
tgggccataa ggaccagaag tggaggaaac accaatcaac agagggcatc tgcgggccaa   1260
atcagcatac aacctacgtt ctcagtacag agaaatctcc cttttgacag aacaaccatt   1320
```

```
atggcagcat tcaatgggaa tacagagggg agaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500
tcttatttct cggagacaat gcagaggag tacgacaatt aaagaaaaat accttgttt     1560 ctact                                                                1565
```

<210> SEQ ID NO 13
<211> LENGTH: 1027
<212> TYPE: DNA
<213> ORGANISM: Influenza A virus

<400> SEQUENCE: 13

```
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggacggggg atccaaataa    300
catggacaaa gcagttaaac tgtataggaa gctcaagagg gagataacat tccatggggc    360
caaagaaatc tcactcagtt attctgctgg tgcacttgcc agttgtatgg cctcatata    420 caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcaaga acgaatgggg gtgcagatgc aacggttcaa    780
gtgatcctct cactattgcc gcaaatatca ttgggatctt gcacttgaca ttgtggattc    840
ttgatcgtct ttttttcaaa tgcatttacc gtcgctttaa atacggactg aaaggagggc    900
cttctacgga aggagtgcca agtctatga gggaagaata tcgaaggaa cagcagagtg    960 ctgtggatgc tgacgatggt cattttgtca gcatagagct ggagtaaaaa actaccttgt    1020
ttctact                                                              1027
```

<210> SEQ ID NO 14
<211> LENGTH: 890
<212> TYPE: DNA
<213> ORGANISM: Influenza A virus

<400> SEQUENCE: 14

```
agcaaaagca gggtgacaaa aacataatgg atccaaacac tgtgtcaagc tttcaggtag      60
attgctttct ttggcatgtc cgcaaacgag ttgcagacca agaactaggt gatgccccat    120
tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct tgtatcaga atggaccagg cgatcatgga taagaacatc atactgaaag    420
cgaacttcag tgtgattttt gaccggctgg agactctaat attgctaagg gctttcaccg    480
```

| | |
|---|---:|
| aagagggagc aattgttggc gaaatttcac cattgccttc tcttccagga catactgctg | 540 |
| aggatgtcaa aaatgcagtt ggagtcctca tcggaggact tgaatggaat gataacacag | 600 |
| ttcgagtctc tgaaactcta cagagattcg cttggagaag cagtaatgag aatgggagac | 660 |
| ctccactcac tccaaaacag aaacgagaaa tggcgggaac aattaggtca gaagtttgaa | 720 |
| gaaataagat ggttgattga agaagtgaga cacaaactga agataacaga gaatagtttt | 780 |
| gagcaaataa catttatgca agccttacat ctattgcttg aagtggagca agagataaga | 840 |
| actttctcgt ttcagcttat ttagtactaa aaaacaccct tgtttctact | 890 |

<210> SEQ ID NO 15
<211> LENGTH: 1775
<212> TYPE: DNA
<213> ORGANISM: Influenza A virus

<400> SEQUENCE: 15

| | |
|---|---:|
| agcaaaagca ggggaaaata aaaacaacca aaatgaaggc aaacctactg gtcctgttat | 60 |
| gtgcacttgc agctgcagat gcagacacaa tatgtatagg ctaccatacg aacaattcaa | 120 |
| ccgacactgt tgacacagta ctcgagaaga atgtgacagt gacacactct gttaacctgc | 180 |
| tcgaagacag ccacaacgga aaactatgta ttattaaaagg aatagcccca ctacaattgg | 240 |
| ggaaatgtaa catcgccgga tggctcttgg gaaacccaga atgcgaccca ctgcttccag | 300 |
| tgagatcatg gtcctacatt gtagaaacac caaactctga atgaatgaata tgttatccag | 360 |
| gagatttcat cgactatgag gagctgaggg agcaattgag ctcagtgtca tcattcgaaa | 420 |
| gattcgaaat atttcccaaa gaaagctcat ggcccaacca caacacaaac ggagtaacgg | 480 |
| cagcatgctc ccatgagggg aaaagcagtt tttacagaaa tttgctatgg ctgacggaga | 540 |
| aggagggctc atacccaaag ctgaaaaatt cttatgtgaa caaaaaaggg aaagaagtcc | 600 |
| ttgtactgtg gggtattcat cacccgccta acagtaagga caacagaat ctctatcaga | 660 |
| atgaaaatgc ttatgtctct gtagtgactt caaattataa caggagattt accccgaaa | 720 |
| tagcagaaag acccaaagta agagatcaag ctgggaggat gaactattac tggaccttgc | 780 |
| taaaacccgg agacacaata atatttgagg caaatgaaa tctaatagca ccaatgtatg | 840 |
| ctttcgcact gagtagaggc tttgggtccg gcatcatcac ctcaaacgca tcaatgcatg | 900 |
| agtgtaacac gaagtgtcaa acaccctgg gagctataaa cagcagtctc ccttaccaga | 960 |
| atatacaccc agtcacaata ggagagtgcc caaaatacgt caggagtgcc aaattgagga | 1020 |
| tggttacagg actaaggaac attccgtcca ttcaatccag aggtctattt ggagccattg | 1080 |
| ccggtttat tgaaggggga tggactggaa tgatagatgg atggtatggt tatcatcatc | 1140 |
| agaatgaaca gggatcaggc tatgcagcgg atcaaaaaag cacacaaaat gccattaacg | 1200 |
| ggattacaaa caaggtgaac actgttatcg agaaaatgaa cattcaattc acagctgtgg | 1260 |
| gtaaagaatt caacaaatta gaaaaaagga tggaaatttt aataaaaaa gttgatgatg | 1320 |
| gatttctgga catttggaca tataatgcag aattgttagt tctactggaa aatgaaagga | 1380 |
| ctctggaatt ccatgactca aatgtgaaga atctgtatga aaagtaaaaa agccaattaa | 1440 |
| agaataatgc caagaaatc ggaaatggat gttttgagtt ctaccacaag tgtgacaatg | 1500 |
| aatgcatgga aagtgtaaga aatgggactt atgattatcc caaatattca gaagagtcaa | 1560 |
| agttgaacag ggaaaaggta gatggagtga aattggaatc aatggggatc tatcagattc | 1620 |
| tggcgatcta ctcaactgtc gccagttcac tggtgctttt ggtctccctg ggggcaatca | 1680 |
| gtttctggat gtgttctaat ggatctttgc agtgcagaat atgcatctga gattagaatt | 1740 |

```
tcagagatat gaggaaaaac acccttgttt ctact                           1775
```

<210> SEQ ID NO 16
<211> LENGTH: 1413
<212> TYPE: DNA
<213> ORGANISM: Influenza A virus

<400> SEQUENCE: 16

```
agcaaaagca ggggtttaaa atgaatccaa atcagaaaat aataaccatt ggatcaatct   60
gtctggtagt cggactaatt agcctaatat tgcaaatagg gaatataatc tcaatatgga  120
ttagccattc aattcaaact ggaagtcaaa accatactgg aatatgcaac caaacatca   180
ttacctataa aaatagcacc tgggtaaagg acacaacttc agtgatatta accggcaatt  240
catctctttg tcccatccgt gggtgggcta tatacagcaa agacaatagc ataagaattg  300
gttccaaagg agacgttttt gtcataagag agccctttat ttcatgttct cacttggaat  360
gcaggacctt ttttctgacc caaggtgcct tactgaatga caagcattca agtgggactg  420
ttaaggacag aagcccttat agggccttaa tgagctgccc tgtcggtgaa gctccgtccc  480
cgtacaattc aagatttgaa tcggttgctt ggtcagcaag tgcatgtcat gatggcatgg  540
gctggctaac aatcggaatt tcaggtccag ataatggagc agtggctgta ttaaaataca  600
acggcataat aactgaaacc ataaaaagtt ggaggaagaa atattgagg acacaagagt  660
ctgaatgtgc ctgtgtaaat ggttcatgtt ttactataat gactgatggc ccgagtgatg  720
ggctggcctc gtacaaaatt ttcaagatcg aaaaggggaa ggttactaaa tcaatagagt  780
tgaatgcacc taattctcac tatgaggaat gttcctgtta ccctgatacc gacaaagtga  840
tgtgtgtgtg cagagacaat tggcatggtt cgaaccggcc atgggtgtct ttcgatcaaa  900
acctggatta tcaaatagga tacatctgca gtggggtttt cggtgacaac ccgcgtcccg  960
aagatggaac aggcagctgt ggtccagtgt atgttgatgg agcaaacgga gtaaagggat 1020
tttcatatag gtatggtaat ggtgtttgga taggaaggac caaaagtcac agttccagac 1080
atgggtttga tgatttggg atcctaatg atggacaga gactgatagt aagttctctg 1140
tgaggcaaga tgttgtggca atgactgatt ggtcagggta tagcggaagt ttcgttcaac 1200
atccctgagct gacagggcta gactgtatga ggccgtgctt ctgggttgaa ttaatcaggg 1260
gacgacctaa agaaaaaaca atctggacta gtgcgagcag catttctttt tgtgcgtga 1320
atagtgatac tgtagattgg tcttggccag acggtgctga gttgccattc agcattgaca 1380
agtagtctgt tcaaaaaact ccttgtttct act                             1413
```

<210> SEQ ID NO 17
<211> LENGTH: 2220
<212> TYPE: DNA
<213> ORGANISM: Influenza A virus

<400> SEQUENCE: 17

```
agcgaaagca ggtactgatt cgaaatggaa gattttgtgc gacaatgctt caatccgatg   60
attgtcgagc ttgcggaaaa ggcaatgaaa gagtatggag aggacctgaa atcgaaaca  120
aacaaatttg cagcaatatg cacccacttg gaagtatgct tcatgtattc agattttcat  180
ttcatcaatg agcaaggcga atcaataata gtagagcctg gagacccaaa tgcacttta   240
aaacacagat ttgagataat agagggggcga gatcgtacaa tggcatggac agttgtaaac  300
agtatttgca acaccacagg agctgagaaa ccaaagtttc tgccagatct gtatgattac  360
```

-continued

```
aaagagaata ggttcatcga aattggagtg acaaggagag aagttcacat atactatctg    420
gaaaaggcca acaaaattaa atctgagaag acacatattc acattttctc atttactggc    480
gaagaaatgg ccacaaaggc cgattacact ctcgatgaag aaagcagggc tagaattaaa    540
accagactat tcaccataag gcaagaaatg gcaagcagag gtctttggga ctcctttcgt    600
cagtccgaaa gaggcgaaga gacaattgaa gaaaggtttg aaatcacagg gacaatgcgc    660
aggctcgctg atcaaagcct tccgccgaac ttctcctgca ttgagaattt tagagcctat    720
gtggatggat ttgaaccgaa cggctacatt gagggcaagc tttctcaaat gtccaaagaa    780
gtaaatgcta aaattgagcc tttttttgaaa acaacacctc gaccaattag acttccgaat    840
gggcctcctt gttttcagcg gtcaaaattc ctgctgatgg attctttaaa attaagcatt    900
gaggatccaa atcatgaagg ggagggaata ccactatatg atgcaatcaa gtgtatgaga    960
acattctttg gatggaaaga acccactgtt gtcaagccac acgagaaggg aataaatccg   1020
aattatctgc tgtcgtggaa gcaggtgttg gaagagctgc aggacattga gagtgaggag   1080
aagattccaa gaacaaaaaa catgaaaaaa acgagtcagt taaagtgggc acttggtgag   1140
aacatggcac cagagaaggt ggattttgat gactgtaaag atataagcga tttgaagcaa   1200
tatgatagtg acgaacctga attaaggtca ttttcaagtt ggatccagaa tgagttcaac   1260
aaggcatgcg agctgaccga ttcaatctgg atagagctcg atgagattgg agaagatgtg   1320
gccccgattg aacacattgc aagcatgaga agaaattact tcacagctga ggtgtcccat   1380
tgcagagcca ctgaatatat aatgaaaggg gtatacatta atactgcttt gcttaatgca   1440
tcctgtgcag caatggatga tttccaacta attcctatga taagcaaatg tagaactaaa   1500
gagggaagga gaaagaccaa tttgtacggc ttcatcataa aaggaagatc tcacttaagg   1560
aatgataccg atgtggtaaa ctttgtgagc atggagtttt ccctcactga cccaagactt   1620
gagccacaca aatgggagaa gtactgtgtt cttgagatag gagatatgct tctaaggagt   1680
gcaataggcc aagtgtcaag gcccatgttc ttgtatgtaa gaacaaatgg aacctcaaaa   1740
attaaaatga aatggggaat ggagatgagg cgttgcctcc tccaatccct ccaacaaata   1800
gagagcatga ttgaagctga gtcctctgtc aaggagaaag acatgacaaa agagtttttt   1860
gagaatagat cagaaacatg gcccattgga gagtcaccaa aaggagtgga agaaggttcc   1920
attgggaaag tatgcaggac actattggct aaatcagtat tcaatagtct gtatgcatct   1980
ccacaattag aaggattttc agctgagtca agaaagttgc tccttattgt tcaggctctt   2040
agggacaatc tggaacctgg gacctttgat cttgggggac tatatgaagc aattgaggag   2100
tgcctgatta atgatccctg ggttttgctt aatgcttctt ggttcaactc cttcctaaaa   2160
catgcattga gatagctgag gcaatgctac tatttgttat ccatactgtc caaaaaagta   2220
```

<210> SEQ ID NO 18
<211> LENGTH: 2341
<212> TYPE: DNA
<213> ORGANISM: Influenza A virus

<400> SEQUENCE: 18

```
agcgaaagca ggcaaaccat ttgaatggat gtcaatccga cattactttt cttaaaagtg     60
ccagcacaaa atgctataag cacaactttt ccttatactg gtgaccctcc ttacagccat    120
ggaacaggaa caggatacac catggataca gtcaacagga cacatcagta ctcagaaaga    180
ggaagatgga cgaaaaatac cgaaactgga gcaccgcaac tcaacccaat tgatgggcca    240
ctaccagaag acaatgaacc aagtggctat gcccaaacag attgtgtatt agaggcaatg    300
```

```
gctttccttg aagaatccca tcctggtatt tttgaaaact cttgtattga aacaatggag      360
gttgttcagc aaacaagggt ggacaaactg acacaaggca gacaaaccta tgactggact      420
ctaaatagga accagcctgc tgccacagca ttggcaaaca ccatagaagt attcagatca      480
aatggcctca tagcaaatga atctggaagg ctaatagact tccttaaaga tgtaatggag      540
tcgatggaca gagacgaagt agaggtcaca actcattttc aaagaaagag gagagtgaga      600
gacaatgtaa ctaaaaaaat ggtgacccaa agaacaatag gaaaaagaa acataaatta       660 gacaaaagaa gttacctaat tagggcatta accctgaaca caatgaccaa agatgctgag      720
agggggaaac taaaacgcag agcaattgca accccaggaa tgcaaataag ggggtttgta      780
tactttgttg agacactggc aagaagcata tgtgaaaagc ttgaacaatc agggttgcca      840
gttggaggaa atgagaagaa agcaaagtta gcaaatgttg taaggaagat gatgaccaac      900
tcccaggaca ctgaaatttc ttttaccatc actggagata cacaaaatg gaacgaaaat       960 caaaacccta gaatgttctt ggccatgatc acatatataa ccaaagatca gcctgaatgg     1020
ttcagaaata ttctaagtat tgctccaata atgttttcaa acaaaatggc gagactaggt     1080
agggggtata tgtttgaaag caagagtatg aaactgagaa cccaaatacc tgcagagatg     1140
ctagccaaca tagatttgaa atatttcaat gattcaacta aaagaaaat tgaaaaatt       1200 cgaccattat taatagatgg aactgcatca ttgagtcctg aatgatgat gggcatgttc       1260 aatatgttaa gcaccgtctt gggcgtttcc attctgaatc ttgggcaaaa aagatacacc     1320
aagactactt actggtggga tggtcttcaa tcgtctgatg attttgcttt gattgtgaat     1380
gcacccaatt atgcaggaat tcaagctgga gttgacaggt tttatcgaac ctgtaagctg     1440
ctcggaatta atatgagcaa aaagaagtct tacataaaca gaacaggtac ctttgaattc     1500
acgagctttt tctatcgtta tgggtttgtt gccaatttca gcatggagct tcctagtttt     1560
ggggtgtctg gggtcaatga atctgcagac atgagtattg gagtcactgt catcaaaaac     1620
aatatgataa acaatgacct tggcccagca actgctcaaa tggcccttca gttatttata     1680
aaagattaca ggtacactta tcgatgccac agaggtgaca cacaaataca aacccggaga     1740
tcatttgaaa taagaaact atgggaccaa acccgctcca agctgggct gttggtctct       1800 gatggaggcc ccaatttata taacattagg aatctacata ttcctgaagt ctgcttgaaa     1860
tgggagttga tggatgagga ttaccagggg cgtttatgca cccattgaa cccgtttgtc       1920 agccataaag agattgaatc agtgaacaat gcagtgataa tgccggcaca tggtccagcc     1980
aaaaatatgg agtatgacgc tgttgcaaca acacactctt gggtccccaa agaaatcga      2040 tccatttaa acacgagcca aagagggata cttgaagatg agcaaatgta ccaaggtgc       2100 tgcaatttat ttgaaaaatt cttcccaagt agctcataca aagaccagt tggaatatcc       2160 agtatggtag aggctatggt ttcaagagcc cgaattgatg cacggattga tttcgaatct     2220
ggaaggataa agaagagga attcgctgag atcatgaaga cctgttccac cattgaagac     2280
ctcagacggc aaaaataggg aatttggctt gtccttcatg aaaaaatgcc ttgtttctac     2340
t                                                                     2341
```

<210> SEQ ID NO 19
<211> LENGTH: 2341
<212> TYPE: DNA
<213> ORGANISM: Influenza A virus

<400> SEQUENCE: 19

```
agcgaaagca ggtcaattat attcaatatg gaaagaataa aagagctaag gaatctgatg      60
tcacaatctc gcactcgcga gatacttacc aaaactactg tagaccacat ggccataata    120
aagaaataca catcaggaag acaggagaaa aacccatcac ttaggatgaa atggatgatg    180
gcaatgaaat acccaattac agctgataaa aggataacgg aaatgattcc tgaaagaaat    240
gagcaaggac agacactatg gagtaaagtg aatgatgccg gatcagaccg agtgatgata    300
tcaccccctag ctgtgacatg gtggaacaga atggaccag tggcaaacac tatccactat    360
ccaaaaatct acaaaactta ctttgaaaag gttgaaaggt taaaacatgg aacctttggc    420
cctgtacact ttagaaacca agtcaaaata cgccgaagag tcgacataaa tcctggtcat    480
gcagacctca gcgccaagga ggcacaggat gtaattatgg aagttgtttt ccctaatgaa    540
gtgggagcca gaatactaac atcagaatcg caattaacga taactaagga gaaaaaagag    600
gaactccaga attgcaaaat ttccccttttg atggttgcat acatgttaga gagggaactt    660
gtccgcaaaa caagatttct cccggttgca ggtggaacaa gcagtgtgta cattgaagtt    720
ttgcatttaa cacagggggac atgctgggag cagatgtaca ctccaggtgg ggaggtgagg    780
aatgatgatg ttgatcaaag cctaattatt gctgctagga acatagtgag aagagctgca    840
gtatcagcag atccactagc atctttatta gaaatgtgcc atagcacaca gattggtgga    900
acaaggatgg tggatattct caggcaaaat ccaacagaag aacaagctgt ggacatatgc    960
aaagcagcaa tggggctgag aatcagttca tccttcagtt ttggcggatt cacatttaag   1020
agaacaagtg gatcgtcagt caaaagggag gaagaagtgc taacgggcaa tctgcaaaca   1080
ttgaagctaa ctgtgcatga gggatatgaa gaattcacaa tagttgggaa aaaggcaaca   1140
gctatactca gaaaagcaac caggagattg attcaactaa tagtgagtgg aagagacgaa   1200
cagtcaatag tcgaagcaat agttgtagca atggtattct cacaagaaga ttgcatggta   1260
aaagcggtta gaggtgatct gaatttcgtt aatagagcga atcagcggtt gaatcccatg   1320
catcaacttt tgagacattt tcagaaggat gctaaagtac ttttcctaaa ttggggaatt   1380
gaacatattg acaatgtgat gggaatgatt gggatattac ctgatatgac tccaagtacc   1440
gagatgtcaa tgagaggagt gagagtcagc aaaatgggtg tagatgaata ctccaatgct   1500
gaaagggtag tggtaagcat tgaccgtttt ttgagggtcc gggaccaaag aggaaatgta   1560
ttactgtctc cagaggaagt cagtgaaaca caaggaacag agaaactgac aataacttac   1620
tcttcatcat tgatgtggga gattaatggc cctgagtcag tgttgatcaa tacctaccaa   1680
tggatcatca gaaactggga gactgttaaa attcagtggt ctcagaaccc tacaatgcta   1740
tacaataaaa tggaatttga gccatttcaa tctctagtcc ccaaggccat tagaggccaa   1800
tacagtgggt ttgttagaac tctatttcaa caaatgaggg atgtgctcgg gacctttgac   1860
acaactcaga taataaaact tcttcccttt gcagccgctc caccaaagca agtagaatg   1920
caattctcgt cattaactgt gaatgtgagg ggatcaggaa tgagaatact tgtaaggggt   1980
aattctccag tattcaacta caacaagacc actaagagac tcacaatcct cggaaaggat   2040
gctggcactt taactgaaga cccagatgaa ggcacagctg gagtggaatc tgctgtttta   2100
agggattcc tcattctagg caagaagat agaagatatg gccagcatt aagcatcagt   2160
gaattgagca accttgcgaa aggggagaaa gctaatgtgc taattgggca aggggatgta   2220
gtgttggtaa tgaaacgaaa acgggactct agcatactta ctgacagcca gacagcgacc   2280
aaaagaattc ggatggccat caattaattt cgaataattt aaaaacgacc ttgtttctac   2340
t                                                                  2341
```

<210> SEQ ID NO 20
<211> LENGTH: 1565
<212> TYPE: DNA
<213> ORGANISM: Influenza A virus

<400> SEQUENCE: 20
agcaaaagca gggtagataa tcactcactg agtgacatca aagtcatggc gtcccaaggc 60
accaaacggt cttacgaaca gatggagact gatggggaac gccagaatgc aactgaaatc 120
agagcatccg tcggaagaat gattggggga attgggcgat tctacatcca aatgtgcacc 180
gagcttaagc tcaatgatta tgagggacga ctgatccaga acagcttaac aatagagaga 240
atggtgcttt ctgcttttga tgagaggaga aataaatatc tggaagaaca tcccagcgca 300
gggaaagatc ctaagaaaac tggaggaccc atatacaaga gagtagatgg aaagtgggtg 360
agggaactcg tcctttatga caaagaagaa ataaggcgga tttggcgcca agccaacaat 420
ggtgatgatg caacagctgg tttgactcac attatgatct ggcattctaa tttgaatgat 480
acaacttacc agaggacaag agctcttgtc cgcaccggaa tggatcccag gatgtgctct 540
ttgatgcaag gttcaactct ccctagaaga tctggagcag caggcgctgc agtcaaagga 600
gttgggacaa tggtattgga gttaatcagg atgatcaaac gtgggatcaa cgaccgaaac 660
ttctggaggg gtgagaatgg gagaaaaaca aggattgctt atgagagaat gtgcaacatt 720
ctcaaaggaa aatttcaaac agctgcacaa aaagcaatga tggatcaagt gagagaaagc 780
cggaacccag gaaatgctga gatcgaagat ctcacttttc tggcacggtc tgcactcata 840
ttgagaggat cagttgctca caagtcttgc ctgcctgctt gtgtgtatgg accagccgta 900
gccagtgggt atgacttcga aaaagaggga tactctttgg tgggagtaga ccctttcaaa 960
ctgcttcaaa ccagtcaggt atacagccta attagaccaa acgagaatcc cgcacacaag 1020
agccagttgg tgtggatggc atgcaattct gctgcatttg aagatctaag agtgtcaagc 1080
ttcatcagag ggacaagagt acttccaagg gggaagctct ccactagagg agtacaaatt 1140
gcttcaaatg aaaacatgga tgctattgtc tcaagtactc ttgaactgag aagcagatac 1200
tgggccataa gaaccagaag tggagggaac accaatcaac aaagggcctc tgcgggccaa 1260
atcagcacac aacctacgtt ttctgtgcag agaaacctcc catttgacaa aacaaccatc 1320
atggcagcat tcactgggaa tacagaggga agaacatcag acatgcgggc agaaatcata 1380
aagatgatgg aaagtgcaag accagaagaa gtgtccttcc agggacgggg agtctttgag 1440
ctctcggacg aaagggcaac gaacccgatc gtgccctcct ttgacatgag taatgaagga 1500
tcttatttct tcggagacaa tgcagaggag tacgacaatt aatgaaaaat acccttgttt 1560
ctact 1565

<210> SEQ ID NO 21
<211> LENGTH: 1027
<212> TYPE: DNA
<213> ORGANISM: Influenza A virus

<400> SEQUENCE: 21
agcaaaagca ggtagatatt gaaagatgag tcttctaacc gaggtcgaaa cgtacgttct 60
ctctatcgtc ccatcaggcc ccctcaaagc cgagatcgca cagagacttg aagatgtatt 120
tgctggaaag aataccgatc ttgaggctct catggaatgg ctaaagacaa gaccaatcct 180
gtcacctctg actaagggga ttttaggatt tgtgttcacg ctcaccgtgc ccagtgagcg 240

| | |
|---|---|
| aggactgcag cgtagacgct ttgtccaaaa tgcccttaat gggaatgggg atccaaataa | 300 |
| tatggacaag gctgtcaaac tgtatcgaaa gcttaagagg gagataacat tccatggggc | 360 |
| caaagaaata gcactcagtt attctgctgg agcacttgcc agttgtatgg gactcatata | 420 |
| caacaggatg ggggctgtga ccaccgaatc agcatttggc cttatatgtg caacctgtga | 480 |
| acagattgcc gactcccagc ataagtctca taggcaaatg gtaacaacaa ccaatccatt | 540 |
| aataagacat gagaacagaa tggttctggc cagcactaca gctaaggcta tggagcaaat | 600 |
| ggctggatcg agtgaacaag cagctgaggc catggaggtt gctagtcagg ccaggcagat | 660 |
| ggtgcaggca atgagagcca ttgggactca tcctagctct agcactggtc tgaaaaatga | 720 |
| tctccttgaa aatttgcagg cctatcagaa acgaatgggg gtgcagatgc aacgattcaa | 780 |
| gtgatcctct tgttgttgcc gcaagtataa ttgggattgt gcacctgata ttgtggatta | 840 |
| ttgatcgcct ttttccaaa agcatttatc gtattttaa acacggttta aaagagggc | 900 |
| cttctacgga aggagtaccg gagtctatga gggaagaata tcgagaggaa cagcagaatg | 960 |
| ctgtggatgc tgacgatggt cattttgtca gcatagagct agagtaaaaa actaccttgt | 1020 |
| ttctact | 1027 |

<210> SEQ ID NO 22
<211> LENGTH: 889
<212> TYPE: DNA
<213> ORGANISM: Influenza A virus

<400> SEQUENCE: 22

| | |
|---|---|
| agcaaaagca gggtggcaaa gacataatgg attcccacac tgtgtcaagc tttcaggtag | 60 |
| attgtttcct ttggcatgtc cgcaaacaag ttgcagacca agatctaggc gatgccccct | 120 |
| tccttgatcg gcttcgccga gatcagaagt ctctaaaggg acgaggcaac actctcggtc | 180 |
| tgaacatcga aacagccact gtgttggaa agcaaatagt agagaggatt ctgaaagaag | 240 |
| aatccgatga gacatttaga atgaccatgg cctccgcact tgcttcgcgg tacctaactg | 300 |
| acatgactgt tgaagaaatg tcaagggact ggttcatgct catgcccaag cagaaagtgg | 360 |
| ctggcccctct ttgtgtcaga atggaccagg cgataatgga taagaacatc atactgaaag | 420 |
| cgaacttcag tgtgattttt gaccggttgg agaatctgac attactaagg gctttcaccg | 480 |
| aagagggagc aattgttggc gaaatttcac cattgccttc ttttccagga catactaatg | 540 |
| aggatgtcaa aaatgcaatt ggggtcctca tcggggact tgaatggaat gataacacag | 600 |
| ttcgagtctc tgaagctcta cagagattcg cttggagaag cagtaatgag actgggggac | 660 |
| ctccattcac tacaacacag aaacggaaaa tggcgggaac aattaggtca gaagtttgaa | 720 |
| gaataagat ggctgattga agaagtgagg cataaattga agacgacaga gagtagtttt | 780 |
| gaacaaataa catttatgca agcattacag ctattgtttg aagtggaaca agagattaga | 840 |
| acgttctcgt ttcagcttat ttaatgataa aacacccctt gtttctact | 889 |

<210> SEQ ID NO 23
<211> LENGTH: 1775
<212> TYPE: DNA
<213> ORGANISM: Influenza A virus

<400> SEQUENCE: 23
agcgaaagca ggggaaaata aaagcaacca aaatgaaagt aaaactactg gttctgttat 60
gtacatttac agctacatat gcagacacaa tatgtatagg ctaccatgcc aacaactcaa 120
ccgacactgt tgacacagta cttgagaaga atgtaacagt gacacactct gtcaacctac 180

-continued

| | |
|---|---|
| ttgaggacag tcacaatgga aaactatgtc tactaaaagg aatagcccca ctacaattgg | 240 |
| gtaattgcag cgttgccgga tggatcttag gaaacccaga atgcgaatta ctgatttcca | 300 |
| aggaatcatg gtcctacatt gtagaaacac caaatcctga aatggaaca tgttacccag | 360 |
| ggtatttcgc cgactatgag gaactgaggg agcaattgag ttcagtatct tcatttgaaa | 420 |
| ggttcgaaat attccccaaa gagagctcat ggcccaacca caccgtaacc ggagtatcag | 480 |
| catcatgctc ccataacggg aaaagcagtt tttacagaaa tttgctatgg ctgacgggga | 540 |
| agaatggttt gtacccaaac ctgagcaagt cctatgcaaa caacaaagag aaagaagtcc | 600 |
| ttgtactatg gggtgttcat cacccgccta acataggggga ccaagggcc ctctatcata | 660 |
| cagaaaatgc ttatgtctct gtagtgtctt cacattatag cagaagattc accccagaaa | 720 |
| tagccaaaag acccaaggtg agagaccagg aaggaagaat caactactac tggactctgc | 780 |
| tggaacccgg ggatacaata atatttgagg caaatggaaa tctaatagcg ccaaggtatg | 840 |
| ctttcgcact gagtagaggc ttgggatcag gaatcatcac ctcaaatgca ccaatggatg | 900 |
| aatgtgatgc aaagtgtcaa acacctcagg gagctataaa cagcagtctt cctttccaga | 960 |
| atgtacaccc agtcacaata ggagagtgtc caaagtatgt caggagtgca aaattaagga | 1020 |
| tggttacagg actaaggaac atcccatcca ttcaatccag aggtttgttt ggagcaattg | 1080 |
| ccggtttcat tgaaggggggg tggactgaa tggtagatgg ttggtatggt tatcatcatc | 1140 |
| agaatgagca aggatctggg tatgctgcag atcaaaaaag cacacaaaat gccattaacg | 1200 |
| ggattacaaa caaggtgaat tctgtaattg agaaaatgaa cactcaattc acagctgtgg | 1260 |
| gcaaagaatt caacaaattg gaaagaagga tggaaaactt aaataaaaaa gttgatgatg | 1320 |
| ggttctaga catttggacc tataatgcag aattgttggt tctactggaa atgaaagga | 1380 |
| ctttggattt ccatgactcc aacgtgaaga atctgtatga gaaagtaaaa agccaattaa | 1440 |
| agaataatgc caaagaaata ggaaacgggt gttttgaatt ctatcacaag tgtaacgatg | 1500 |
| aatgcatgga gagtgtgaaa aatggaactt atgactatcc aaaatattcc gaagaatcaa | 1560 |
| agttaaacag agaaaaatt gatggagtga aattggaatc aatgggagtc tatcagattc | 1620 |
| tggcgatcta ctcaacagtc gccagttccc tggttctttt ggtctccctg ggggcaatca | 1680 |
| gcttctggat gtgttccaat gggtctttgc agtgtagaat atgcatctaa gaccagaatt | 1740 |
| tcagaaatat aaggaaaaac acccttgttt ctact | 1775 |

<210> SEQ ID NO 24
<211> LENGTH: 1462
<212> TYPE: DNA
<213> ORGANISM: Influenza A virus

<400> SEQUENCE: 24

| | |
|---|---|
| agcaaaagca ggagtttaaa atgaatccaa atcaaaaaat aataaccatt ggatcaatca | 60 |
| gtatagcaat cggaataatt agtctaatgt tgcaaatagg aaatattatt tcaatatggg | 120 |
| ctagtcactc aatccaaact ggaagtcaaa accacactgg aatatgcaac caaaaaatca | 180 |
| tcacatatga aaacagcacc tgggtgaatc acacatatgt taatattaac aacactaatg | 240 |
| ttgttgctgg aaaggacaaa acttcagtga cactggccgg caattcatct ctttgtccta | 300 |
| tcagtggatg ggctatatac acaaaagaca acagcataag aattggctcc aaaggagatg | 360 |
| tttttgtcat aagagaacct ttcatatcat gttctcactt ggaatgcaga accttttttc | 420 |
| tgacccaagg tgctctatta aatgacaaac attcaaatga aaccgttaag gacagaagtc | 480 |

```
cttatagggc cttaatgagc tgtcctctag gtgaagcccc gtcaccatac aattcaaagt      540
ttgaatcagt tgcatggtca gcaagcgcat gccatgatgg caagggctgg ttaacaatcg      600
gaatttctgg tccagacaat ggagctgtgg ctgtactaaa atacaacgga ataataactg      660
aaaccataaa aagttgggaa aagcgaatat tgagaacaca agagtctgaa tgtgtttgtg      720
tgaacgggtc atgtttcacc ataatgaccg atggcccgag taatgggcc gcctcgtaca      780 aaatcttcaa gatcgaaaag gggaaggtta ctaaatcaac agagttgaat gcacccaatt      840
ttcattatga ggaatgttcc tgttacccag acactggcac agtgatgtgt gtatgcaggg      900
acaactggca tggttcaaat cgaccttggg tatcttttaa tcaaaacttg gattatcaaa      960
taggatacat ctgcagtgga gtgttcggtg acaatccgcg tcccaaagat gggaagggca     1020
gctgtaatcc agtgactgtt gatggagcag acggagttaa ggggttttca tacaaatatg     1080
gtaatggtgt ttggatagga aggactaaaa gtaacagact tagaaagggg tttgagatga     1140
tttgggatcc taatgatgg acagataccg acagtgattt ctcagtgaaa caggatgttg     1200
tggcaataac tgattggtca gggtacagcg gaagtttcgt ccaacatcct gagttaacag     1260
gattggactg tataagacct tgcttctggg ttgagttagt cagaggactg cctagagaaa     1320
atacaacaat ctggactagt gggagcagca tttctttttg tggcgttgat agtgatactg     1380
caaattggtc ttggccagac ggtgctgagt tgccgttcac cattgacaag tagctcgttg     1440
aaaaaaactc cttgtttcta ct                                              1462

<210> SEQ ID NO 25
<211> LENGTH: 566
<212> TYPE: PRT
<213> ORGANISM: Influenza A virus

<400> SEQUENCE: 25

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Asn His Asn Gly Lys Leu Cys Lys Leu Lys Gly Ile
        50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
```

```
            195                 200                 205
Tyr Arg Lys Glu Asn Ala Tyr Val Ser Val Ser Ser His Tyr Asn
210                 215                 220
Arg Arg Phe Thr Pro Glu Ile Ala Lys Arg Pro Lys Val Arg Asn Gln
225                 230                 235                 240
Glu Gly Arg Ile Asn Tyr Tyr Trp Thr Leu Leu Glu Pro Gly Asp Thr
            245                 250                 255
Ile Ile Phe Glu Ala Asn Gly Asn Leu Ile Ala Pro Trp Tyr Ala Phe
            260                 265                 270
Ala Leu Ser Arg Gly Phe Gly Ser Gly Ile Ile Thr Ser Asn Ala Ser
            275                 280                 285
Met Asp Glu Cys Asp Ala Lys Cys Gln Thr Pro Gln Gly Ala Ile Asn
            290                 295                 300
Ser Ser Leu Pro Phe Gln Asn Val His Pro Val Thr Ile Gly Glu Cys
305                 310                 315                 320
Pro Lys Tyr Val Arg Ser Thr Lys Leu Arg Met Val Thr Gly Leu Arg
            325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Ile Asp Gly Trp Tyr Gly Tyr
            355                 360                 365
His His Gln Asn Glu Gln Gly Ser Gly Tyr Ala Ala Asp Gln Lys Ser
            370                 375                 380
Thr Gln Asn Ala Ile Asn Gly Ile Thr Asn Lys Val Asn Ser Ile Ile
385                 390                 395                 400
Glu Lys Met Asn Thr Gln Phe Thr Ala Val Gly Lys Glu Phe Asn Lys
            405                 410                 415
Leu Glu Lys Arg Met Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
            435                 440                 445
Glu Arg Thr Leu Asp Phe His Asp Ser Asn Val Lys Asn Leu Tyr Glu
            450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asn Asn Glu Cys Met Glu Ser Val
            485                 490                 495
Lys Asn Gly Thr Tyr Asp Tyr Pro Lys Tyr Ser Glu Glu Ser Lys Leu
            500                 505                 510
Asn Arg Glu Lys Ile Asp Gly Val Lys Leu Glu Ser Met Gly Val Tyr
            515                 520                 525
Gln Ile Leu Ala Ile Tyr Ser Thr Val Ala Ser Ser Leu Val Leu Leu
            530                 535                 540
Val Ser Leu Gly Ala Ile Ser Phe Trp Met Cys Ser Asn Gly Ser Leu
545                 550                 555                 560
Gln Cys Arg Ile Cys Ile
            565

<210> SEQ ID NO 26
<211> LENGTH: 470
<212> TYPE: PRT
<213> ORGANISM: Influenza A virus

<400> SEQUENCE: 26
```

-continued

```
Met Asn Pro Asn Gln Lys Ile Ile Thr Ile Gly Ser Ile Cys Met Thr
 1               5                  10                  15

Ile Gly Ile Ile Ser Leu Ile Leu Gln Ile Gly Asn Ile Ile Ser Ile
             20                  25                  30

Trp Val Ser His Ser Ile Gln Thr Gly Ser Gln Asn His Thr Gly Ile
             35                  40                  45

Cys Asn Gln Arg Ile Ile Thr Tyr Glu Asn Ser Thr Trp Val Asn Gln
 50                  55                  60

Thr Tyr Val Asn Ile Asn Asn Thr Asn Val Val Ala Gly Lys Asp Thr
 65                  70                  75                  80

Thr Ser Val Thr Leu Ala Gly Asn Ser Ser Leu Cys Pro Ile Arg Gly
                 85                  90                  95

Trp Ala Ile Tyr Ser Lys Asp Asn Ser Ile Arg Ile Gly Ser Lys Gly
             100                 105                 110

Asp Val Phe Val Ile Arg Glu Pro Phe Ile Ser Cys Ser His Leu Glu
             115                 120                 125

Cys Arg Thr Phe Phe Leu Thr Gln Gly Ala Leu Leu Asn Asp Lys His
 130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
             165                 170                 175

Val Ala Trp Ser Ala Ser Ala Cys His Asp Gly Met Gly Trp Leu Thr
             180                 185                 190

Ile Gly Ile Ser Gly Pro Asp Asp Gly Ala Val Ala Val Leu Lys Tyr
             195                 200                 205

Asn Gly Ile Ile Thr Glu Thr Ile Lys Ser Trp Arg Lys Arg Ile Leu
 210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Pro Ala Ser Tyr Arg Ile Phe
             245                 250                 255

Lys Ile Glu Lys Gly Lys Ile Thr Lys Ser Ile Glu Leu Asp Ala Pro
             260                 265                 270

Asn Ser His Tyr Glu Glu Cys Ser Cys Tyr Pro Asp Thr Gly Thr Val
 275                 280                 285

Met Cys Val Cys Arg Asp Asn Trp His Gly Ser Asn Arg Pro Trp Val
             290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
             325                 330                 335

Pro Val Thr Val Asp Gly Ala Asp Gly Val Lys Gly Phe Ser Tyr Arg
             340                 345                 350

Tyr Gly Asn Gly Val Trp Ile Gly Arg Thr Lys Ser Asn Ser Ser Arg
             355                 360                 365

Lys Gly Phe Glu Met Ile Trp Asp Pro Asn Gly Trp Thr Asp Thr Asp
 370                 375                 380

Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
             405                 410                 415

Cys Met Arg Pro Cys Phe Trp Val Glu Leu Val Arg Gly Arg Pro Arg
```

```
            420                 425                 430
Glu Gly Thr Thr Val Trp Thr Ser Gly Ser Ser Ile Ser Phe Cys Gly
            435                 440                 445

Val Asn Ser Asp Thr Ala Asn Trp Ser Trp Pro Asp Gly Ala Glu Leu
        450                 455                 460

Pro Phe Thr Ile Asp Lys
465                 470

<210> SEQ ID NO 27
<211> LENGTH: 469
<212> TYPE: PRT
<213> ORGANISM: Influenza A virus

<400> SEQUENCE: 27

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
            85                  90                  95

Trp Ala Ile Tyr Ser Lys Asp Asn Ser Val Arg Ile Gly Ser Lys Gly
        100                 105                 110

Asp Val Phe Val Ile Arg Glu Pro Phe Ile Ser Cys Ser Pro Leu Glu
    115                 120                 125

Cys Arg Thr Phe Phe Leu Thr Gln Gly Ala Leu Leu Asn Asp Lys His
130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
            165                 170                 175

Val Ala Trp Ser Ala Ser Ala Cys His Asp Gly Ile Asn Trp Leu Thr
        180                 185                 190

Ile Gly Ile Ser Gly Pro Asp Asn Gly Ala Val Ala Val Leu Lys Tyr
    195                 200                 205

Asn Gly Ile Ile Thr Asp Thr Ile Lys Ser Trp Arg Asn Asn Ile Leu
210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
            245                 250                 255

Arg Ile Glu Lys Gly Lys Ile Val Lys Ser Val Glu Met Asn Ala Pro
        260                 265                 270

Asn Tyr His Tyr Glu Glu Cys Ser Cys Tyr Pro Asp Ser Ser Glu Ile
    275                 280                 285

Thr Cys Val Cys Arg Asp Asn Trp His Gly Ser Asn Arg Pro Trp Val
290                 295                 300

Ser Phe Asn Gln Asn Leu Glu Tyr Gln Ile Gly Tyr Ile Cys Ser Gly
305                 310                 315                 320
```

```
Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 28
<211> LENGTH: 2277
<212> TYPE: DNA
<213> ORGANISM: Influenza A virus

<400> SEQUENCE: 28
atggaacgca ttaaagaact gcgcaacctg atgagccaga gccgcacccg cgaaattctg      60
accaaaacca ccgtggatca tatggcgatt attaaaaaat ataccagcgg ccgccaggaa     120
aaaaacccga gcctgcgcat gaaatggatg atggcgatga aatatccgat taccgcggat     180
aaacgcatta ccgaaatgat tccggaacgc aacgaacagg ccagaccct gtggagcaaa      240 gtgaacgatg cgggcagcga tcgcgtgatg attagcccgc tggcggtgac ctggtggaac     300
cgcaacggcc cggtggcgag caccattcat tatccgaaaa tttataaaac ctattttgaa     360
aaagtggaac gcctgaaaca tggcaccttt ggcccggtgc attttcgcaa ccaggtgaaa     420
attgccgccg cgtggatat taacccgggc catgcggatc tgagcgcgaa agaagcgcag     480
gatgtgatta tggaagtggt gtttccgaac gaagtgggcg cgcgcattct gaccagcgaa     540
agccagctga ccattaccaa agaaaaaaaa gaagaactgc agaactgcaa aattagcccg     600
ctgatggtgg cgtatatgct ggaacgcgaa ctggtgcgca aacccgcttt tctgccggtg     660
gcgggcggca ccagcagcgt gtatattgaa gtgctgcatc tgacccaggg cacctgctgg     720
gaacagatgt ataccccggg cggcgaagtg cgcaacgatg atgtggatca gagcctgatt     780
attgcggcgc gcaacattgt gcgccgcgcg cggtgagcg cggatccgct ggcgagcctg     840
ctggaaatgt gccatagcac ccagattggc ggcacccgca tggtggatat tctgcgccag     900
aacccgaccg aagaacaggc ggtggatatt tgcaaagcgg cgatgggcct gcgcattagc     960
agcagcttta gctttggcgg ctttaccttt aaacgcacca gcggcagcag cgtgaaacgc    1020
gaagaagaag tgctgaccgg caacctgcag accctgaaac tgaccgtgca tgaaggctat    1080
gaagaattta ccatggtggg caaacgcgcg accgcgattc tgcgcaaagc gacccgccgc    1140
ctgattcagc tgattgtgag cggccgcgat aacagagca ttgtggaagc gattgtggtg    1200
gcgatggtgt ttagccagga agattgcatg gtgaaagcgg tgcgcggcga tctgaacttt    1260
```

```
gtgaaccgcg cgaaccagcg cctgaacccg atgcatcagc tgctgcgcca ttttcagaaa   1320
gatgcgaaag tgctgtttct gaactggggc attgaaccga ttgataacgt gatgggcatg   1380
attggcattc tgccggatat gaccccgagc accgaaatga gcatgcgcgg cgtgcgcgtg   1440
agcaaaatgg gcgtggatga atatagcaac gcggaacgcg tggtggtgag cattgatcgc   1500
tttctgcgcg tgcgcgatca gcgcggcaac gtgctgctga gcccggaaga agtgagcgaa   1560
acccagggca ccgaaaaact gaccattacc tatagcagca gcatgatgtg gaaattaac    1620 ggcccggaaa gcgtgctgat taacacctat cagtggatta ttcgcaactg gaaaccgtg    1680 aaaattcagt ggagccagaa cccgaccatg ctgtataaca aatgg aatt tgaaccgttt   1740 cagagcctgg tgccgaaagc gattcgcggc cagtatagcg ctttgtgcg cacctgttt     1800 cagcagatgc gcgatgtgct gggcaccttt gataccaccc agattattaa actgctgccg   1860
tttgcggcgg cgccgccgaa acagagccgc atgcagttta gcagcctgac cgtgaacgtg   1920
cgcggcagcg gcatgcgcat tctggtgcgc ggcaacagcc cggtgtttaa ctataacaaa   1980
accaccaaac gcctgaccgt gctgggcaaa gatgcgggca ccctgaccga agatccggat   2040
gaaggcaccg cgggcgtgga aagcgcggtg ctgcgcggct ttctgattct gggcaaagaa   2100
gatcgccgct atggcccggc gctgagcatt aacgaactga gcaacctggc gaaaggcgaa   2160
aaagcgaacg tgctgattgg ccagggcgat gtggtgctgg tgatgaaacg caaacgcgat   2220
agcagcattc tgaccgatag ccagaccgcg accaaacgca ttcgcatggc gattaac       2277
```

<210> SEQ ID NO 29
<211> LENGTH: 716
<212> TYPE: PRT
<213> ORGANISM: Influenza A virus

<400> SEQUENCE: 29

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190
```

```
Gln Ser Glu Arg Gly Glu Glu Thr Ile Glu Glu Lys Phe Glu Ile Thr
                195                 200                 205
Gly Thr Met Arg Lys Leu Ala Asp Gln Ser Leu Pro Pro Asn Phe Pro
    210                 215                 220
Ser Leu Glu Asn Phe Arg Ala Tyr Val Asp Gly Phe Glu Pro Asn Gly
225                 230                 235                 240
Cys Ile Glu Gly Lys Leu Ser Gln Met Ser Lys Glu Val Asn Ala Lys
                245                 250                 255
Ile Glu Pro Phe Leu Arg Thr Thr Pro Arg Pro Leu Arg Leu Pro Asp
            260                 265                 270
Gly Pro Leu Cys His Gln Arg Ser Lys Phe Leu Leu Met Asp Ala Leu
        275                 280                 285
Lys Leu Ser Ile Glu Asp Pro Ser His Glu Gly Glu Gly Ile Pro Leu
    290                 295                 300
Tyr Asp Ala Ile Lys Cys Met Lys Thr Phe Phe Gly Trp Lys Glu Pro
305                 310                 315                 320
Asn Ile Val Lys Pro His Glu Lys Gly Ile Asn Pro Asn Tyr Leu Met
                325                 330                 335
Ala Trp Lys Gln Val Leu Ala Glu Leu Gln Asp Ile Glu Asn Glu Glu
            340                 345                 350
Lys Ile Pro Arg Thr Lys Asn Met Lys Arg Thr Ser Gln Leu Lys Trp
        355                 360                 365
Ala Leu Gly Glu Asn Met Ala Pro Glu Lys Val Asp Phe Asp Asp Cys
    370                 375                 380
Lys Asp Val Gly Asp Leu Lys Gln Tyr Asp Ser Asp Glu Pro Glu Pro
385                 390                 395                 400
Arg Ser Leu Ala Ser Trp Val Gln Asn Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu His Ile Ala Ser Met Arg Arg Asn Tyr Phe Thr Ala
        435                 440                 445
Glu Val Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Leu Glu Pro His Lys Trp Glu Lys Tyr Cys Val Leu Glu
    530                 535                 540
Ile Gly Asp Met Leu Leu Arg Thr Ala Ile Gly Gln Val Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590
Glu Ser Met Ile Glu Ala Glu Ser Ser Val Lys Glu Lys Asp Met Thr
        595                 600                 605
Lys Glu Phe Phe Glu Asn Lys Ser Glu Thr Trp Pro Ile Gly Glu Ser
```

```
                610              615              620
Pro Arg Gly Val Glu Glu Gly Ser Ile Gly Lys Val Cys Arg Thr Leu
625              630              635              640

Leu Ala Lys Ser Val Phe Asn Ser Leu Tyr Ala Ser Pro Gln Leu Glu
                645              650              655

Gly Phe Ser Ala Glu Ser Arg Lys Leu Leu Ile Val Gln Ala Leu
                660              665              670

Arg Asp Asn Leu Glu Pro Gly Thr Phe Asp Leu Gly Gly Leu Tyr Glu
            675              680              685

Ala Ile Glu Glu Cys Leu Ile Asn Asp Pro Trp Val Leu Leu Asn Ala
            690              695              700

Ser Trp Phe Asn Ser Phe Leu Thr His Ala Leu Lys
705              710              715
```

<210> SEQ ID NO 30
<211> LENGTH: 757
<212> TYPE: PRT
<213> ORGANISM: Influenza A virus

<400> SEQUENCE: 30

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Arg Gly Arg Trp Thr Lys Asn Thr Glu Thr Gly Ala Pro
50                  55                  60

Gln Leu Asn Pro Ile Asp Gly Pro Leu Pro Lys Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Ile Ala Asn Glu Ser
145                 150                 155                 160

Gly Arg Leu Ile Asp Phe Leu Lys Asp Val Met Glu Ser Met Asp Arg
                165                 170                 175

Asp Glu Val Glu Val Thr Thr His Phe Gln Arg Lys Arg Arg Val Arg
            180                 185                 190

Asp Asn Val Thr Lys Lys Met Val Thr Gln Arg Thr Ile Gly Lys Lys
        195                 200                 205

Lys His Lys Leu Asp Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270
```

```
Val Gly Gly Asn Glu Lys Lys Ala Lys Leu Ala Asn Val Arg Lys
            275                 280                 285
Met Met Thr Asn Ser Gln Asp Thr Glu Ile Ser Phe Thr Ile Thr Gly
            290                 295                 300
Asp Asn Thr Lys Trp Asn Glu Asn Gln Asn Pro Arg Met Phe Leu Ala
305                 310                 315                 320
Met Ile Thr Tyr Ile Thr Lys Asn Gln Pro Glu Trp Phe Arg Asn Ile
                325                 330                 335
Leu Ser Ile Ala Pro Ile Met Phe Ser Asn Lys Met Ala Arg Leu Gly
            340                 345                 350
Lys Gly Tyr Met Phe Glu Ser Lys Ser Met Lys Leu Arg Thr Gln Ile
            355                 360                 365
Pro Ala Glu Met Leu Ala Asn Ile Asp Leu Lys Tyr Phe Asn Asp Ser
            370                 375                 380
Thr Lys Arg Lys Ile Glu Lys Ile Arg Pro Leu Leu Ile Asp Gly Thr
385                 390                 395                 400
Ala Ser Leu Ser Pro Gly Met Met Met Gly Met Phe Asn Met Leu Ser
                405                 410                 415
Thr Val Leu Gly Val Ser Ile Leu Asn Leu Gly Gln Lys Arg Tyr Thr
            420                 425                 430
Lys Thr Thr Tyr Trp Trp Asp Gly Leu Gln Ser Ser Asp Asp Phe Ala
            435                 440                 445
Leu Ile Val Asn Ala Pro Asn Tyr Ala Gly Ile Gln Ala Gly Val Asp
            450                 455                 460
Arg Phe Tyr Arg Thr Cys Lys Leu Leu Gly Ile Asn Met Ser Lys Lys
465                 470                 475                 480
Lys Ser Tyr Ile Asn Arg Thr Gly Thr Phe Glu Phe Thr Ser Phe Phe
                485                 490                 495
Tyr Arg Tyr Gly Phe Val Ala Asn Phe Ser Met Glu Leu Pro Ser Phe
                500                 505                 510
Gly Val Ser Gly Val Asn Glu Ser Ala Asp Met Ser Ile Gly Val Thr
            515                 520                 525
Val Ile Lys Asn Asn Met Ile Asn Asn Asp Leu Gly Pro Ala Thr Ala
            530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Ile
                565                 570                 575
Lys Lys Leu Trp Asp Gln Thr Arg Ser Lys Ala Gly Leu Leu Val Ser
            580                 585                 590
Asp Gly Gly Pro Asn Leu Tyr Asn Ile Arg Asn Leu His Ile Pro Glu
            595                 600                 605
Val Cys Leu Lys Trp Glu Leu Met Asp Glu Asp Tyr Gln Gly Arg Leu
610                 615                 620
Cys Asn Pro Ser Asn Pro Phe Val Ser His Lys Glu Ile Glu Ser Val
625                 630                 635                 640
Asn Asn Ala Val Met Met Pro Ala His Gly Pro Ala Lys Asn Met Glu
                645                 650                 655
Tyr Asp Ala Val Ala Thr Thr His Ser Trp Val Pro Lys Arg Asn Arg
                660                 665                 670
Ser Ile Leu Asn Thr Ser Gln Arg Gly Ile Leu Glu Asp Glu Gln Met
            675                 680                 685
Tyr Gln Arg Cys Cys Asn Leu Phe Glu Lys Phe Phe Pro Ser Ser Ser
```

```
                690                 695                 700
Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Thr Cys Ser Thr Ile Glu Asp
                740                 745                 750

Leu Arg Arg Gln Lys
            755

<210> SEQ ID NO 31
<211> LENGTH: 759
<212> TYPE: PRT
<213> ORGANISM: Influenza A virus

<400> SEQUENCE: 31

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ser Leu Arg Met Lys
            35                  40                  45

Trp Met Met Ala Met Lys Tyr Pro Ile Thr Ala Asp Lys Arg Ile Thr
50                  55                  60

Glu Met Ile Pro Glu Arg Asn Glu Gln Gly Gln Thr Leu Trp Ser Lys
65                  70                  75                  80

Val Asn Asp Ala Gly Ser Asp Arg Val Met Ile Ser Pro Leu Ala Val
                85                  90                  95

Thr Trp Trp Asn Arg Asn Gly Pro Val Ala Ser Thr Ile His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asn Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300
```

```
Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Val Leu Thr Gly Asn Leu Gln Thr Leu
            340                 345                 350

Lys Leu Thr Val His Glu Gly Tyr Glu Glu Phe Thr Met Val Gly Lys
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Val Glu Ala Ile Val Val
385                 390                 395                 400

Ala Met Val Phe Ser Gln Glu Asp Cys Met Val Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Leu Asn
        435                 440                 445

Trp Gly Ile Glu Pro Ile Asp Asn Val Met Gly Met Ile Gly Ile Leu
450                 455                 460

Pro Asp Met Thr Pro Ser Thr Glu Met Ser Met Arg Gly Val Arg Val
465                 470                 475                 480

Ser Lys Met Gly Val Asp Glu Tyr Ser Asn Ala Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Ile Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
```

```
                    725                 730                 735
Arg Lys Arg Asp Ser Ser Ile Leu Thr Asp Ser Gln Thr Ala Thr Lys
            740                 745                 750
Arg Ile Arg Met Ala Ile Asn
        755

<210> SEQ ID NO 32
<211> LENGTH: 498
<212> TYPE: PRT
<213> ORGANISM: Influenza A virus

<400> SEQUENCE: 32

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Asn Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Val Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Ile Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Leu Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Ile Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Val Asp Pro Phe
    290                 295                 300

Lys Leu Leu Gln Thr Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335
```

```
Ala Phe Glu Asp Leu Arg Val Ser Ser Phe Ile Arg Gly Thr Arg Val
                340                 345                 350

Leu Pro Arg Gly Lys Leu Ser Thr Arg Gly Val Gln Ile Ala Ser Asn
            355                 360                 365

Glu Asn Met Asp Ala Ile Val Ser Ser Thr Leu Glu Leu Arg Ser Arg
        370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Thr Gln Pro Thr Phe Ser Val Gln Arg
                405                 410                 415

Asn Leu Pro Phe Asp Lys Thr Thr Ile Met Ala Ala Phe Thr Gly Asn
            420                 425                 430

Thr Glu Gly Arg Thr Ser Asp Met Arg Ala Glu Ile Ile Lys Met Met
        435                 440                 445

Glu Ser Ala Arg Pro Glu Glu Val Ser Phe Gln Gly Arg Gly Val Phe
            450                 455                 460

Glu Leu Ser Asp Glu Arg Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 33
<211> LENGTH: 252
<212> TYPE: PRT
<213> ORGANISM: Influenza A virus

<400> SEQUENCE: 33

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asn Val Phe
                20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
                100                 105                 110

Lys Glu Ile Ala Leu Ser Tyr Ser Ala Gly Ala Leu Ala Ser Cys Met
            115                 120                 125

Gly Leu Ile Tyr Asn Arg Met Gly Ala Val Thr Thr Glu Ser Ala Phe
        130                 135                 140

Gly Leu Ile Cys Ala Thr Cys Glu Gln Ile Ala Asp Ser Gln His Lys
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205
```

Ala Arg Gln Met Val Gln Ala Met Arg Ala Ile Gly Thr His Pro Ser
    210                 215                 220

Ser Ser Thr Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 34
<211> LENGTH: 470
<212> TYPE: PRT
<213> ORGANISM: Influenza A virus

<400> SEQUENCE: 34

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn His Thr Gly Val
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Glu Gly Ser Cys Asn
                325                 330                 335

```
Pro Val Thr Val Asp Gly Ala Asp Gly Val Lys Gly Phe Ser Tyr Lys
            340                 345                 350

Tyr Gly Asn Gly Val Trp Ile Gly Arg Thr Lys Ser Asn Arg Leu Arg
            355                 360                 365

Lys Gly Phe Glu Met Ile Trp Asp Pro Asn Gly Trp Thr Asp Thr Asp
370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
            435                 440                 445

Val Asn Ser Asp Thr Ala Asn Trp Ser Trp Pro Asp Gly Ala Glu Leu
        450                 455                 460

Pro Phe Thr Ile Asp Lys
465                 470

<210> SEQ ID NO 35
<211> LENGTH: 716
<212> TYPE: PRT
<213> ORGANISM: Influenza A virus

<400> SEQUENCE: 35

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Val Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Gly Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Asn Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Arg Leu Ala Asp Gln Ser Leu Pro Pro Asn Phe Ser
    210                 215                 220

Cys Leu Glu Asn Phe Arg Ala Tyr Val Asp Gly Phe Glu Pro Asn Gly
```

-continued

```
             225                 230                 235                 240

Cys Ile Glu Gly Lys Leu Ser Gln Met Ser Lys Glu Val Asn Ala Gln
                245                 250                 255

Ile Glu Pro Phe Leu Lys Thr Thr Pro Arg Pro Ile Lys Leu Pro Asn
                260                 265                 270

Gly Pro Pro Cys Tyr Gln Arg Ser Lys Phe Leu Leu Met Asp Ala Leu
                275                 280                 285

Lys Leu Ser Ile Glu Asp Pro Ser His Glu Gly Glu Gly Ile Pro Leu
            290                 295                 300

Tyr Asp Ala Ile Lys Cys Met Lys Thr Phe Phe Gly Trp Lys Glu Pro
305                 310                 315                 320

Tyr Ile Val Lys Pro His Glu Lys Gly Ile Asn Ser Asn Tyr Leu Leu
                325                 330                 335

Ser Trp Lys Gln Val Leu Ser Glu Leu Gln Asp Ile Glu Asn Glu Glu
                340                 345                 350

Lys Ile Pro Arg Thr Lys Asn Met Lys Lys Thr Ser Gln Leu Lys Trp
                355                 360                 365

Ala Leu Gly Glu Asn Met Ala Pro Glu Lys Val Asp Phe Glu Asn Cys
            370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Val Trp Ile Glu Leu Asp Glu Ile Gly Glu Asp Val
                420                 425                 430

Ala Pro Ile Glu His Ile Ala Ser Met Arg Arg Asn Tyr Phe Thr Ala
                435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
                500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
            530                 535                 540

Ile Gly Asp Met Leu Leu Arg Ser Ala Ile Gly Gln Ile Ser Arg Pro
545                 550                 555                 560

Met Phe Leu Tyr Val Arg Thr Asn Gly Thr Ser Lys Val Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Ala Trp Pro Ile Gly Glu Ser
            610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655
```

```
Gly Phe Ser Ala Glu Ser Arg Lys Leu Leu Val Val Gln Ala Leu
            660             665             670

Arg Asp Asn Leu Glu Pro Gly Thr Phe Asp Leu Gly Gly Leu Tyr Glu
    675             680             685

Ala Ile Glu Glu Cys Leu Ile Asn Asp Pro Trp Val Leu Leu Asn Ala
    690             695             700

Ser Trp Phe Asn Ser Phe Leu Thr His Ala Leu Lys
705             710             715

<210> SEQ ID NO 36
<211> LENGTH: 757
<212> TYPE: PRT
<213> ORGANISM: Influenza A virus

<400> SEQUENCE: 36

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Ala Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
```

```
          305                 310                 315                 320
Met Ile Thr Tyr Ile Thr Lys Asn Gln Pro Glu Trp Phe Arg Asn Ile
                325                 330                 335
Leu Ser Ile Ala Pro Ile Met Phe Ser Asn Lys Met Ala Arg Leu Gly
                340                 345                 350
Lys Gly Tyr Met Phe Glu Ser Lys Arg Met Lys Leu Arg Thr Gln Ile
                355                 360                 365
Pro Ala Glu Met Leu Ala Ser Ile Asp Leu Lys Tyr Phe Asn Glu Ser
                370                 375                 380
Thr Arg Lys Lys Ile Glu Lys Ile Arg Pro Leu Leu Ile Asp Gly Thr
385                 390                 395                 400
Ala Ser Leu Ser Pro Gly Met Met Gly Met Phe Asn Met Leu Ser
                405                 410                 415
Thr Val Leu Gly Val Ser Ile Leu Asn Leu Gly Gln Lys Lys Tyr Thr
                420                 425                 430
Lys Thr Thr Tyr Trp Trp Asp Gly Leu Gln Ser Ser Asp Asp Phe Ala
                435                 440                 445
Leu Ile Val Asn Ala Pro Asn His Glu Gly Ile Gln Ala Gly Val Asn
                450                 455                 460
Arg Phe Tyr Arg Thr Cys Lys Leu Val Gly Ile Asn Met Ser Lys Lys
465                 470                 475                 480
Lys Ser Tyr Ile Asn Lys Thr Gly Thr Phe Glu Phe Thr Ser Phe Phe
                485                 490                 495
Tyr Arg Tyr Gly Phe Val Ala Asn Phe Ser Met Glu Leu Pro Ser Phe
                500                 505                 510
Gly Val Ser Gly Ile Asn Glu Ser Ala Asp Met Ser Ile Gly Val Thr
                515                 520                 525
Val Ile Lys Asn Asn Met Ile Asn Asn Asp Leu Gly Pro Ala Thr Ala
                530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Leu
                565                 570                 575
Lys Lys Leu Trp Asp Gln Thr Gln Ser Arg Ala Gly Leu Leu Val Ser
                580                 585                 590
Asp Gly Gly Pro Asn Leu Tyr Asn Ile Arg Asn Leu His Ile Pro Glu
                595                 600                 605
Val Cys Leu Lys Trp Glu Leu Met Asp Glu Asn Tyr Arg Gly Arg Leu
                610                 615                 620
Cys Asn Pro Leu Asn Pro Phe Val Ser His Lys Glu Ile Glu Ser Val
625                 630                 635                 640
Asn Asn Ala Val Val Met Pro Ala His Gly Pro Ala Lys Ser Met Glu
                645                 650                 655
Tyr Asp Ala Val Ala Thr Thr His Ser Trp Ile Pro Lys Arg Asn Arg
                660                 665                 670
Ser Ile Leu Asn Thr Ser Gln Arg Gly Ile Leu Glu Asp Glu Gln Met
                675                 680                 685
Tyr Gln Lys Cys Cys Asn Leu Phe Glu Lys Phe Phe Pro Ser Ser Ser
                690                 695                 700
Tyr Arg Arg Pro Ile Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
```

```
Lys Glu Glu Phe Ser Glu Ile Met Lys Ile Cys Ser Thr Ile Glu Glu
                    740                 745                 750

Leu Arg Arg Gln Arg
        755

<210> SEQ ID NO 37
<211> LENGTH: 759
<212> TYPE: PRT
<213> ORGANISM: Influenza A virus

<400> SEQUENCE: 37

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Thr Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Arg Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
```

```
              340             345             350
Lys Ile Arg Val His Glu Gly Tyr Glu Glu Phe Thr Met Val Gly Lys
    355                 360                 365

Arg Ala Thr Ala Ile Leu Arg Lys Ala Thr Arg Arg Leu Val Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
            435                 440                 445

Trp Gly Ile Glu His Ile Asp Ser Val Met Gly Met Val Gly Val Leu
        450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Arg Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Ala Val
545                 550                 555                 560

Lys Ile Gln Trp Ser Gln Asn Pro Ala Met Leu Tyr Asn Lys Met Glu
                565                 570                 575

Phe Glu Pro Phe Gln Ser Leu Val Pro Lys Ala Ile Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
            660                 665                 670

Gly Thr Leu Ile Glu Asp Pro Asp Glu Ser Thr Ser Gly Val Glu Ser
        675                 680                 685

Ala Val Leu Arg Gly Phe Leu Ile Ile Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
            755
```

<210> SEQ ID NO 38
<211> LENGTH: 498
<212> TYPE: PRT
<213> ORGANISM: Influenza A virus

<400> SEQUENCE: 38

```
Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ser Ser Gly
        275                 280                 285

Tyr Asn Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Gly Thr Leu Glu Leu Arg Ser Gly
```

```
                370                 375                 380
Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
                420                 425                 430

Thr Glu Gly Arg Thr Ser Asp Met Arg Ala Glu Ile Ile Arg Met Met
                435                 440                 445

Glu Gly Ala Lys Pro Glu Glu Val Ser Phe Arg Gly Arg Gly Val Phe
                450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 39
<211> LENGTH: 252
<212> TYPE: PRT
<213> ORGANISM: Influenza A virus

<400> SEQUENCE: 39

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Ala Leu Met Glu Trp Leu Lys Thr
                35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
                100                 105                 110

Lys Glu Ile Ala Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
        130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
                180                 185                 190

Ala Gly Ser Ser Glu Gln Ala Ala Glu Ala Met Glu Ile Ala Ser Gln
            195                 200                 205

Ala Arg Gln Met Val Gln Ala Met Arg Ala Ile Gly Thr His Pro Ser
        210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
```

<210> SEQ ID NO 40
<211> LENGTH: 97
<212> TYPE: PRT
<213> ORGANISM: Influenza A virus

<400> SEQUENCE: 40

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Asn Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Ala Asp Asp Ser His Phe Val Ser Ile Glu Leu
                85                  90                  95

Glu

<210> SEQ ID NO 41
<211> LENGTH: 846
<212> TYPE: DNA
<213> ORGANISM: Influenza A virus

<400> SEQUENCE: 41
aatggattcc aacactgtgt caagtttcca ggtagattgc tttctttggc atatccggaa      60
acaagttgta gaccaagaac tgagtgatgc cccattcctt gatcggcttc gccgagatca     120
gaggtcccta aggggaagag gcaatactct cggtctagac atcaaagcag ccacccatgt     180
tggaaagcaa attgtagaaa agattctgaa agaagaatct gatgaggcac ttaaaatgac     240
catggtctcc acacctgctt cgcgatacat aactgacatg actattgagg aattgtcaag     300
aaactggttc atgctaatgc caagcagaaa gtggaaggac ctctttgcat cagaatgga     360
ccaggcaatc atggagaaaa acatcatgtt gaaagcgaat ttcagtgtga tttctgaccg     420
actagagacc atagtattac taagggcttt caccgaagag ggagcaattg ttggcgaaat     480
ctcaccattg ccttcttttc aggacatac tattgaggat gtcaaaaatg caattggggt     540
cctcatcgga ggacttgaat ggaatgataa cacagttcga gtctctaaaa atctacagag     600
attcgcttgg agaagcagta atgagaatgg gggacctcca cttactccaa aacagaaacg     660
gaaaatggcg agaacagcta ggtcaaaagt ttgaagagat aagatggctg attgaagaag     720
tgagacacag actaaaaaca actgaaaata gctttgaaca ataacattc atgcaagcat     780
tacaactgct gtttgaagtg gaacaggaga taagaacttt ctcatttcag cttatttaat     840
gataaa                                                                846

<210> SEQ ID NO 42
<211> LENGTH: 566
<212> TYPE: PRT
<213> ORGANISM: Influenza A virus

<400> SEQUENCE: 42

Met Lys Thr Ile Ile Ala Leu Ser Tyr Ile Leu Cys Leu Val Phe Ala
1               5                   10                  15

-continued

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
    275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
        340                 345                 350

Gly Phe Ile Glu Asn Gly Trp Glu Gly Met Val Asp Gly Trp Tyr Gly
    355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu

```
                    435                 440                 445
Asn Gln His Thr Ile Asp Leu Thr Asp Ser Glu Met Asn Lys Leu Phe
450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                    485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 43
<211> LENGTH: 469
<212> TYPE: PRT
<213> ORGANISM: Influenza A virus

<400> SEQUENCE: 43

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
                20                  25                  30

Val Thr Leu His Phe Lys Gln Tyr Glu Phe Asn Ser Pro Pro Asn Asn
            35                  40                  45

Gln Val Met Leu Cys Glu Pro Thr Ile Ile Glu Arg Asn Ile Thr Glu
        50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
        130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
                180                 185                 190

Cys Val Thr Gly Asp Asp Lys Asn Ala Thr Ala Ser Phe Ile Tyr Asn
            195                 200                 205

Gly Arg Leu Val Asp Ser Ile Val Ser Trp Ser Lys Glu Ile Leu Arg
        210                 215                 220

Thr Gln Glu Ser Glu Cys Val Cys Ile Asn Gly Thr Cys Thr Val Val
225                 230                 235                 240
```

```
Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Leu Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 44
<211> LENGTH: 716
<212> TYPE: PRT
<213> ORGANISM: Influenza A virus

<400> SEQUENCE: 44

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Ile Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140
```

```
Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Lys Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560
```

```
Met Phe Leu Tyr Val Arg Thr Asn Gly Thr Ser Lys Ile Lys Met Lys
            565                 570                 575

Trp Gly Met Glu Met Arg Arg Cys Leu Leu Gln Ser Leu Gln Gln Ile
        580                 585                 590

Glu Ser Met Ile Glu Ala Glu Ser Val Lys Glu Lys Asp Met Thr
    595                 600                 605

Lys Glu Phe Phe Glu Asn Lys Ser Glu Thr Trp Pro Ile Gly Glu Ser
    610                 615                 620

Pro Arg Gly Val Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715

<210> SEQ ID NO 45
<211> LENGTH: 252
<212> TYPE: PRT
<213> ORGANISM: Influenza A virus

<400> SEQUENCE: 45

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asn Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Ser Ala Phe
    130                 135                 140

Gly Leu Ile Cys Ala Thr Cys Glu Gln Ile Ala Asp Ser Gln His Lys
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr His Pro Ser
    210                 215                 220
```

```
Ser Ser Thr Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 46
<211> LENGTH: 758
<212> TYPE: PRT
<213> ORGANISM: Influenza A virus

<400> SEQUENCE: 46

```
Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
```

```
            340             345             350
Lys Gly Tyr Met Phe Glu Ser Lys Arg Met Lys Leu Arg Thr Gln Ile
        355             360             365

Pro Ala Glu Met Leu Ala Ser Ile Asp Leu Lys Tyr Phe Asn Glu Ser
    370             375             380

Thr Arg Lys Lys Ile Glu Lys Ile Arg Pro Leu Leu Ile Asp Gly Thr
385             390             395             400

Ala Ser Leu Ser Pro Gly Met Met Met Gly Met Phe Asn Met Leu Ser
            405             410             415

Thr Val Leu Gly Val Ser Ile Leu Asn Leu Gly Gln Lys Lys Tyr Thr
            420             425             430

Lys Thr Thr Tyr Trp Trp Asp Gly Leu Gln Ser Ser Asp Asp Phe Ala
        435             440             445

Leu Ile Val Asn Ala Pro Asn His Glu Gly Ile Gln Ala Gly Val Asp
        450             455             460

Arg Phe Tyr Arg Thr Cys Lys Leu Val Gly Ile Asn Met Ser Lys Lys
465             470             475             480

Lys Ser Tyr Ile Asn Arg Thr Gly Thr Phe Glu Phe Thr Ser Phe Phe
            485             490             495

Tyr Arg Tyr Gly Phe Val Ala Asn Phe Ser Met Glu Leu Pro Ser Phe
            500             505             510

Gly Val Ser Gly Ile Asn Glu Ser Ala Asp Met Ser Ile Gly Val Thr
            515             520             525

Val Ile Lys Asn Asn Met Ile Asn Asn Asp Leu Gly Pro Ala Thr Ala
            530             535             540

Gln Met Ala Leu Gln Leu Phe Ile Lys Asp Tyr Arg Tyr Thr Tyr Arg
545             550             555             560

Cys His Arg Gly Asp Thr Gln Ile Gln Thr Arg Arg Ser Phe Glu Leu
            565             570             575

Lys Lys Leu Trp Glu Gln Thr Arg Ser Lys Ala Gly Leu Leu Val Ser
            580             585             590

Asp Gly Gly Pro Asn Leu Tyr Asn Ile Arg Asn Leu His Ile Pro Glu
            595             600             605

Val Cys Leu Lys Trp Glu Leu Met Asp Glu Asp Tyr Gln Gly Arg Leu
        610             615             620

Cys Asn Pro Leu Asn Pro Phe Val Ser His Lys Glu Ile Glu Ser Val
625             630             635             640

Asn Asn Ala Val Val Met Pro Ala His Gly Pro Ala Lys Ser Met Glu
            645             650             655

Tyr Asp Ala Val Ala Thr Thr His Ser Trp Ile Pro Lys Arg Asn Arg
            660             665             670

Ser Ile Leu Asn Thr Ser Gln Arg Gly Ile Leu Glu Asp Glu Gln Met
        675             680             685

Tyr Gln Lys Cys Cys Asn Leu Phe Glu Lys Phe Phe Pro Ser Ser Ser
        690             695             700

Tyr Arg Arg Pro Val Gly Ile Ser Ser Met Val Glu Ala Met Val Ser
705             710             715             720

Arg Ala Arg Ile Asp Ala Arg Ile Asp Phe Glu Ser Gly Arg Ile Lys
            725             730             735

Lys Glu Glu Phe Ser Glu Ile Met Lys Ile Cys Ser Thr Ile Glu Glu
            740             745             750

Leu Arg Arg Gln Lys Gln
        755
```

<210> SEQ ID NO 47
<211> LENGTH: 716
<212> TYPE: PRT
<213> ORGANISM: Influenza A virus

<400> SEQUENCE: 47

```
Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
```

```
                    370                 375                 380
Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                    405                 410                 415

Leu Thr Asp Ser Ser Trp Ile Glu Leu Asp Glu Ile Gly Glu Asp Val
                420                 425                 430

Ala Pro Ile Glu His Ile Ala Ser Met Arg Arg Asn Tyr Phe Thr Ser
                435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
                500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
                660                 665                 670

Arg Asp Asn Leu Glu Pro Gly Thr Phe Asp Leu Gly Gly Leu Tyr Glu
                675                 680                 685

Ala Ile Glu Glu Cys Leu Ile Asn Asp Pro Trp Val Leu Leu Asn Ala
            690                 695                 700

Ser Trp Phe Asn Ser Phe Leu Thr His Ala Leu Ser
705                 710                 715

<210> SEQ ID NO 48
<211> LENGTH: 326
<212> TYPE: PRT
<213> ORGANISM: Influenza A virus

<400> SEQUENCE: 48

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30
```

```
Ile Gly Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
 50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
            115                 120                 125

Ala Thr Ala Gly Leu Thr His Met Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
            195                 200                 205

Gly Glu Asn Gly Arg Lys Thr Arg Ile Ala Tyr Glu Arg Met Cys Asn
            210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
            275                 280                 285

Tyr Asp Phe Glu Arg Glu Gly Tyr Ser Leu Val Gly Ile Asp Pro Phe
290                 295                 300

Arg Leu Leu Gln Asn Ser Gln Val Tyr Ser Leu Ile Arg Pro Asn Glu
305                 310                 315                 320

Asn Pro Ala His Lys Ser
            325

<210> SEQ ID NO 49
<211> LENGTH: 252
<212> TYPE: PRT
<213> ORGANISM: Influenza A virus

<400> SEQUENCE: 49

Met Ser Leu Leu Thr Glu Val Glu Thr Tyr Val Leu Ser Ile Ile Pro
 1               5                  10                  15

Ser Gly Pro Leu Lys Ala Glu Ile Ala Gln Arg Leu Glu Asp Val Phe
                20                  25                  30

Ala Gly Lys Asn Thr Asp Leu Glu Val Leu Met Glu Trp Leu Lys Thr
            35                  40                  45

Arg Pro Ile Leu Ser Pro Leu Thr Lys Gly Ile Leu Gly Phe Val Phe
 50                  55                  60

Thr Leu Thr Val Pro Ser Glu Arg Gly Leu Gln Arg Arg Arg Phe Val
 65                  70                  75                  80
```

```
Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 50
<211> LENGTH: 566
<212> TYPE: PRT
<213> ORGANISM: Influenza A virus

<400> SEQUENCE: 50

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
```

```
            195                 200                 205
Tyr Gln Asn Ala Asp Thr Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Leu Lys Ser
                370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
                450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
                515                 520                 525

Gln Ile Leu Ala Ile Tyr Ser Thr Val Ala Ser Ser Leu Val Leu Val
                530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

The invention claimed is:

1. A reassortant influenza A virus comprising six backbone viral segments, an HA segment and an NA segment, wherein two, three, four, five, or six backbone viral segments are from a donor strain, wherein the donor strain is selected from the group consisting of 105p30 and PR8-X, wherein (a) at least one donor segment is selected from the group consisting of SEQ ID NOs 9-12 and SEQ ID NOs 17-22, (b) at least two donor segments are selected from the group consisting of SEQ ID NOs 9-13 and SEQ ID NOs: 17-22, or (c) at least two donor segments are selected from the group consisting of SEQ ID NOs 9-12 and 14 and SEQ ID NOs 17-22, and at least one viral segment is derived from a second influenza strain.

2. The reassortant influenza A virus of claim 1 wherein at least one backbone viral segment comprises the sequence of SEQ ID NO: 17 or SEQ ID NO: 20.

3. The reassortant influenza A virus of claim 1, wherein the virus comprises backbone segments from two or more donor strains.

4. The reassortant influenza A virus of claim 3, wherein the PB1 and the PB2 viral segments are from the same donor strain.

5. The reassortant influenza A virus of claim 4, wherein the PB1 viral segment has at least 95% identity to SEQ ID NO: 18 and the PB2 viral segment has at least 95% identity to SEQ ID NO: 19.

6. The reassortant influenza A virus of claim 5, wherein the virus further comprises a viral segment having at least 95% identity to a sequence selected from the group consisting of SEQ ID NOs 17-22.

7. The reassortant influenza A virus of claim 2, wherein the virus comprises the PB2 segment of SEQ ID NO: 19, the PB1 segment of SEQ ID NO: 18 and the NP segment of SEQ ID NO: 20.

8. The reassortant influenza A virus of claim 1, wherein the virus has the HA segment from a pandemic influenza strain.

9. A method of preparing a reassortant influenza virus comprising steps of
(i) introducing into a culture host one or more expression construct(s) which encode(s) the viral segments required to produce an influenza virus wherein at least one backbone viral segment(s) is/are from a 105p30 and/or a PR8 X influenza strain, wherein (a) at least one donor segment is selected from the group consisting of SEQ ID NOs 9-12 and SEQ ID NOs 17-22, (b) two or more backbone viral segments are selected from the group consisting of SEQ ID NOs 9-13 and SEQ ID NOs 17-22, or (c) two or more backbone viral segments are selected from the group consisting of SEQ ID NOs 9-12, SEQ ID NO: 14 and SEQ ID NOs 17-22, and wherein at least one viral segment is derived from a second influenza strain; and
(ii) culturing the culture host in order to produce reassortant virus.

10. The method of claim 9, further comprising the step (iii) of purifying the reassortant virus obtained in step (ii).

11. The method of claim 9 wherein the at least one viral segment from the second influenza strain is the HA segment.

12. A method for producing influenza viruses comprising:
(a) infecting a culture host with the reassortant influenza virus of claim 1;
(b) culturing the host from step (a) to produce the virus; and
(c) purifying the virus obtained in step (b).

13. A method of preparing a vaccine, comprising steps of
(x) preparing a virus by the method of claim 12 and
(y) preparing vaccine from the virus.

14. The method of claim 13, wherein
(i) the culture host is an embryonated hen egg, or
(ii) the culture host is a eukaryotic cell.

15. The method of claim 14, wherein the culture host is (ii) and the eukaryotic cell is an MDCK, Vero or PerC6 cell.

16. The method of claim 15, wherein the eukaryotic cell grows
(i) adherently or
(ii) in suspension.

17. The method of claim 15, wherein the eukaryotic cell is cell line MDCK 33016 (DSM ACC2219).

18. The method of claim 13, wherein step (b) includes inactivating the virus.

19. The method of claim 13, wherein the vaccine is a whole virion vaccine, a split virion vaccine, a surface antigen vaccine or a virosomal vaccine.

20. The method of claim 13, wherein the vaccine contains less than 10 ng of residual host cell DNA per dose.

21. A composition comprising six backbone viral segments, an HA segment and an NA segment, wherein two, three, four, five, or six donor polypeptides are encoded by influenza A backbone viral segments from at least one donor strain, wherein the at least one donor strain is selected from the group consisting of 105p30 and PR8 X, wherein (a) at least one donor segment is selected from the group consisting of SEQ ID NOs 9-12 and SEQ ID NOs 17-22, (b) at least two donor segments are selected from the group consisting of SEQ ID NOs 9-13 and SEQ ID NOs 17-22, or (c) at least two donor segments are selected from the group consisting of SEQ ID NOs 9-12, SEQ ID NO: 14 and SEQ ID NOs 17-22, and a hemagglutinin polypeptide encoded by the HA segment that is not from influenza strains 105p30 (SEQ ID NO: 23) or PR8 X (SEQ ID NO: 15).

22. The reassortant influenza A virus of claim 1, comprising at least one donor segment is selected from the group consisting of SEQ ID NOs 9-12.

23. The reassortant influenza A virus of claim 1, comprising at least two donor segments are selected from (a) the group consisting of SEQ ID NOs 9-13 and SEQ ID NOs 17-22, or (b) the group consisting of SEQ ID NOs 9-12, SEQ ID NO: 14 and SEQ ID NOs 17-22.

24. The method of preparing a reassortant influenza virus of claim 9, wherein at least one donor segment is selected from the group consisting of SEQ ID NOs 9-12.

25. The method of preparing a reassortant influenza virus of claim 9, wherein at least two of the two or more backbone viral segments are selected from (a) the group consisting of SEQ ID NOs 9-13 and SEQ ID NOs 17-22, or (b) the group consisting of SEQ ID NOs 9-12, SEQ ID NO: 14 and SEQ ID NO 17-22.

26. The composition of claim 21, wherein at least one donor segment is selected from the group consisting of SEQ ID NOs 9-12.

27. The composition of claim 21, wherein at least two donor segments are selected from (a) the group consisting of SEQ ID NOs: 9-13, or (b) the group consisting of SEQ ID NOs 9-12 and SEQ ID NO: 14.

28. The composition of claim 26, wherein the composition is an influenza vaccine.

29. The composition of claim 27, wherein the composition is an influenza vaccine.

* * * * *